(12) United States Patent
Curtiss, III

(10) Patent No.: US 8,133,493 B2
(45) Date of Patent: Mar. 13, 2012

(54) REGULATED ATTENUATION OF LIVE VACCINES TO ENHANCE CROSS-PROTECTIVE IMMUNOGENICITY

(75) Inventor: Roy Curtiss, III, Paradise Valley, AZ (US)

(73) Assignee: Washington University, St. Louis, MO (US)

( * ) Notice: Subject to any disclaimer, the term of this patent is extended or adjusted under 35 U.S.C. 154(b) by 1036 days.

(21) Appl. No.: 10/511,616

(22) PCT Filed: Apr. 15, 2003

(86) PCT No.: PCT/US03/11802
§ 371 (c)(1),
(2), (4) Date: Nov. 15, 2005

(87) PCT Pub. No.: WO03/096812
PCT Pub. Date: Nov. 27, 2003

(65) Prior Publication Data
US 2006/0233829 A1    Oct. 19, 2006

(51) Int. Cl.
*A61K 39/02* (2006.01)
*A61K 39/112* (2006.01)
*A61K 45/00* (2006.01)
*G01N 33/569* (2006.01)
*C12P 1/00* (2006.01)

(52) U.S. Cl. ............... 424/200.1; 424/258.1; 424/282.1; 435/7.35; 435/41

(58) Field of Classification Search ............... 424/258.1, 424/282.1, 200.1; 432/7.35, 41
See application file for complete search history.

(56) References Cited

U.S. PATENT DOCUMENTS

| | | | |
|---|---|---|---|
| 5,389,368 A | 2/1995 | Curtiss, III | |
| 5,527,529 A | 6/1996 | Dougan et al. | |
| 5,747,309 A | 5/1998 | Allan | |
| 5,855,879 A | 1/1999 | Curtiss, III | |
| 5,888,799 A | 3/1999 | Curtiss, III | |
| 6,024,961 A * | 2/2000 | Curtiss et al. ............. | 424/200.1 |
| 6,248,329 B1 * | 6/2001 | Chandrashekar et al. . | 424/191.1 |
| 6,521,441 B1 * | 2/2003 | Simpson et al. ........... | 435/252.3 |

FOREIGN PATENT DOCUMENTS

| WO | 91/06317 A1 | 5/1991 |
|---|---|---|
| WO | WO91/06317 * | 5/1991 |
| WO | 98/56901 A2 | 12/1998 |
| WO | WO00/04919 A2 * | 2/2000 |
| WO | WO 91/06317 * | 5/2001 |
| WO | WO 01/83785 A2 * | 11/2001 |
| WO | WO01/83785 A2 * | 11/2001 |
| WO | WO 01/83785 A2 * | 2/2003 |

OTHER PUBLICATIONS

Greenspan et al. (Nature Biotechnology 7: 936-937, 1999).*
Bolin et al 1987 Infection and Immunity pp. 1239-1242.*
Sood et al 2005 Molecular and Cellular Biochemistry vol. 273 pp. 69-78.*
Ellis (Chapter 29 of Vaccines, Plotkin, et al. (eds) WB Saunders, Philadelphia, 1998.*
Alpuche-Aranda, C., et al., *Salmonella typhimurium* activates virulence gene transcription within acidified macrophage phagosomes, Proc. Natl. Acad. Sci. USA, 1992, pp. 10079-10083, vol. 89, Microbiology.
Bagg, A., et al., Molecular Mechanism of Regulation of Siderophore-Mediated Iron Assimilation, Molecular Reviews, 1987, pp. 509-518, vol. 51 No. 4, American Society for Microbiology.
Bolin, C., et al., Passive Immunization with Antibodies against Iron-Regulated Outer Membrane Proteins Protects Turkeys from *Escherichia coli* Septicemia, Infection and Immunity, 1987, pp. 1239-1242, vol. 55 No. 5, American Society for Microbiology.
Collins, L., et al., Mutations at rfc or pmi Attenuate *Salmonella typhimurium* Virulence for Mice, Infection and Immunity, 1991, pp. 1079-1085, vol. 59, No. 3, American Society for Microbiology.
Englesberg, E., et al., Positive Control of Enzyme Synthesis by Gene C in the *L-Arabinose* System, Journal of Bacteriology, 1965, pp. 946-957, vol. 90 No. 4, American Society for Microbiology.
Ernst, J., et al., Constitutive Expression of the Iron-Enterochelin and Ferrichrome Uptake Systems in a Mutant Strain of *Salmonella typhimurium*, Journal of Bacteriology, 1978, pp. 928-934, vol. 135 No. 3, American Society for Microbiology.
Fields, P., et al., Mutants of *Salmonella typhimurium* that cannot survive within the macrophage are avirulent, Proc. Natl. Acad. Sci. USA, 1986, pp. 5189-5193, vol. 83, Genetics.
Finlay, B., et al., Identification and characterization of TnphoA mutants of *Salmonella* that are unable to pass through a polarized MDCK epithelial cell monolayer, Molecular Microbiology, 1988, pp. 757-766, vol. 2 No. 6.
Foster, J., et al., Effect of *Salmonella typhimurium* Ferric Uptake Regulator (fur) Mutations on Iron- and pH-Regulated Protein Synthesis, Journal of Bacteriology, 1992, pp. 4317-4323, vol. 174 No. 13, American Society for Microbiology.
Fukasawa, T., et al., Galactose-sensitive Mutants of *Salmonella*, Nature, 1959, pp. 1168-1169, vol. 184, Nature Publishing Group, London, UK.
Garcia-Del Portillo, F., et al., Role of Acid Tolerance Response Genes in *Salmonella typhimurium* Virulence, Infection and Immunity, 1993, pp. 4489-4492, vol. 61, No. 10, American Society for Microbiology.
Germanier, R., et al., Immunity in Experimental Salmonellosis, Infection and Immunity, 1971, pp. 663-673, vol. 4 No. 6, American Society for Microbiology.
Guzman, L., et al., Tight Regulation, Modulation, and High-Level Expression by Vectors Containing the Arabinose P-bad Promoter, Journal of Bacteriology, 1995, pp. 4121-4130, vol. 177 No. 14., American Society for Microbiology.
Hall, H., et al., The Role of Fur in the Acid Tolerance Response of *Salmonella typhimurium* Is Physiologically and Genetically Separable from Its Role in Iron Acquisition, Journal of Bacteriology, 1996, pp. 5683-5691, vol. 178 No. 19, American Society for Microbiology.

(Continued)

*Primary Examiner* — Vanessa L Ford
*Assistant Examiner* — Nina Archie
(74) *Attorney, Agent, or Firm* — Thompson Coburn LLP

(57) ABSTRACT

A live attenuated derivative of a pathogenic bacterium intended for use as a vaccine.

6 Claims, 54 Drawing Sheets

OTHER PUBLICATIONS

Hantke, K., Selection procedure for deregulated iron transport mutants (fur) in *Escherichia coli* K 12: fur not only affects iron metabolism, Molecular and General Genetics, 1987, pp. 135-139, vol. 210, Springer-Verlag.

Hassan, J., et al., Development and Evaluation of an Experimental Vaccination Program Using a Live Avirulent *Salmonella typhimurium* Strain to Protect Immunized Chickens against Challenge with Homologous and Heterologous *Salmonella* Serotypes, Infection and Immunity, 1994, pp. 5519-5527, vol. 62 No. 12., American Society for Microbiology.

Hensel, M., et al., Simultaneous Identification of Bacterial Virulence Genes by Negative Selection, Science, 1995, pp. 400-403, vol. 269.

Klena, J., et al., Function of the rfb gene cluster and the rfe gene in the synthesis of O antigen by *Shigella dysenteriae* 1, Molecular Microbiology, 1993, pp. 393-402, vol. 9 No. 2.

Lin, J., et al., Antigenic Homology of the Inducible Ferric Citrate Receptor (FecA) of *Coliform* Bacteria Isolated from Herds with Naturally Occurring Bovine Intramammary Infections, Clinical and Diagnostic Laboratory Immunology, 1999, pp. 966-969, vol. 6 No. 6, American Society for Microbiology.

Markovitz, A., et al., Genetic and Biochemical Studies on Mannose-Negative Mutants That Are Deficient in Phosphomannose Isomerase in *Escherichia coli* K-12, Journal of Bacteriology, 1967, pp. 1492-1496, vol. 94 No. 5, American Society for Microbiology.

Medina, E., et al., Use of live bacterial vaccine vectors for antigen delivery: potential and limitations, Vaccine, 2001, pp. 1573-1580, vol. 19, Elsevier.

Muotiala, A., et al., Protective immunity in mouse salmonellosis: comparison of smooth and rough live and killed vaccines, Microbial Pathogenesis, 1989, pp. 51-60, vol. 6, Academic Press Limited.

Nnalue, N., All Accessible Epitopes in the *Salmonella* Lipopolysaccharide Core Are Associate with Branch Residues, Infection and Immunity, 1999, pp. 998-1003, vol. 67 No. 2., American Society for Microbiology.

Nnalue, N., et al., Tests of the Virulence and Live-Vaccine Efficacy of Auxotrophic and galE Derivatives of *Salmonella choleraesuis*, Infection and Immunity, 1987, pp. 955-962, vol. 55 No. 4, American Society for Microbiology.

Reeves, P., Role of O-antigen variation in the immune response, Trends in Microbiology, 1995, pp. 381-386, vol. 3 No. 10, Elsevier Science Ltd.

Rosen, S., et al., Characterization of the Cell Wall *Lipopolysaccharide* of a Mutant of *Salmonella typhimurium* Lacking Phosphomannose Isomerase, Biochemische Zeitschrift, 1965, pp. 375-386, vol. 342.

Vancott, J., et al., Regulation of host immune responses by modification of *Salmonella* virulence genes, Nature Medicine, 1998, pp. 1247-1252, vol. 4 No. 11, Nature America Inc.

Wilmes-Riesenberg, M., et al., Role of the Acid Tolerance Response in Virulence of *Salmonella typhimurium*, Infection and Immunity, 1996, pp. 1085-1092, vol. 64 No. 4, American Society for Microbiology.

Curtiss, III, et al., "*Salmonella typhimurium* Deletion Mutants Lacking Adenylate Cyclase and Cyclic AMP Receptor Protein Are Avirulent and Immunogenic", Infection and Immunity, Dec. 1987, pp. 3035-3043, vol. 55, No. 12, American Society for Microbiology.

Curtiss, III, et al., "*Salmonella enterica Serovar Typhimurium* Strains with Regulated Delayed Attenuation in Vivo" Infection and Immunity, Mar. 2009, pp. 1071-1082, vol. 77, No. 3, American Society for Microbiology.

European Supplementary European Search Report for Corresponding EP Application EP Application 03721711.4 dated May 23, 2006.

Zhang et al. "*Salmonella Typhimurium* UK-1 ΔPfur::araCPbadfur Δpmi Mutants are Highly Attenuated and Induced Protective Immunity in BALB/c Mice" Abstract of the General Meeting of the American Society for Microbiology, May 2002, Session No. 167; vol. 102, pp. 512-513.

Kong et al., "Regulated Bacterial Lysis for Antigen Release", Abstract of the General Meeting of the American Society for Microbiology, 2003, p. E-031 URL, vol. 103.

Kennedy et al.; "Attenuation and Immunogenicity of Δcya Δcrp Derivatives of *Salmonella Choleraesuis* in Pigs"; Infection and Immunity; Sep. 1999; pp. 4628-4636; vol. 67, No. 9; American Society for Microbiology.

Di Padova et al.; "A Broadly Cross-Protective Monoclonal Antibody Binding to *Escherichia coli* and *Salmonella Lipopolysaccharides*"; Infection and Immunity; Sep. 1993; pp. 3863-3872; vol. 61, No. 9; American Society for Microbiology.

Heinrichs et al.; "Molecular Basis for Structural Diversity in the Core Regions of the Lipopolysaccharides of *Escherichia coli* and *Salmonella enterica*"; Molecular Microbiology; 1998; pp. 221-232; vol. 30, No. 2; Blackwell Science Ltd.

Newman et al.; "Broad-host-range Expression Vectors that Carry the L-arabinose-inducible *Escherichia coli* araBAD Promoter and the araC Regulator"' Gene; Feb. 18, 1999; pp. 197-203;vol. 227, No. 2; Elsevier.

Cookson et al.; "Identification of a Natural T Cell Epitope Presented by *Salmonella*-infected Macrophages and Recognized by T Cells from Orally Immunized Mice"; Journal of Immunology; 1997; pp. 4310-4319; vol. 158, No. 9; The American Association of Immunologists.

Van Der Velden et al.; "Multiple Fimbrial Adhesins are Required for Full Virulence of *Salmonella typhimurium* in Mice"; Infection and Immunity; Jun. 1998; pp. 2803-2808; vol. 66, No. 6; American Society for Microbiology.

Jensen et al.; "The Role of Flagella and Chemotaxis on Virulence of *Salmonella enterica* Serotypes in the Murine and Avian Hosts"; Abstracts of the General Meeting of the American Society for Microbiology; May 22, 2001; p. 429; vol. 101; Orlando, Florida.

Heithoff et al.; "An Essential Role for DNA Adenine Methylation in Bacterial Virulence"; Science; May 7, 1999; pp. 967-970; vol. 284; American Association for the Advancement of Science.

Collazo et al.; "The Invasion—associated Type III System of *Salmonella typhimurium* Directs the Translocation of Sip Proteins into the Host Cell"; Molecular Microbiology; 1997; pp. 747-756; vol. 24, No. 4; Blackwell Science Ltd.

Curtiss III, Roy; "Bacterial Infectious Disease Control by Vaccine Development"; The Journal of Clinical Investigation; Oct. 2002; pp. 1061-1066; vol. 110, No. 8.

* cited by examiner

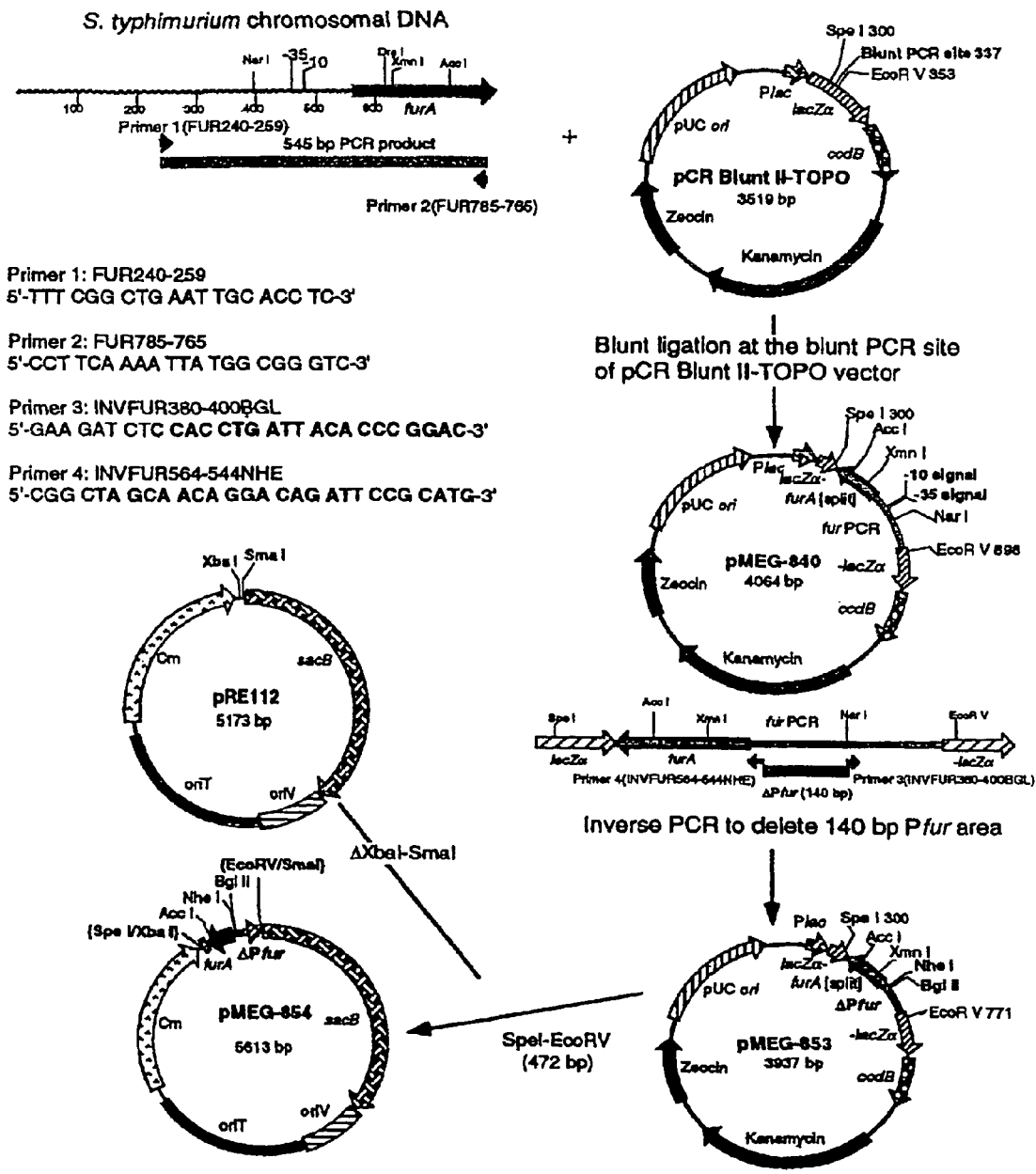
Figure 1-A. Construction of suicide vector for transfer of ΔPfur223::TTaraC P_BAD fur deletion-insertion mutation.

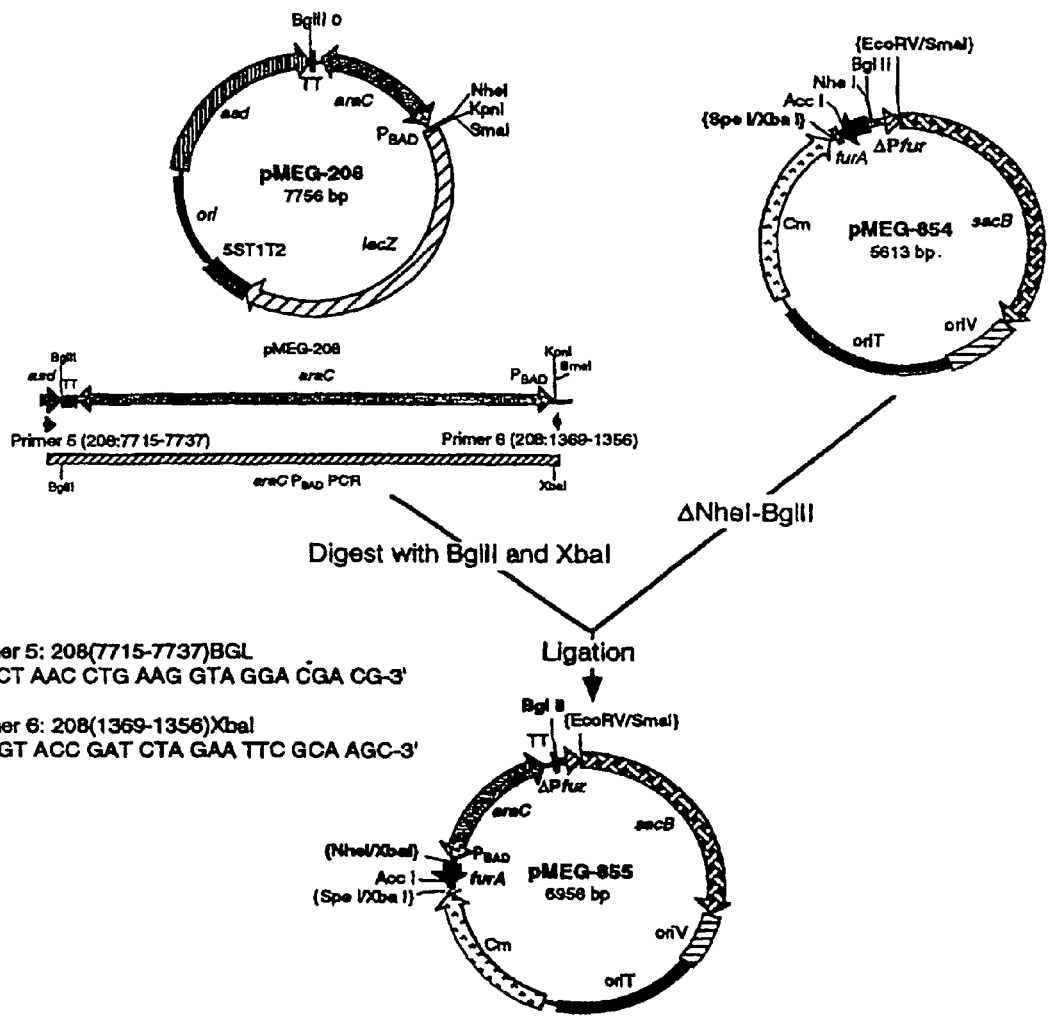
Figure 1-B. Construction of suicide vector for transfer of ΔPfur223::TTaraC P_BAD *fur* deletion-insertion mutation.

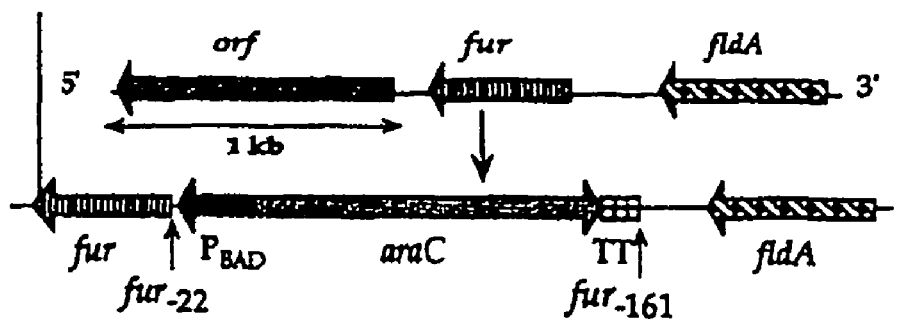
140 bp *fur* promotor region deleted
1,354 bp TT*araC* P$_{BAD}$ inserted
Figure 2. ΔPfur223::TT*araC* P$_{BAD}$*fur* deletion-insertion chromosomal construction.

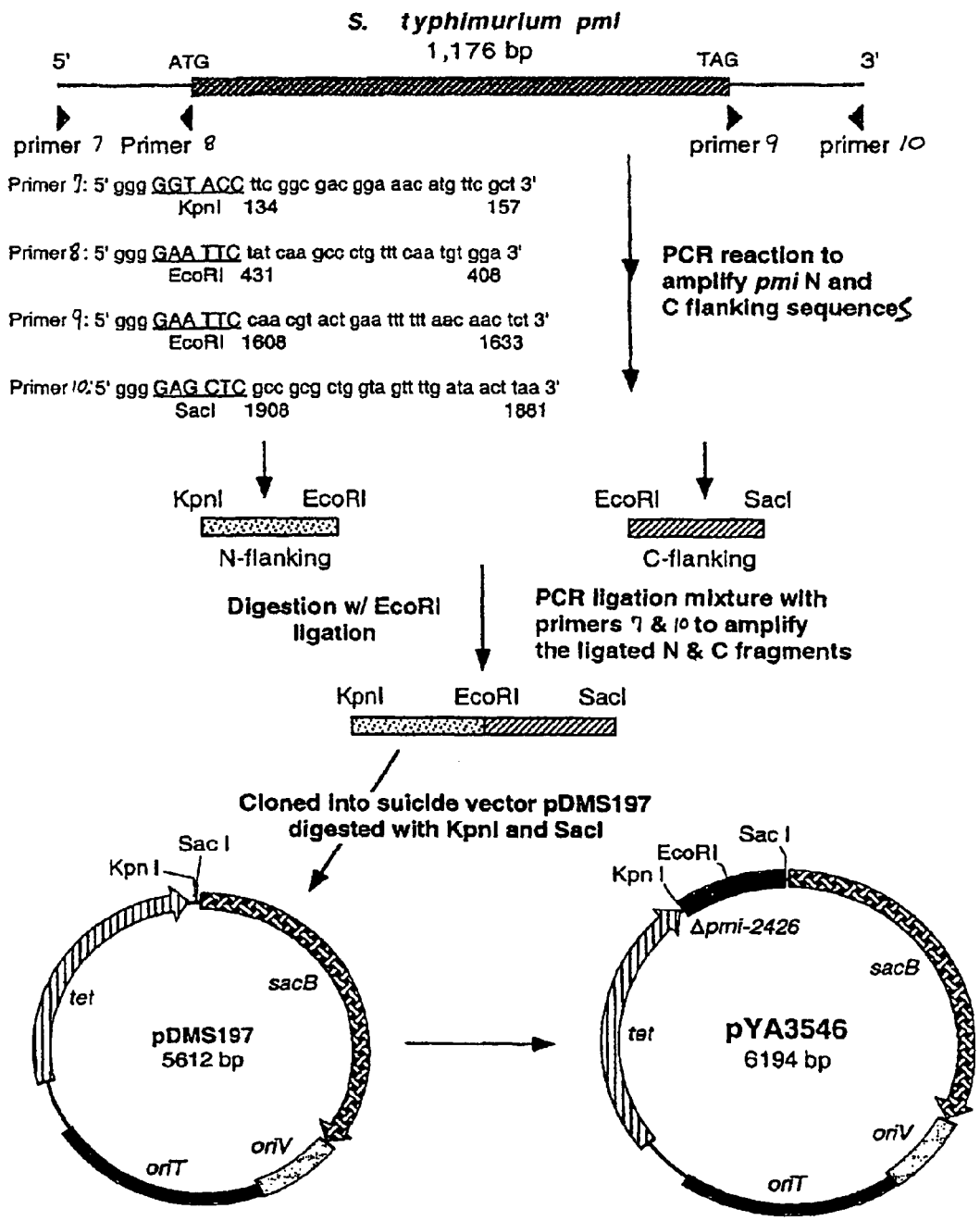
Figure 3. Construction of a suicide vector for *pmi* deletion.

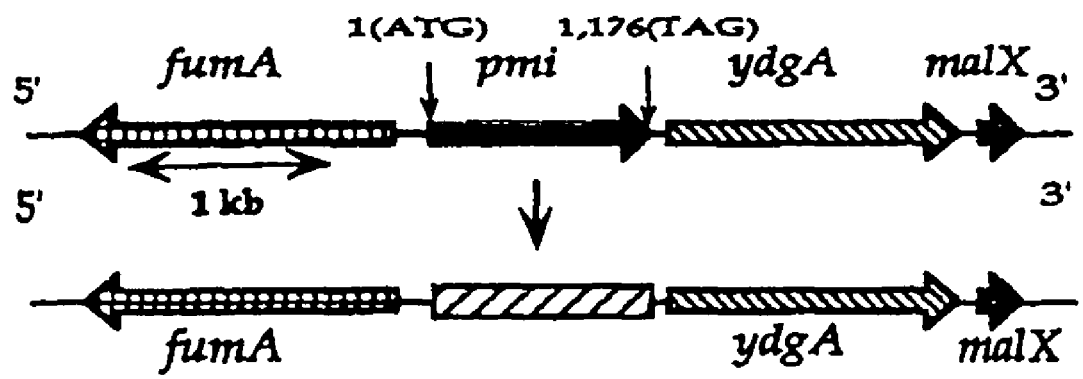
Figure 4. Chromosomal deletion for Δpmi-2426

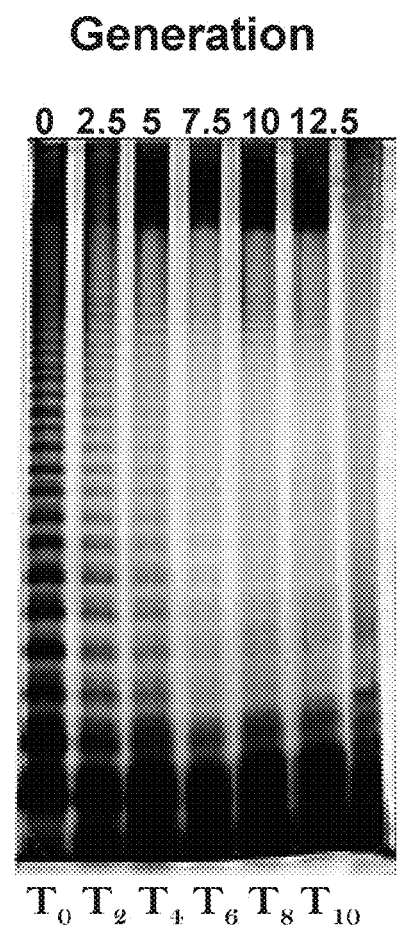
Figure 5. Reduction of LPS O-side chains in χ8650 as a function of numbers of generations of growth or times (hours) of sampling.

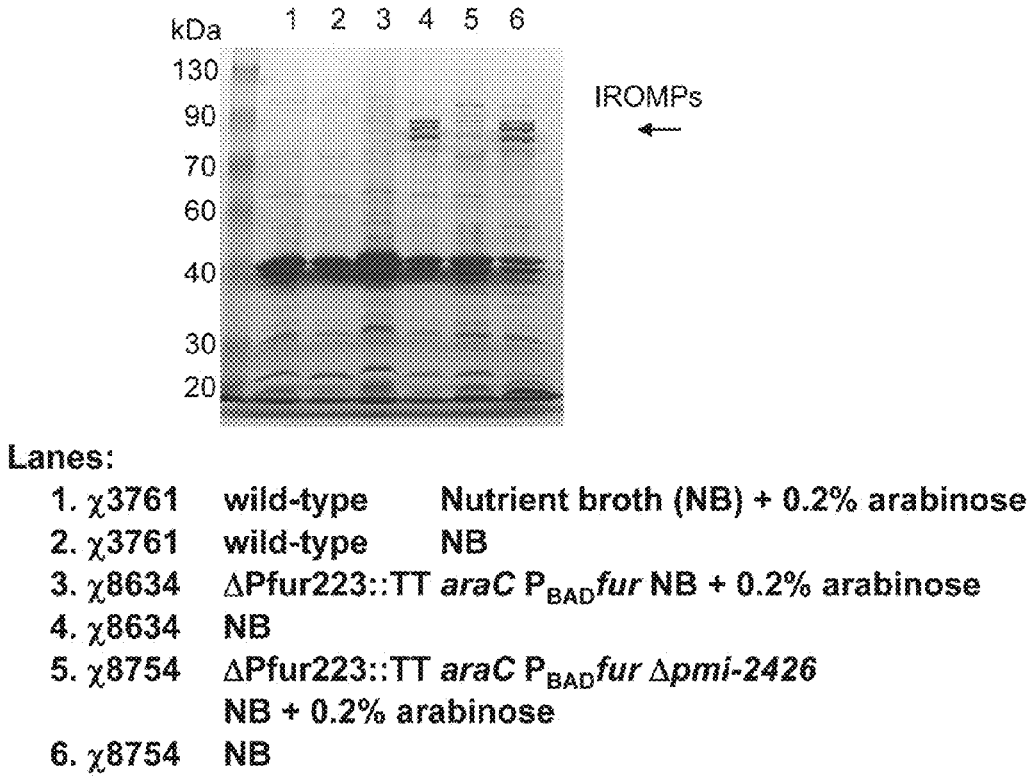
Figure 6. Outer membrane protein profile of ΔPfur223::TT araC $P_{BAD}$fur mutants grown in Nutrient broth +/- arabinose.

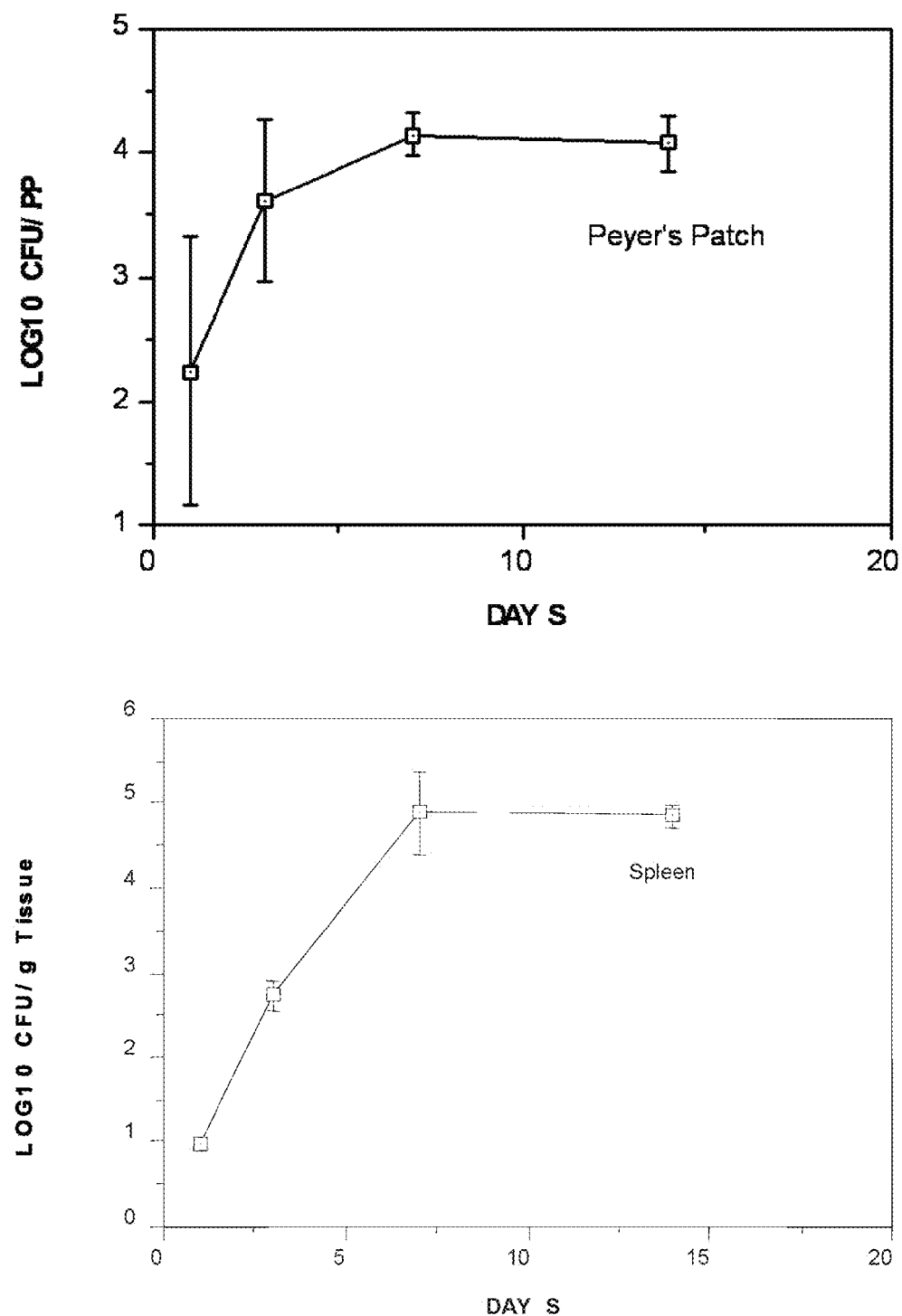
Figure 7. Colonization of 8-week-old female BALB/c mice with χ8634 ΔPfur223::TTaraC PBAD fur following oral inoculation.

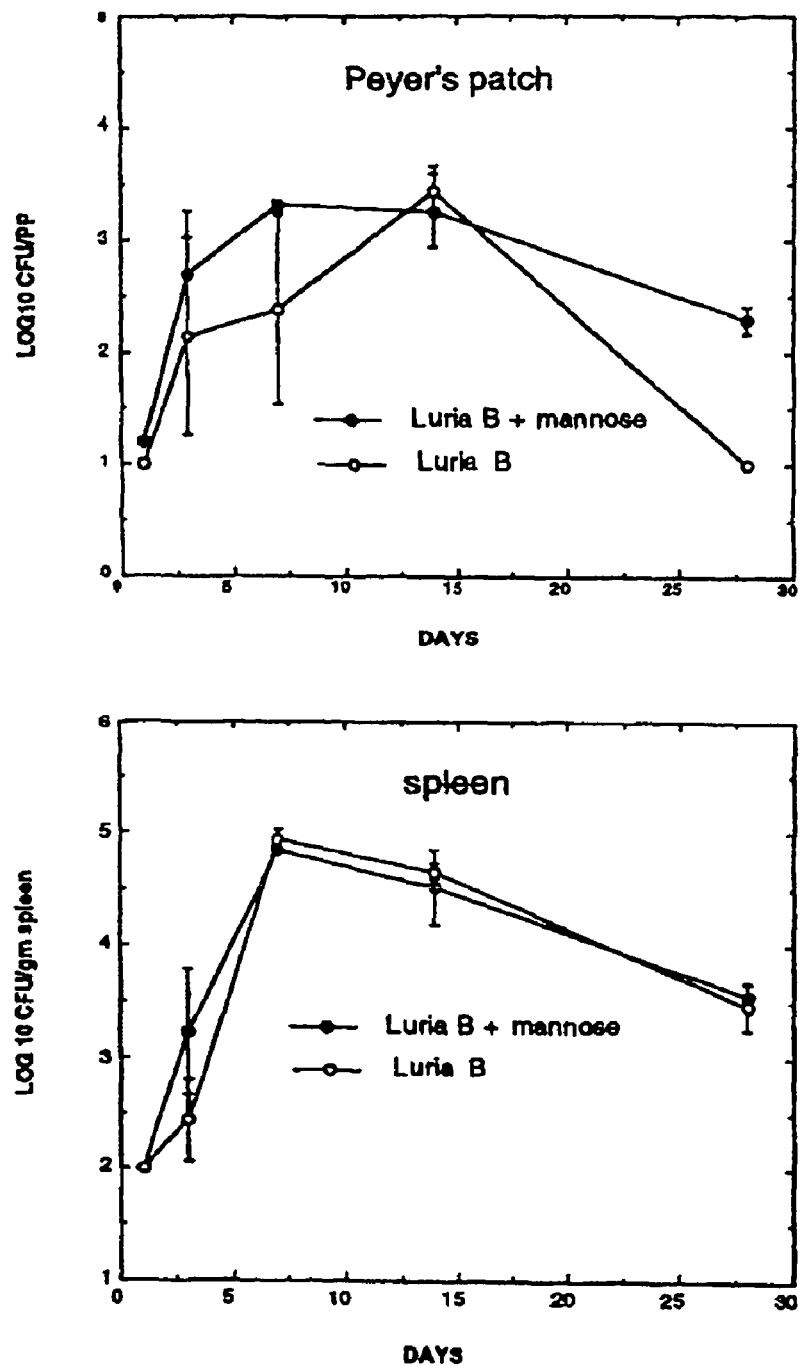
Figure 8. Colonization of 8-week-old female BALB/c mice with χ8650 (Δpmi-2426) following oral inoculation.

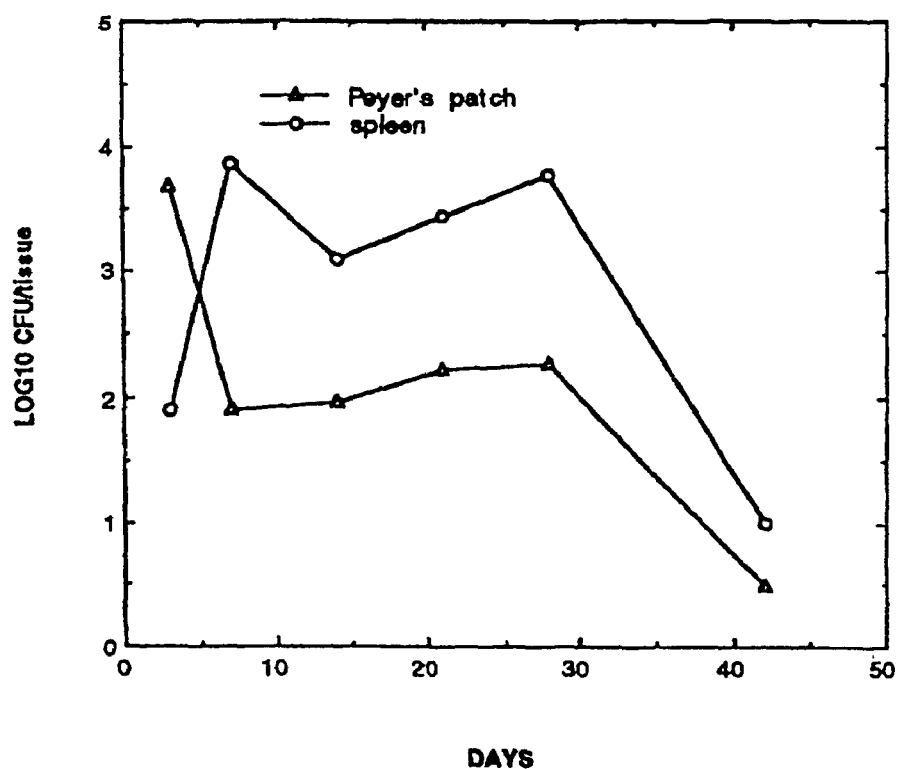
Figure 9. Colonization of 8-week-old female BALB/c mice with χ8754 (Δ*pmi-2426* ΔPfur223::*araC* P$_{BAD}$ *fur*) following oral inoculation.

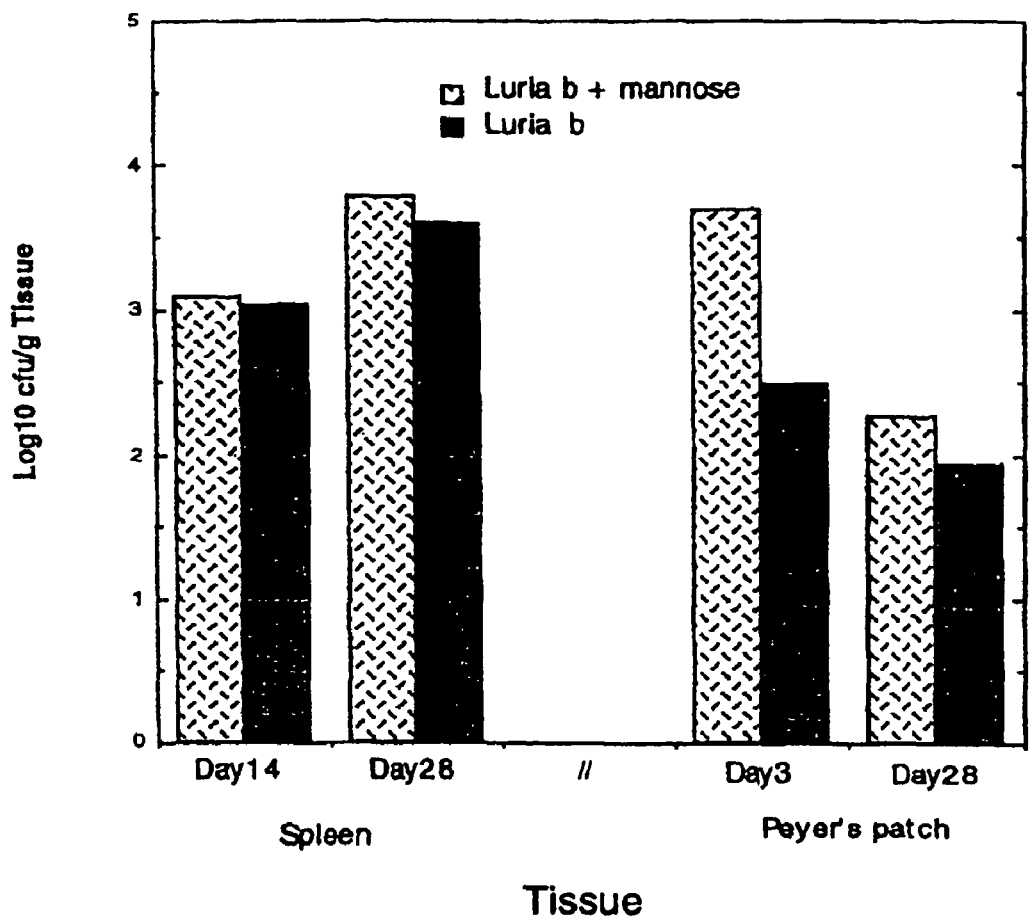
Figure 10. Colonization of 8-week-old female BALB/c mice with χ8754 ($\Delta pmi$-2426 $\Delta$Pfur223::TTaraC $P_{BAD}$ fur) following oral inoculation.

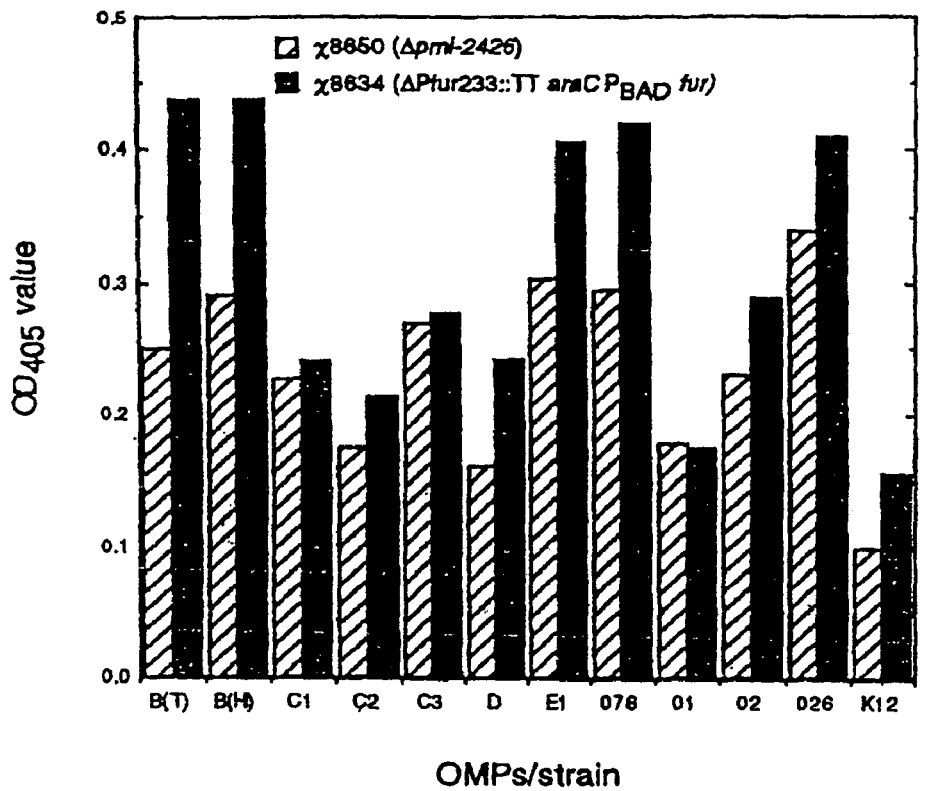
Figure 11. IgG Ab responses to OMPs isolated from *Salmonella* and *E. coli* strains.

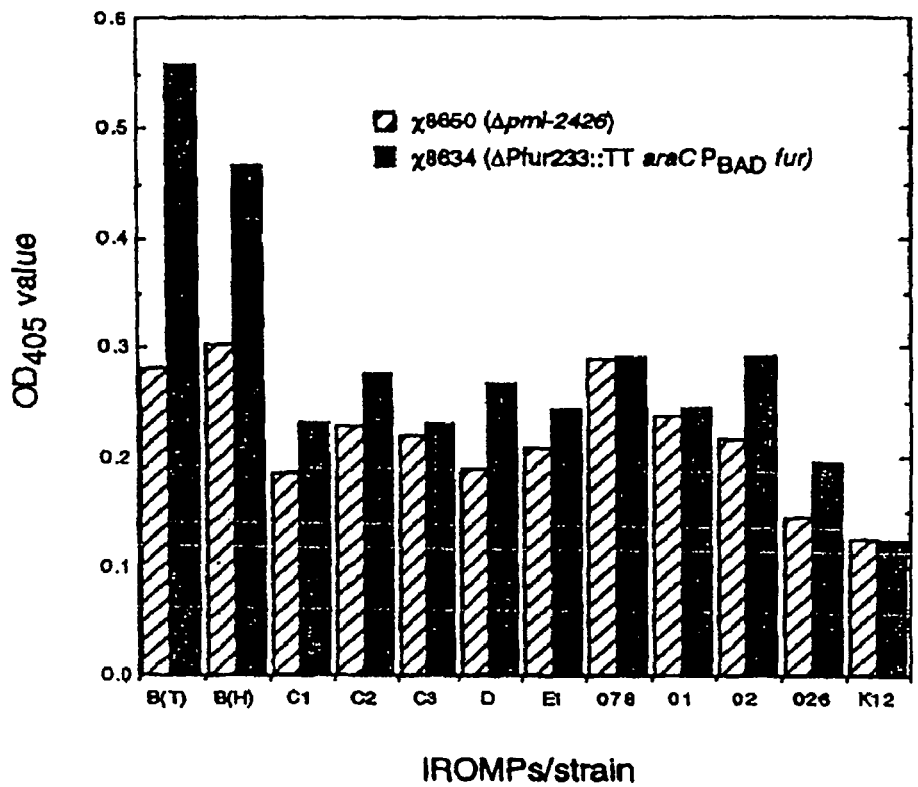
Figure 12. IgG Ab responses to IROMPs isolated from *Salmonella* and *E. coli* strains.

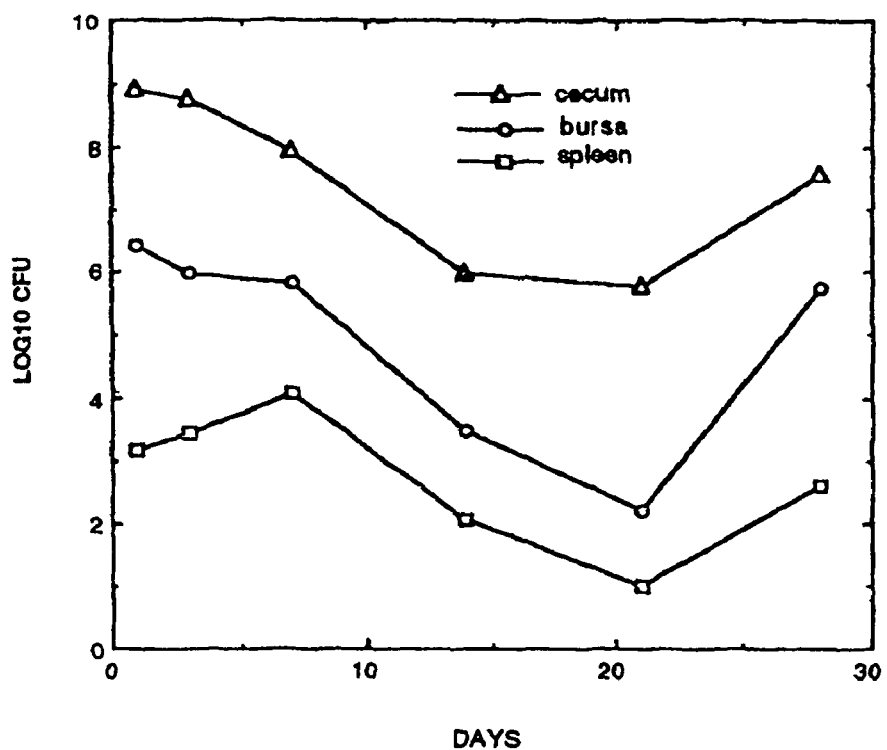
Figure 13. Colonization of day-of-hatch chicks with χ8754 (Δ*pmi-2426* ΔP*fur223*::TT *araC* P$_{BAD}$ *fur*) following oral inoculation.

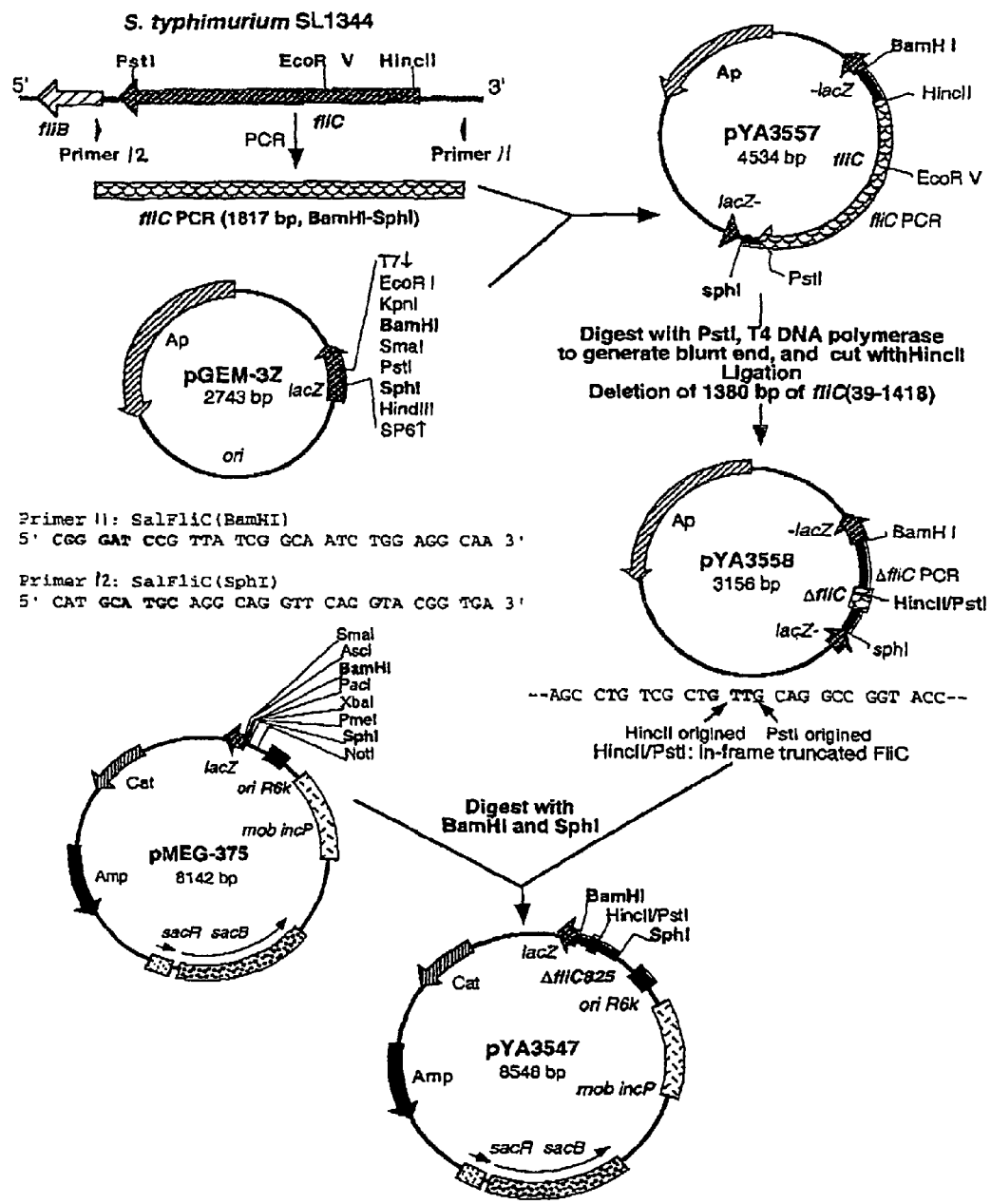
FIGURE 14. Construction f suicide vector for ΔfliC825

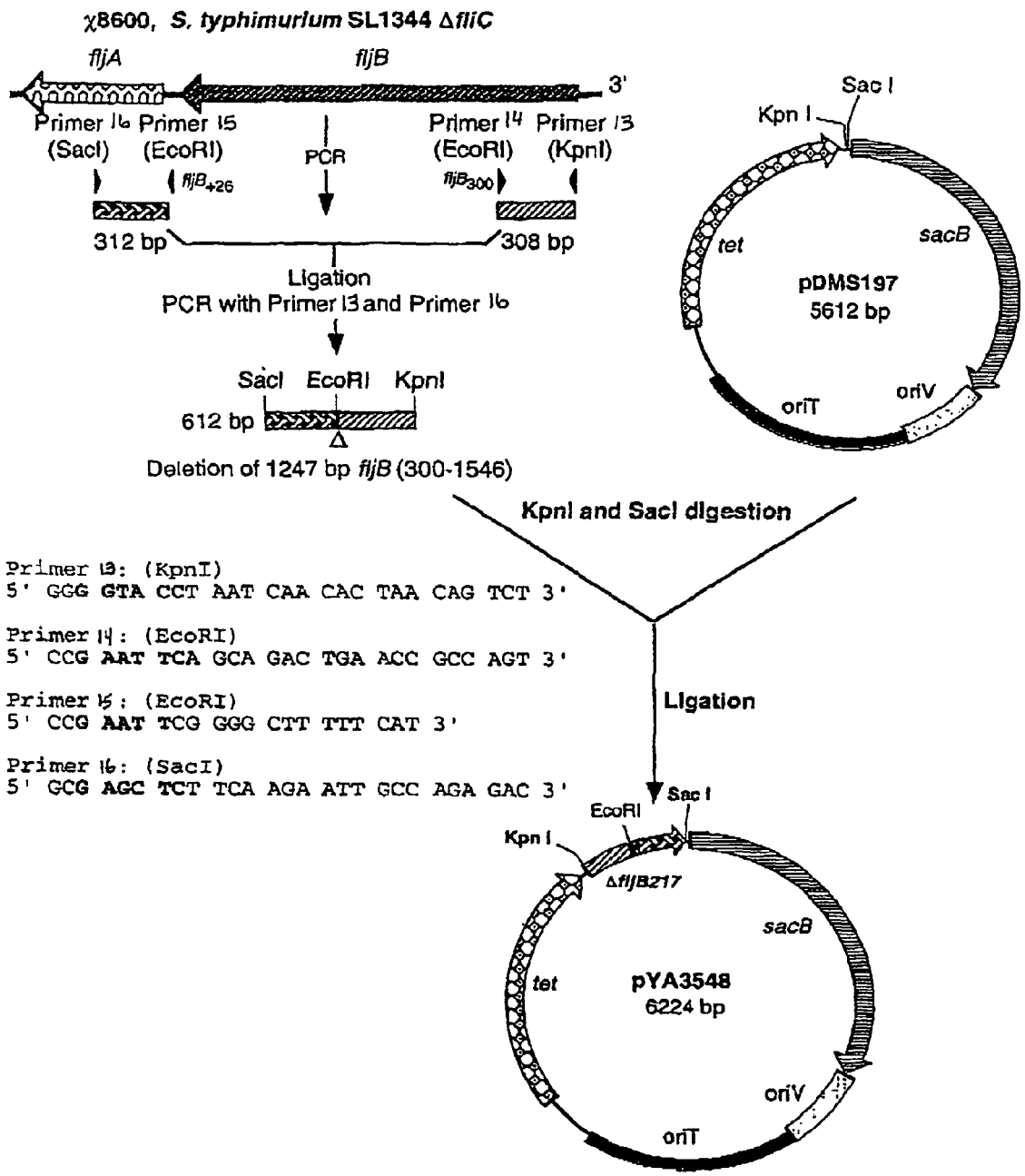
FIGURE 15. Construction of suicid vect r for ΔfljB217

FIGURE 16. *Salmonella typhimurium* SL1344 chromosomal deletions:
A. ΔfliC825
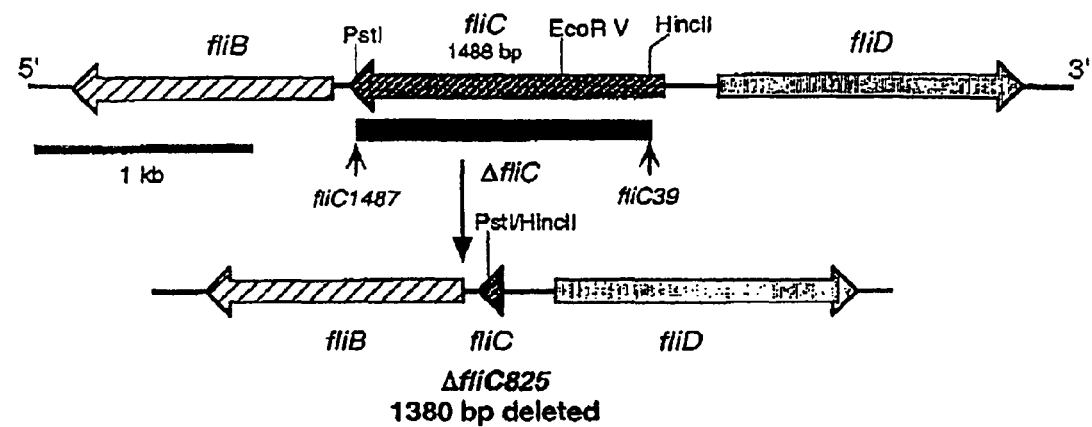
B. ΔfljB217
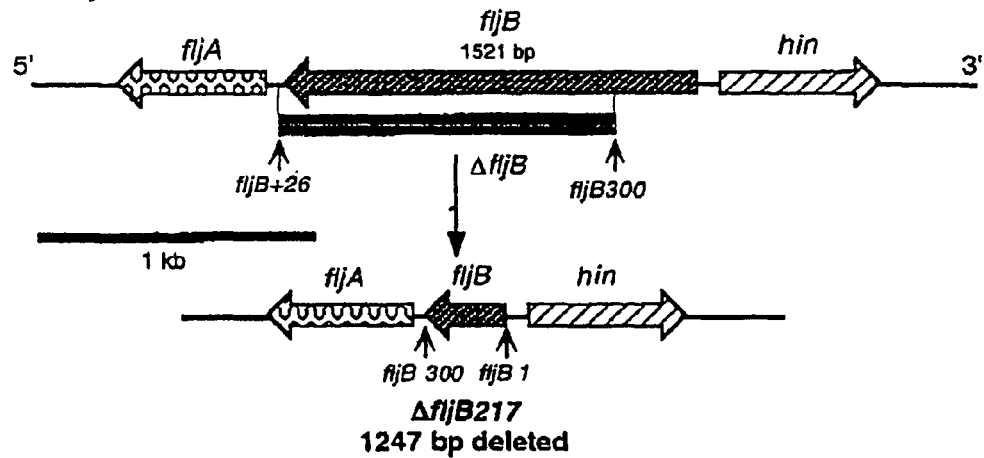

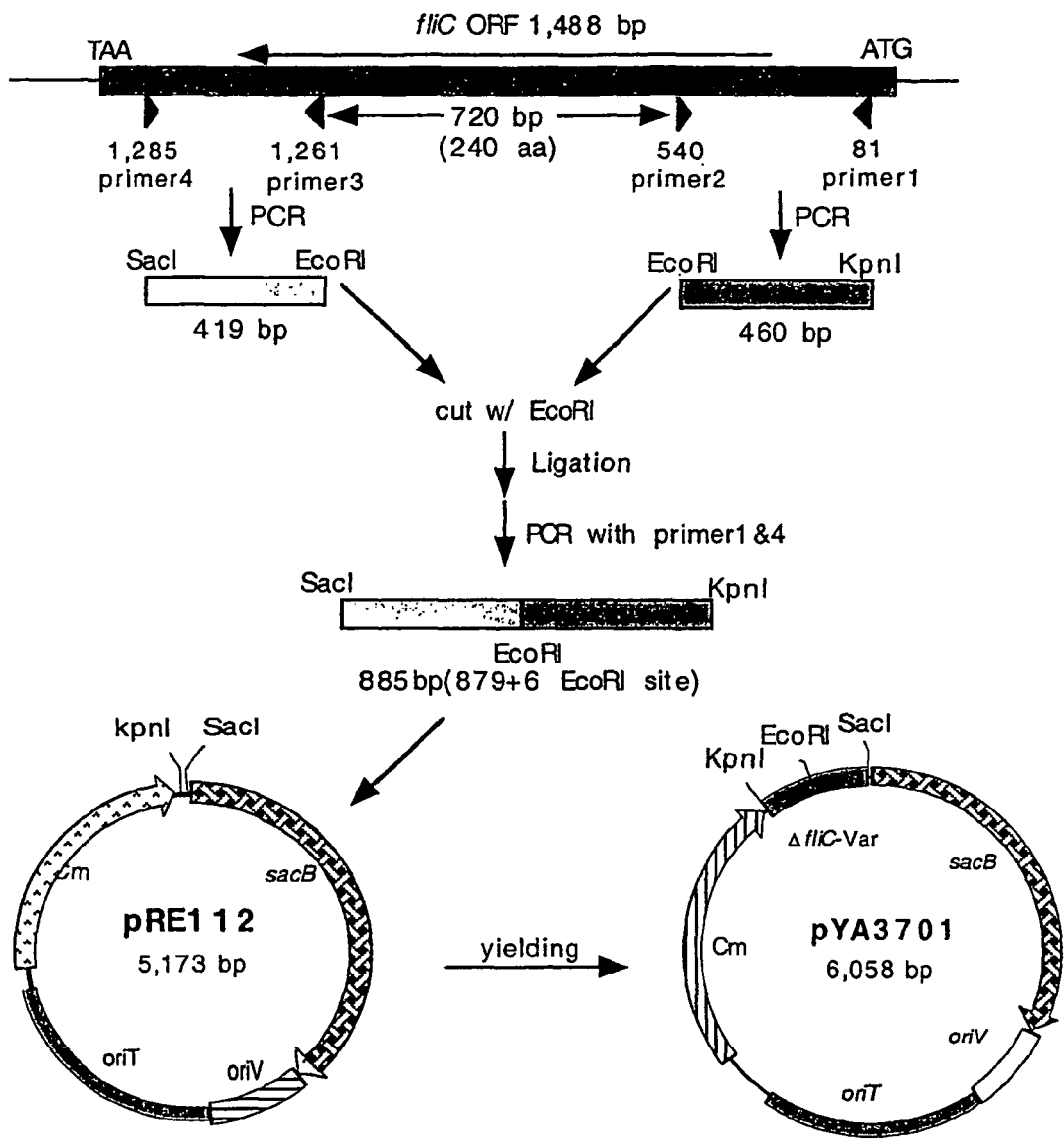
primer 1: delV.fliC 1 kpnI/bp81-104
5'-GGGGTACCCGCTATCGAGCGTCTGTCTTCCGG-3'
primer 2: delV fliC 2 EcoRI/bp540-516
5'-GGGAATTCCTTATATTTTTGTTGCACATTCAG-3'
primer 3: delV fliC 3 EcoRI/bp1261-1285
5'-GGGAATTCACGTTACGTTCTGACCTGGGTGCG-3'
primer 4: delV fliC 4 SacI/bp1679-1655
5'-GGGAGCTCCGTCTTATCCAGCGTGATTTTCCA-3'
Figure 17. Construction of a suicide vector for transfer of ΔfliC-Var mutation

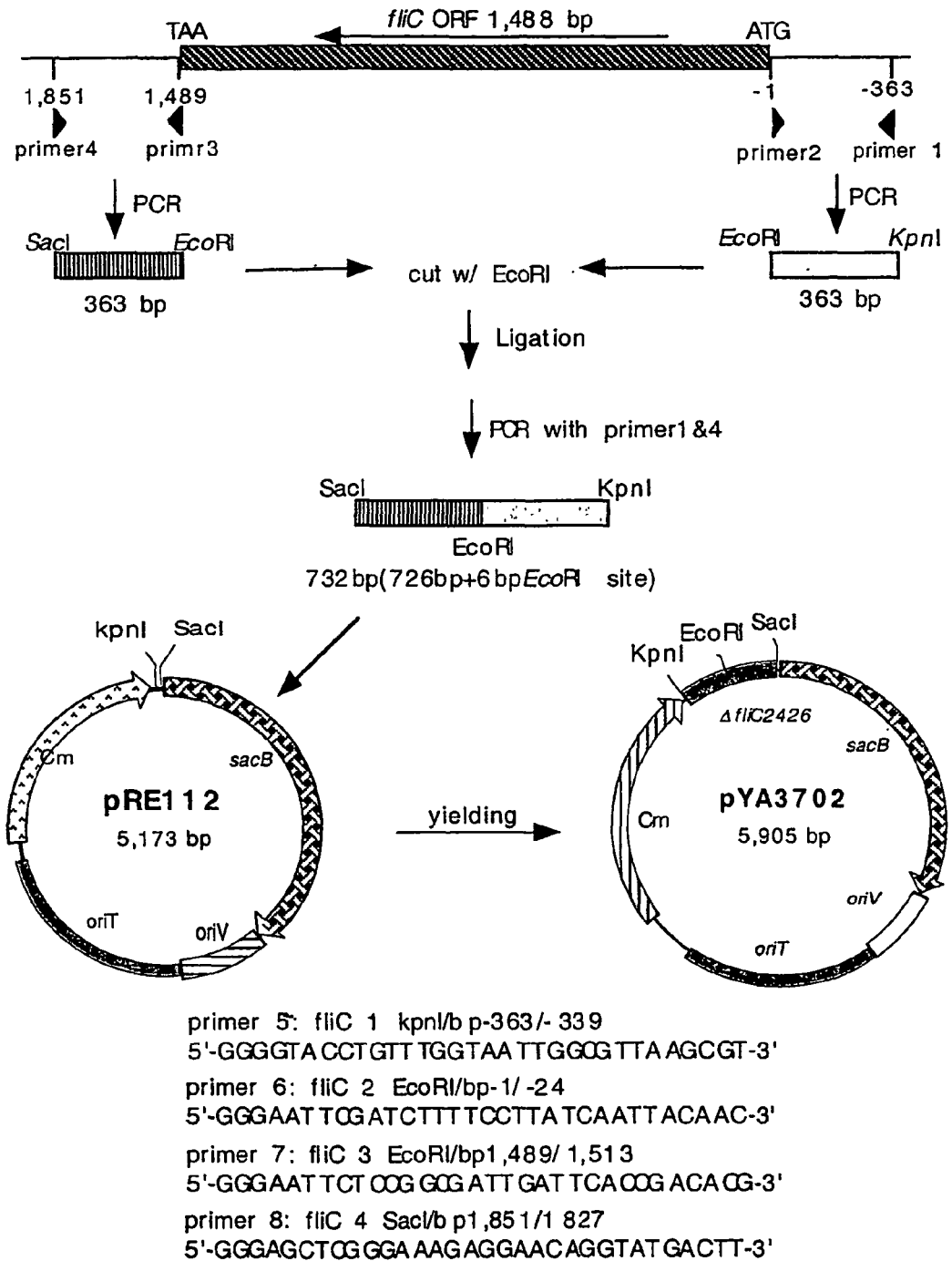
Figure 18. Construction of a suicide vector for transfer of ΔfliC 2426 mutation Figure 19. *S. typhimurium* UK-1 chromosomal map for Δ*fliC*-Var and Δ*fliC2426* deletion mutations.

A. Δ*fliC*-Var

*fliC* ORF 1,488 bp

TAA — 1,261 — 540 — ATG 720 bp deleted

Δ*fliC*

TAA — EcoRI — ATG 768 bp remains with an additional 6 bp *Eco*RI site

B. Δ*fliC2426*

*fliC* ORF 1,488 bp

TAA — ATG
*fliC1488* — *fliC1* entire FliC ORF (*fliC1* to *fliC1488*) deleted

Figure 20. DNA nucleotide sequrnce of improved araC* P<sub>BAD</sub> region in pYA3624.

```
                                                                                  araI₂
5'CCAA AAA AAC GGG TAT GGA GAA ACA GTA GAG AGT TGC GAT AAA AAG CGT CAG GTA GGA 3'
3'GGTT TTT TTG CCC ATA CCT CTT TGT CAT CTC TCA ACG CTA TTT TTC GCA GTC CAT CCT 5'
    ← araBAD mRNA +1              -10                                   -35
                          araI₁                           CRP binding site
TCC GCT AAT CTT ATG GAT AAA AAT GCT ATG GCA TAG CAA AGT GTG ACG CCG TGC AAA TAA
AGG CGA TTA GAA TAC CTA TTT TTA CGA TAC CGT ATC GTT TCA CAC TGC GGC ACG TTT ATT araO₁L                   -35    araO₁R                          -10
TCA ATG TGG ACT TTT CTG CCG TGA TTA TAG ACA CTT TTG TTA CGC GTT TTT GTC ATG GCT
AGT TAC ACC TGA AAA GAC GGC ACT AAT ATC TGT GAA AAC AAT GCG CAA AAA CAG TAC CGA +1 araC* mRNA →
TTG GTC CCG CTT TGT TAC AGA ATG CTT TTA ATA AGC GGG GTT ACC GGT TGG GTT AGC GAG
AAC CAG GGC GAA ACA ATG TCT TAC GAA AAT TAT TCG CCC CAA TGG CCA ACC CAA TCG CTC araO₂
AAG AGC CAG TAA AAG ACG CAG TGA CGG CAA TGT CTG ATG CAA TAT GGA CAA TTG GTT TCT
TTC TCG GTC ATT TTC TGC GTC ACT GCC GTT ACA GAC TAC GTT ATA CCT GTT AAC CAA AGA ↓ araC* starts
TCT CTG AAT GGT GGG AGT ATG AAA AGT ATG GCT GAA GCG CAA AAT GAT CCC CTG CTG CCG
                                         M   A   E   A   Q   N   D   P   L   L   P GGA TAC TCG TTT AAC GCC CAT CTG GTG GCG GGT TTA ACG CCG ATT GAG GCC AAC GGT TAT
 G   Y   S   F   N   A   H   L   V   A   G   L   T   P   I   E   A   N   G   Y CTC GAT TTT TTT ATC GAC CGA CCG CTG GGA ATG AAA GGT TAT ATT CTC AAT CTC ACC ATT
 L   D   F   F   I   D   R   P   L   G   M   K   G   Y   I   L   N   L   T   I CGC GGT CAG GGG GTG GTG AAA AAT CAG GGA CGA GAA TTT GTC TGC CGA CCG GGT GAT ATT
 R   G   Q   G   V   V   K   N   Q   G   R   E   F   V   C   R   P   G   D   I TTG CTG TTC CCG CCA GGA GAG ATT CAT CAC TAC GGT CGT CAT CCG GAG GCT CGC GAA TGG
 L   L   F   P   P   G   E   I   H   H   Y   G   R   H   P   E   A   R   E   W TAT CAC CAG TGG GTT TAC TTT CGT CCG CGC GCC TAC TGG CAT GAA TGG CTT AAC TGG CCG
 Y   H   Q   W   V   Y   F   R   P   R   A   Y   W   H   E   W   L   N   W   P TCA ATA TTT GCC AAT ACG GGT TTC TTT CGC CCG GAT GAA GCG CAC CAG CCG CAT TTC AGC
 S   I   F   A   N   T   G   F   F   R   P   D   E   A   H   Q   P   H   F   S GAC CTG TTT GGG CAA ATC ATT AAC GCC GGG CAA GGG GAA GGG CGC TAT TCG GAG CTG CTG
 D   L   F   G   Q   I   I   N   A   G   Q   G   E   G   R   Y   S   E   L   L GCG ATA AAT CTG CTT GAG CAA TTG TTA CTG CGG CGC ATG GAA GCG ATT AAC GAG TCG CTC
 A   I   N   L   L   E   Q   L   L   L   R   R   M   E   A   I   N   E   S   L CAT CCA CCG ATG GAT AAT CGG GTA CGC GAG GCT TGT CAG TAC ATC AGC GAT CAC CTG GCA
 H   P   P   M   D   N   R   V   R   E   A   C   Q   Y   I   S   D   H   L   A GAC AGC AAT TTT GAT ATC GCC AGC GTC GCA CAG CAT GTT TGC TTG TCG CCG TCG CGT CTG
 D   S   N   F   D   I   A   S   V   A   Q   H   V   C   L   S   P   S   R   L
```

Figure 20. (cont'd)

```
TCA CAT CTT TTC CGC CAG CAG TTA GGG ATT AGC GTC TTA AGC TGG CGC GAG GAC CAA CGC
 S   H   L   F   R   Q   Q   L   G   I   S   V   L   S   W   R   E   D   Q   R

ATT AGT CAG GCG AAG CTG CTT TTG AGC ACT ACC CGG ATG CCT ATC GCC ACC GTC GGT CGC
 I   S   Q   A   K   L   L   L   S   T   T   R   M   P   I   A   T   V   G   R

AAT GTT GGT TTT GAC GAT CAA CTC TAT TTC TCG CGA GTA TTT AAA AAA TGC ACC GGG GCC
 N   V   G   F   D   D   Q   L   Y   F   S   R   V   F   K   K   C   T   G   A

AGC CCG AGC GAG TTT CGT GCC GGT TGT GAA GAA AAA GTG AAT GAT GTA GCC GTC AAG TTG
 S   P   S   E   F   R   A   G   C   E   E   K   V   N   D   V   A   V   K   L

TCA TAA TTG GTA ACG AAT CAG ACA ATT GAC GGC
 S   *
    ←araC* ends
```

Figure 21. DNA and amino acid sequences of $P_{fur}$ and *fur* gene of *S. paratyphi* A.

```
fldA
181/61              primer              211/71
GAA GCG CAA TGT GAC TGG GAT GAC TTC TTC CCG ACT CTC GAA GAG ATT GAC TTT AAC GGT
 E   A   Q   C   D   W   D   D   F   F   P   T   L   E   E   I   D   F   N   G
241/81                                      271/91
AAG CTG GTG GCG CTG TTT GGC TGT GGC GAT CAG GAA GAC TAC GCG GAA TAC TTC TGT GAT
 K   L   V   A   L   F   G   C   G   D   Q   E   D   Y   A   E   Y   F   C   D
301/101                                     331/111
GCG CTG GGC ACG ATT CGC GAC ATT ATT GAG CCG CGC GGC GCC ACG ATT GTG GGT CAC TGG
 A   L   G   T   I   R   D   I   I   E   P   R   G   A   T   I   V   G   H   W
361/121                                     391/131
CCA ACT GCA GGC TAT CAT TTT GAA GCC TCT AAA GGT CTG GCT GAC GAC GAT CAT TTT GTC
 P   T   A   G   Y   H   F   E   A   S   K   G   L   A   D   D   D   H   F   V
421/141                                     451/151
GGT CTG GCG ATT GAC GAA GAC CGT CAG CCT GAA CTG ACC GCC GAG CGT GTT GAA AAA TGG
 G   L   A   I   D   E   D   R   Q   P   E   L   T   A   E   R   V   E   K   W
481/161                             511/171
GTT AAG CAA GTT TCG GCT GAA TTG CAC CTC GAC GAC ATC CTC AAC GCC TAA TCT TAT GCG
 V   K   Q   V   S   A   E   L   H   L   D   D   I   L   N   A   *  ↑fldA ends
541/181                        571/191
GCG CAG CGT TAT ATC TGC GCC GCA TCA ATA GAC AAG ACC AAT CAA AAT AAT TGC TAC AAA
       primer              └delete (fur₋₂₅₃)           OxyR binding site
601/201                                     631/211
TTT GTA ACT TTC GCA CCC ATC CCT GTA CAA TGT CCG GGT GTA ATC AGG TGG CGC CAG ATT 661/221                                     691/231             -35
TTG CAG GCA AAA CCA CAG TTT TAT TAA CAT CTG CGA GAG ACT TGC GGT TTT CAT TTC GGC
   CRP binding site 721/241          -10                751/251
ATG GCA GTC CTA TAA TGA TAC GCA TTA TCT TGA GTG CAA TTT CTG TCA CTT CTC TAA TGA
            Fur consensus
781/261         SD                  813/1
AGT GAA TCG TTT AGC AAC AGG ACA GAT TCC GC ATG ACT GAC AAC AAT ACC GCA TTA AAG
       delete (fur₋₁₅) ┘       primer    M   T   D   N   N   T   A   L   K
                                     fur starts ↑
840/10                                      873/21
AAG GCT GGC CTG AAA GTA ACG CTT CCT CGT TTA AAA ATT CTG GAA GTT CTT CAG GAA CCA
 K   A   G   L   K   V   T   L   P   R   L   K   I   L   E   V   L   Q   E   P
900/30                                      933/41
GAT AAC CAT CAC GTC AGT GCC GAA GAT TTA TAC AAA CGC CTG ATC GAC ATG GGT GAA GAA
 D   N   H   H   V   S   A   E   D   L   Y   K   R   L   I   D   M   G   E   E
960/50                                      993/61
ATC GGT CTG GCA ACC GTA TAC CGT GTG CTG AAC CAG TTT GAC GAT GCC GGT ATC GTG ACC
 I   G   L   A   T   V   Y   R   V   L   N   Q   F   D   D   A   G   I   V   T
1020/70                                     1053/81
CGC CAT AAT TTT GAA GGC GGT AAA TCC GTT TTT GAA CTG ACG CAA CAG CAT CAT CAC GAC
 R   H   N   F   E   G   G   K   S   V   F   E   L   T   Q   Q   H   H   H   D
1080/90       primer                 1113/101
CAT CTT ATC TGC CTT GAT TGC GGA AAA GTG ATT GAA TTT AGT GAT GAC TCT ATT GAA GCG
 H   L   I   C   L   D   C   G   K   V   I   E   F   S   D   D   S   I   E   A
1140/110                                    1173/121
CGC CAG CGT GAA ATT GCG GCG AAA CAC GGT ATT CGT TTA ACT AAT CAC AGC CTC TAT CTT
 R   Q   R   E   I   A   A   K   H   G   I   R   L   T   N   H   S   L   Y   L
1200/130                                    1233/141
TAC GGC CAC TGC GCT GAA GGC GAC TGC CGC GAA GAC GAG CAC GCG CAC GAT GAC GCG ACT
 Y   G   H   C   A   E   G   D   C   R   E   D   E   H   A   H   D   D   A   T
1260/150
AAA TAA
 K   *  fur ends
```

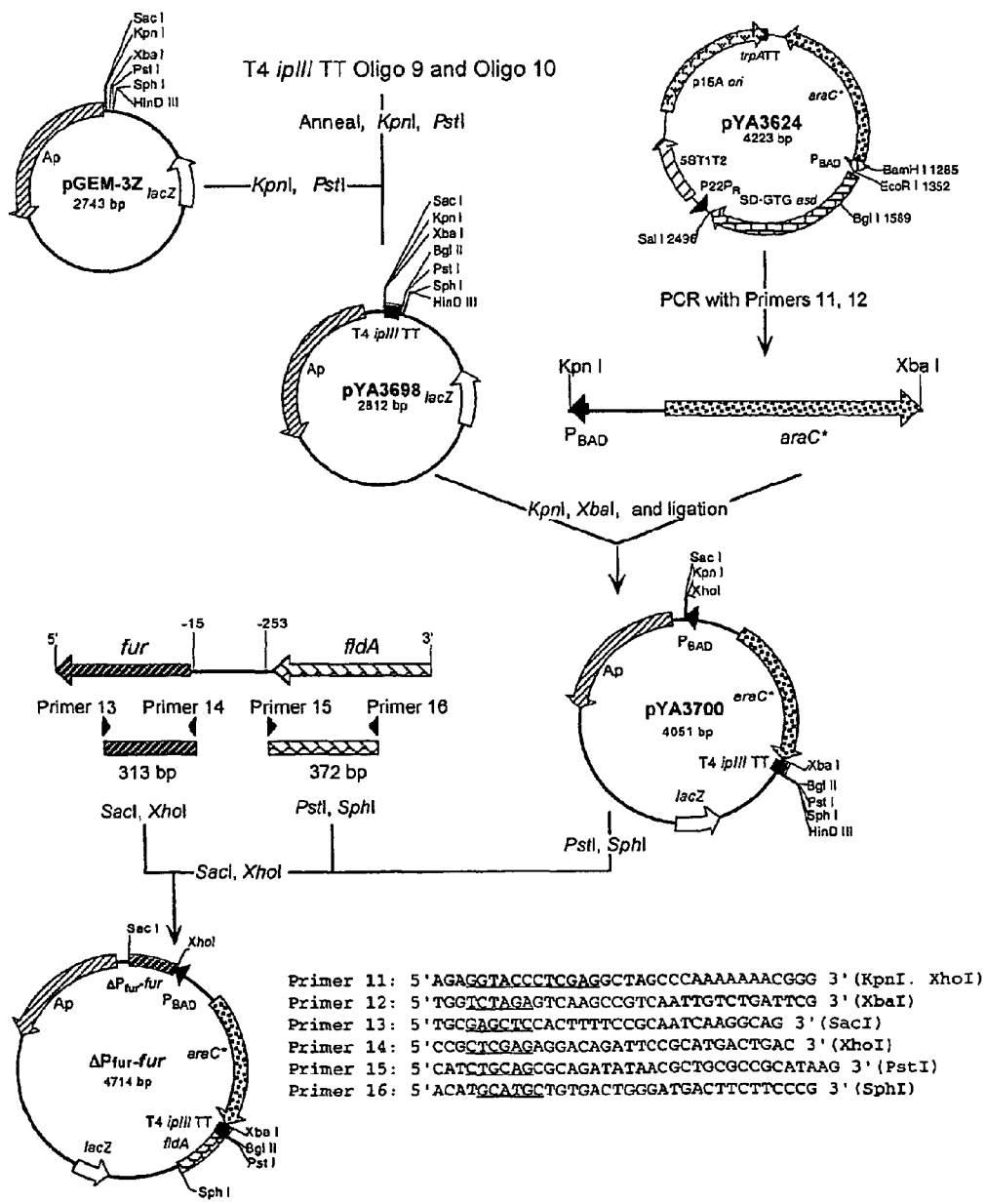
Figur 22. Construction of the suicide vector to introduce new ΔP$_{fur}$-33::TT araC P$_{BAD}$ fur deletion-insertion mutation.

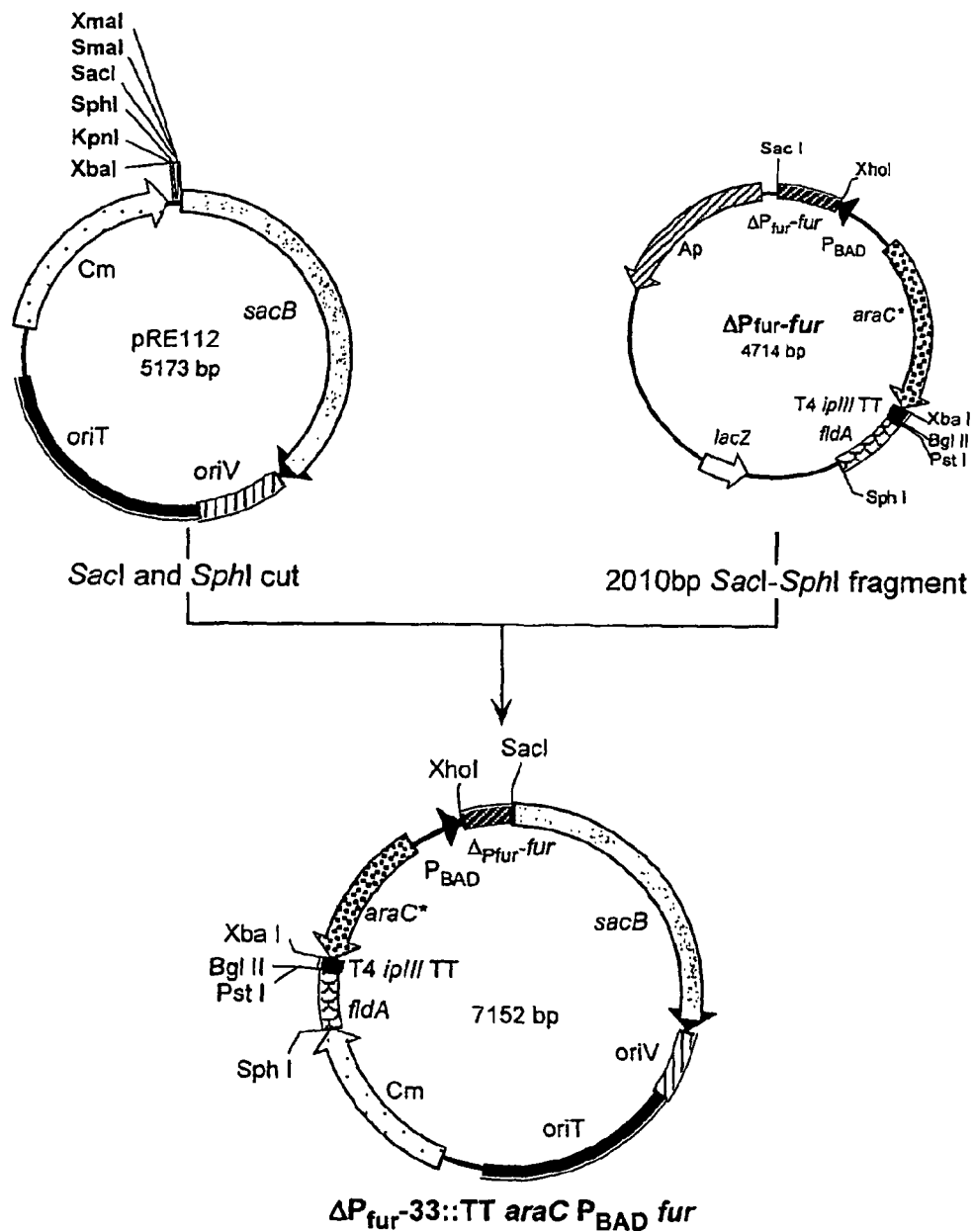
Figur 22. (cont'd)

Figure 23. Chromosomal map of ΔP$_{fur}$-33::TT araC P$_{BAD}$ fur d letion-insertion mutation.
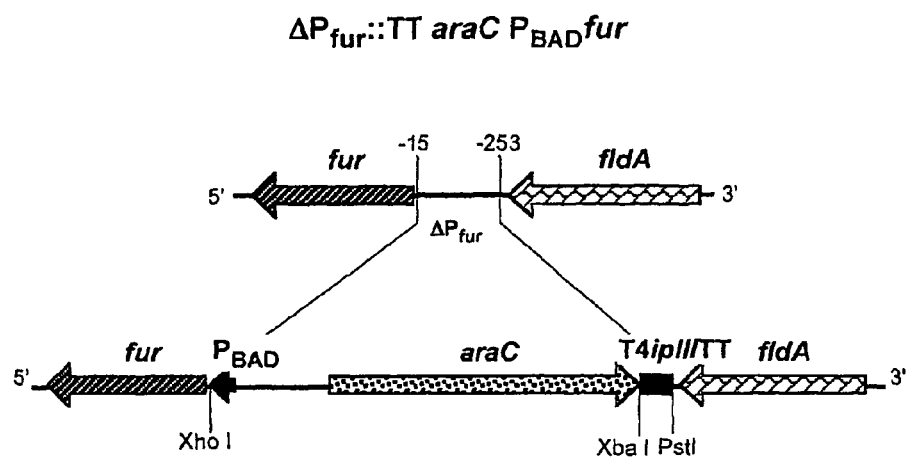
fur promoter region (-15 to -253; including Fur consensus, CRP binding, and OxyR binding sites) deleted and 1344 bp P$_{BAD}$ araC TT inserted.

Figure 24. DNA sequence of the ΔP$_{fur}$-33::TT araC* P$_{BAD}$ fur.

```
fldA
 R   Q   P   E   L   T   A   E   R   V   E   K   W   V   K   Q   V   S   A   E
CGT CAG CCT GAA CTG ACC GCC GAG CGT GTT GAA AAA TGG GTT AAG CAA GTT TCG GCT GAA L   H   L   D   D   I   L   N   A   *   S   Y   A   A   Q   R   Y   I   C   A
TTG CAC CTC GAC GAC ATC CTC AAC GCC TAA TCT TAT GCG GCG CAG CGT TAT ATC TGC GCT
                                 ←fldA ends                                fur₋₂₅₄
PstI
GCA GAG ATC TTT TAT TAT TCT ATC CTA GAA TTG TGA TAA TAT ATT CAC AAT TCT AGG AGT
                                         T4 ipIII transcription terminator sequence
                                 XbaI
TGT AAA CTG CTT TTA TTT ATC TAG AGT CAA GCC GTC AAT TGT CTG ATT CGT TAC CAA TTA
ACA TTT GAC GAA AAT AAA TAG ATC TCA GTT CGG CAG TTA ACA GAC TAA GCA ATG GTT AAT
                                                                               *
                                                                      araC ends →

TGA CAA CTT GAC GGC TAC ATC ATT CAC TTT TTC TTC ACA ACC GGC ACG GAA CTC GCT CGG
ACT GTT GAA CTG CCG ATG TAG TAA GTG AAA AAG AAG TGT TGG CCG TGC CTT GAG CGA GCC
 S   L   K   V   A   V   D   N   V   K   E   E   C   G   A   R   F   E   S   P

GCT GGC CCC GGT GCA TTT TTT AAA TAC CCG CGA GAA ATA GAG TTG ATC GTC AAA ACC AAC
CGA CCG GGG CCA CGT AAA AAA TTT ATG GGC GCT CTT TAT CTC AAC TAG CAG TTT TGG TTG
 S   A   G   T   C   K   K   F   V   R   S   F   Y   L   Q   D   D   F   G   V

ATT GCG ACC GAC GGT GGC GAT AGG CAT CCG GGT GGT GCT CAA AAG CAG CTT CGC CTG GCT
TAA CGC TGG CTG CCA CCG CTA TCC GTA GGC CCA CCA CGA GTT TTC GTC GAA GCG GAC CGA
 N   R   G   V   T   A   I   P   M   R   T   T   S   L   L   K   A   Q   S

GAT ACG TTG GTC CTC GCG CCA GCT TAA GAC GCT AAT CCC TAA CTG CTG GCG GAA AAG ATG
CTA TGC AAC CAG GAG CGC GGT CGA ATT CTG CGA TTA GGG ATT GAC GAC CGC CTT TTC TAC
 I   R   Q   D   E   R   W   S   L   V   S   I   G   L   Q   Q   R   F   L   H

TGA CAG ACG CGA CGG CGA CAA GCA AAC ATG CTG TGC GAC GCT GGC GAT ATC AAA ATT GCT
ACT GTC TGC GCT GCC GCT GTT CGT TTG TAC GAC ACG CTG CGA CCG CTA TAG TTT TAA CGA
 S   L   R   S   P   S   L   C   V   H   Q   A   V   S   A   I   D   F   N   S

GTC TGC CAG GTG ATC GCT GAT GTA CTG ACA AGC CTC GCG TAC CCG ATT ATC CAT CGG TGG
CAG ACG GTC CAC TAG CGA CTA CAT GAC TGT TCG GAG CGC ATG GGC TAA TAG GTA GCC ACC
 D   A   L   H   D   S   I   Y   Q   C   A   E   R   V   R   N   D   M   P   P

ATG GAG CGA CTC GTT AAT CGC TTC CAT GCG CCG CAG TAA CAA TTG CTC AAG CAG ATT TAT
TAC CTC GCT GAG CAA TTA GCG AAG GTA CGC GGC GTC ATT GTT AAC GAG TTC GTC TAA ATA
 H   L   S   E   N   I   A   E   M   R   R   L   L   L   Q   E   L   L   N   I

CGC CAG CAG CTC CGA ATA GCG CCC TTC CCC TTG CCC GGC GTT AAT GAT TTG CCC AAA CAG
GCG GTC GTC GAG GCT TAT CGC GGG AAG GGG AAC GGG CCG CAA TTA CTA AAC GGG TTT GTC
 A   L   L   E   S   Y   R   G   E   G   Q   G   A   N   I   I   Q   G   F   L

GTC GCT GAA ATG CGG CTG GTG CGC TTC ATC GGC GCG AAA GAA CCC CGT ATT GGC AAA TAT
CAG CGA CTT TAC GCC GAC CAC GCG AAG TAG CCG CGC TTT CTT GGG GCA TAA CCG TTT ATA
 D   S   F   H   P   Q   H   A   E   D   P   R   F   F   G   T   N   A   F   I

TGA CGG CCA GTT AAG CCA TTC ATG CCA GTA GGC GCG CGG ACG AAA GTA AAC CCA CTG GTG
ACT GCC GGT CAA TTC GGT AAG TAC GGT CAT CCG CGC GCC TGC TTT CAT TTG GGT GAC CAC
 S   P   W   N   L   W   E   H   W   Y   A   R   P   R   F   Y   V   W   Q   H
```

Figure 24. (cont'd)

```
ATA CCA TTC GCG AGC CTC CGG ATG ACG ACC GTA GTG ATG AAT CTC TCC TGG CGG GAA CAG
TAT GGT AAG CGC TCG GAG GCC TAC TGC TGG CAT CAC TAC TTA GAG AGG ACC GCC CTT GTC
 Y   W   E   R   A   E   P   H   R   G   Y   H   H   I   E   G   P   P   F   L

CAA AAT ATC ACC CGG TCG GCA AAC AAA TTC TCG TCC CTG ATT TTT CAC CAC CCC CTG ACC
GTT TTA TAG TGG GCC AGC CGT TTG TTT AAG AGC AGG GAC TAA AAA GTG GTG GGG GAC TGG
 L   I   D   G   P   R   C   V   F   E   R   G   Q   N   K   V   V   G   Q   G

GCG AAT GGT GAG ATT GAG AAT ATA ACC TTT CAT TCC CAG CGG TCG GTC GAT AAA AAA ATC
CGC TTA CCA CTC TAA CTC TTA TAT TGG AAA GTA AGG GTC GCC AGC CAG CTA TTT TTT TAG
 R   I   T   L   N   L   I   Y   G   K   M   G   L   P   R   D   I   F   F   D

GAG ATA ACC GTT GGC CTC AAT CGG CGT TAA ACC CGC CAC CAG ATG GGC ATT AAA CGA GTA
CTC TAT TGG CAA CCG GAG TTA GCC GCA ATT TGG GCG GTG GTC TAC CCG TAA TTT GCT CAT
 L   Y   G   N   A   E   I   P   T   L   G   A   V   L   H   A   N   F   S   Y

TCC CGG CAG CAG GGG ATC ATT TTG CGC TTC AGC CAT ACT TTT CAT ACT CCC GCC ATT CAG
AGG GCC GTC GTC CCC TAG TAA AAC GCG AAG TCG GTA TGA AAA GTA TGA GGG CGG TAA GTC
 G   P   L   L   P   D   N   Q   A   E   A   M
                                          ← araC starts AGA AGA AAC CAA TTG TCC ATA TTG CAT CAG ACA TTG CCG TCA CTG CGT CTT TTA CTG GCT
TCT TCT TTG GTT AAC AGG TAT AAC GTA GTC TGT AAC GGC AGT GAC GCA GAA AAT GAC CGA
        araO₂

CTT CTC GCT AAC CAA ACC GGT AAC CCC GCT TAT TAA AAG CAT TCT GTA ACA AAG CGG GAC
GAA GAG CGA TTG GTT TGG CCA TTG GGG CGA ATA ATT TTC GTA AGA CAT TGT TTC GCC CTG

CAA AGC CAT GAC AAA AAC GCG TAA CAA AAG TGT CTA TAA TCA CGG CAG AAA AGT CCA CAT
GTT TCG GTA CTG TTT TTG CGC ATT GTT TTC ACA GAT ATT AGT GCC GTC TTT TCA GGT GTA
+1araC mRNA  -10              araO₁R      -35                 araO₁L TGA TTA TTT GCA CGG CGT CAC ACT TTG CTA TGC CAT AGC ATT TTT ATC CAT AAG ATT AGC
ACT AAT AAA CGT GCC GCA GTG TGA AAC GAT ACG GTA TCG TAA AAA TAG GTA TTC TAA TCG
    CRP binding site                              araI₁
           -35                           -10             +1 araBAD mRNA
GGA TCC TAC CTG ACG CTT TTT ATC GCA ACT CTC TAC TGT TTC TCC ATA CCC GTT TTT TTG
CCT AGG ATG GAC TGC GAA AAA TAG CGT TGA GAG ATG ACA AAG AGG TAT GGG CAA AAA AAC
    araI₂
         XhoI    ↓fur₋₁₄             M   T   D   N   N   T   A   L   K   K   A
GGC TAG CCT CGA GAG GAC AGA TTC GCG ATG ACT GAC AAC AAT ACC GCA TTA AAG AAG GCT
CCG ATC GGA GCT CTC CTG TCT AAG CGC TAC TGA CTG TTG TTA TGG CGT AAT TTC TTC CGA G   L   K   V   T   L   P   R   L   K   I   L   E   V   L   Q   E   P   D   N
GGC CTG AAA GTA ACG CTT CCT CGT TTA AAA ATT CTG GAA GTT CTT CAG GAA CCA GAT AAC
CCG GAC TTT CAT TGC GAA GGA GCA AAT TTT TAA GAC CTT CAA GAA GTC CTT GGT CTA TTG H   H   V   S   A   E   D   L   Y   K   R   L   I   D   M   G   E   E   I   G
CAT CAC GTC AGT GCG GAA GAT TTA TAC AAA CGC CTG ATC GAC ATG GGT GAA GAA ATC GGT
GTA GTG CAG TCA CGC CTT CTA AAT ATG TTT GCG GAC TAG CTG TAC CCA CTT CTT TAG CCA L   A   T   V   Y   R   V   L   N   Q   F   D   D   A   G   I   V   T   R   H
CTG GCA ACC GTA TAC CGT GTG CTG AAC CAG TTT GAC GAT GCC GGT ATC GTG ACC CGC CAT
GAC CGT TGG CAT ATG GCA CAC GAC TTG GTC AAA CTG CTA CGG CCA TAG CAC TGG GCG GTA
```

Figure 24. (cont'd)

```
N   F   E   G   G   K   S   V   F   E   L   T   Q   Q   H   H   H   D   H   L
AAT TTT GAA GGC GGT AAA TCC GTT TTT GAA CTG ACG CAA CAG CAT CAT CAC GAC CAT CTT
TTA AAA CTT CCG CCA TTT AGG CAA AAA CTT GAC TGC GTT GTC GTA GTA GTG CTG GTA GAA

I   C   L   D   C   G   K   V   I   E   F   S   D   D   S   I   E   A   R   Q
ATC TGC CTT GAT TGC GGA AAA GTG ATT GAA TTT AGT GAT GAC TCT ATT GAA GCG CGC CAG
TAG ACG GAA CTA ACG CCT TTT CAC TAA CTT AAA TCA CTA CTG AGA TAA CTT CGC GCG GTC

R   E   I   A   A   K   H   G   I   R   L   T   N   H   S   L   Y   L   Y   G
CGT GAA ATT GCG GCG AAA CAC GGT ATT CGT TTA ACT AAT CAC AGC CTC TAT CTT TAC GGC
GCA CTT TAA CGC CGC TTT GTG CCA TAA GCA AAT TGA TTA GTG TCG GAG ATA GAA ATG CCG

←fur ends
H   C   A   E   G   D   C   R   E   D   E   H   A   H   D   D   A   T   K   *
CAC TGC GCT GAA GGC GAC TGC CGC GAA GAC GAG CAC GCG CAC GAT GAC GCG ACT AAA TAA
GTG ACG CGA CTT CCG CTG ACG GCG CTT CTG CTC GTG CGC GTG CTA CTG CGC TGA TTT ATT
```

Figure 25. DNA and amino acid sequences of P_rpoS, *rpoS* and flanking region of *S. typhimurium* and *S. typhi*.

```
STM: S. typhimurium 14028S
STY: S. typhi CT18

AAT GCA AGC AGT ACG TCA ACC AGC GCG CCG ATT TCC GCA TGG CGC TGG CCG ACG GAT GGC-STM
AAT GCA AGC AGT ACG TCA ACC AGC GCG CCG ATT TCC GCA TGG CGC TGG CCG ACG GAT GGC-STY
 N   A   S   S   T   S   T   S   A   P   I   S   A   W   R   W   P   T   D   G

AAA GTG ATC GAA AAC TTT GGC GCT TCC GAA GGG GGC AAT AAA GGG ATC GAC ATT GCA GGC
AAA GTG ATC GAA AAC TTT GGC GCT TCC GAA GGG GGC AAT AAA GGG ATC GAC ATT GCA GGC
 K   V   I   E   N   F   G   A   S   E   G   G   N   K   G   I   D   I   A   G

AGT AAG GGA CAG GCT ATC GTC GCA ACC GCT GAT GGG CGC GTC GTA TAT GCC GGT AAC GCA
AGT AAG GGA CAG GCT ATC GTC GCA ACC GCT GAT GGG CGC GTC GTA TAT GCC GGT AAC GCA
 S   K   G   Q   A   I   V   A   T   A   D   G   R   V   V   Y   A   G   N   A

CTG CGT GGT TAC GGT AAT CTT ATT ATC ATC AAA CAT AAC GAT GAT TAC CTG AGT GCC TAC
CTG CGT GGT TAC GGT AAT CTT ATT ATC ATC AAA CAT AAC GAT GAT TAC CTG AGT GCC TAC
 L   R   G   Y   G   N   L   I   I   I   K   H   N   D   D   Y   L   S   A   Y

GCC CAT AAT GAT ACG ATG CTG GTC CGG GAA CAA CAG GAA GTT AAG GCG GGG CAA AAA ATC
GCC CAT AAT GAT ACG ATG CTG GTC CGG GAA CAA CAG GAA GTT AAG GCG GGG CAA AAA ATC
 A   H   N   D   T   M   L   V   R   E   Q   Q   E   V   K   A   G   Q   K   I

GCT ACT ATG GGT AGC ACC GGC ACC AGC TCT ACA CGC TTG CAT TTT GAA ATT CGT TAC AAG
GCT ACT ATG GGT AGC ACC GGC ACC AGC TCT ACA CGC TTG CAT TTT GAA ATT CGT TAC AAG
 A   T   M   G   S   T   G   T   S   S   T   R   L   H   F   E   I   R   Y   K

GGG AAA TCC GTA AAC CCG CTG CGT TAT TTA CCG CAG CGA TAA AG
GGG AAA TCC GTA AAC CCG CTG CGT TAT TTA CCG CAG CGA TAA AG
 G   K   S   V   N   P   L   R   Y   L   P   Q   R   *
                                           ← nlpD ends
                                                         SD
CGG CGG AAC CAG GCT TTG ACT TGC TAG TTC CGT CAA GGG ATC ACG GGT AGG AGC CAC CTT
CGG CGG AAC CAG GCT TTG ACT TGC TAG TTC CGT CAA GGG ATC ACG GGT AGG AGC CAC CTT
                  ↑                                         ↑
                  T
         rpoS_-48    ΔP_rpoS (rpoS-48 to -13 deleted)    rpoS_-13

1185/1                                    1215/11
ATG AGT CAG AAT ACG CTG AAA GTT CAT GAT TTA AAT GAA GAC GCG GAA TTT GAT GAG AAC-STM
ATG AGT CAG AAT ACG CTG AAA GTT CAT GAT TTA AAT GAA GAC GCG GAA TTT GAT GAG AAC-STY
 M   S   Q   N   T   L   K   V   H   D   L   N   E   D   A   E   F   D   E   N
rpoS starts →

1245/21                                    1275/31
GGA GTA GAG GCT TTT GAC GAA AAA GCC TTG AGT GAA GAG GAA CCC AGT GAT AAC GAC CTG
GGA GTA GAG GCT TTT GAC GAA AAA GCC TTG AGT GAA GAG GAA CCC AGT GAT AAC GAC CTG
 G   V   E   A   F   D   E   K   A   L   S   E   E   P   S   D   N   D   L
1305/41                                    1335/51
GCT GAA GAA GAG CTG TTA TCG CAA GGG GCC ACA CAG CGT GTG TTG GAC GCG ACT CAG CTT
GCT GAA GAA GAG CTG TTA TCG CAA GGG GCC ACA CAG CGT GTG TTG GAC GCG ACT CAG CTT
 A   E   E   E   L   L   S   Q   G   A   T   Q   R   V   L   D   A   T   Q   L
1365/61                                    1395/71
TAC CTT GGT GAG ATT GGG TAT TCA CCA CTG TTA ACA GCC GAA GAA GAA GTC TAT TTT GCG
TAC CTT GGT GAG ATT GGG TAT TCA CCA CTG TTA ACA GCC GAA GAA GAA GTC TAT TTT GCG
 Y   L   G   E   I   G   Y   S   P   L   L   T   A   E   E   E   V   Y   F   A
1425/81                                    1455/91
CGT CGC GAC CTG CGT GGA GAT GTC GCT TCT CGC CGT CGC ATG ATT GAG AGT AAC CTG CGT
CGT CGC GCA CTG CGT GGA GAT GTC GCT TCT CGC CGT CGC ATG ATT GAG AGT AAC CTG CGT
 R   R   A   L   R   G   D   V   A   S   R   R   R   M   I   E   S   N   L   R
1485/101                                   1515/111
CTG GTG GTA AAA ATT GCC CGC CGT TAT GGC AAT CGT GGA CTG GCG TTG CTG GAC CTG ATT
CTG GTG GTA AAA ATT GCC CGC CGT TAT GGC AAT CGT GGA CTG GCG TTG CTG GAC CTG ATT
 L   V   V   K   I   A   R   R   Y   G   N   R   G   L   A   L   L   D   L   I
```

Figure 25. (cont'd)

```
1545/121                                          1575/131
GAA GAG GGC AAC CTG GGG CTT ATC CGT GCA GTA GAG AAG TTT GAC CCG GAA CGC GGG TTC
GAA GAG GGC AAC CTG GGG CTT ATC CGT GCA GTC GAG AAG TTT GAC CCG GAA CGC GGG TTC
 E   E   G   N   L   G   L   I   R   A   V   E   K   F   D   P   E   R   G   F
1605/141                                          1635/151
CGC TTC TCA ACA TAC GCA ACC TGG TGG ATT CGC CAG ACA ATC GAA CGG GCG ATC ATG AAC
CGC TTC TCA ACA TAC GCA ACC TGG TGG ATT CGC CAG ACA ATC GAA CGG GCG ATT ATG AAC
 R   F   S   T   Y   A   T   W   W   I   R   Q   T   I   E   R   A   I   M   N
1665/161                                          1695/171
CAA ACC CGT ACG ATT CGC TTG CCG ATT CAC ATT GTT AAA GAG CTG AAC GTA TAC CTG CGC
CAA ACC CGT ACG ATT CGC TTG CCG ATT CAC ATT GTT AAA GAG CTG AAC GTA TAC CTG CGC
 Q   T   R   T   I   R   L   P   I   H   I   V   K   E   L   N   V   Y   L   R
1725/181                                          1755/191
ACC GCA CGT GAG TTG TCG CAT AAA CTG GAC CAC GAA CCG AGT GCG GAA GAA ATT GCA GAG
ACC GCA CGT GAG TTG TCG CAT AAA CTG GAC CAC GAA CCG AGT GCG GAA GAA ATT GCA GAG
 T   A   R   E   L   S   H   K   L   D   H   E   P   S   A   E   E   I   A   E
1785/201                                          1815/211
CAA CTG GAT AAA CCG GTT GAT GAC GTC AGC CGT ATG CTT CGT CTC AAC GAG CGC ATT ACC
CAA CTG GAT AAA CCG GTT GAT GAC GTC AGC CGT ATG CTT CGT CTC AAC GAG CGC ATT ACC
 Q   L   D   K   P   V   D   D   V   S   R   M   L   R   L   N   E   R   I   T
1845/221                                          1875/231
TCG GTA GAC ACC CCG CTG GGC GGT GAT TCC GAA AAA GCG TTG CTG GAC ATC CTG GCC GAT
TCG GTA GAC ACC CCG CTG GGC GGT GAT TCC GAA AAA GCG TTG CTG GAC ATC CTG GCC GAT
 S   V   D   T   P   L   G   G   D   S   E   K   A   L   L   D   I   L   A   D
1905/241                                          1935/251
GAA AAA GAG AAC GGT CCG GAA GAC ACC ACG CAA GAT GAC GAT ATG AAA CAG AGC ATC GTC
GAA AAA GAG AAC GGT CCG GAA GAC ACC ACG CAA GAT GAC GAT ATG AAA CAG AGC ATC GTC
 E   K   E   N   G   P   E   D   T   T   Q   D   D   D   M   K   Q   S   I   V
1965/261                                          1995/271
AAA TGG TTG TTC GAA CTG AAC GCC AAA CAG CGT GAA GTG CTG GCG CGC CGT TTC GGT CTG
AAA TGG TTG TTC GAA CTG AAC GCC AAA CAG CGT GAA GTG CTG GCG CGC CGT TTC GGT CTG
 K   W   L   F   E   L   N   A   K   Q   R   E   V   L   A   R   R   F   G   L
2025/281                                          2055/291
CTG GGA TAT GAA GCT GCG ACA CTG GAA GAT GTA GGC CGT GAA ATC GGT CTT ACG CGT GAA
CTG GGA TAT GAA GCT GCG ACA CTG GAA GAT GTA GGC CGT GAA ATC GGT CTT ACG CGT GAA
 L   G   Y   E   A   A   T   L   E   D   V   G   R   E   I   G   L   T   R   E
2085/301                                          2115/311
CGT GTT CGT CAG ATT CAG GTT GAA GGC CTG CGC CGT CTG CGC GAA ATT CTG CAG ACG CAG
CGT GTT CGT CAG ATT CAG GTT GAA GGC CTG CGC CGT CTG CGC GAA ATT CTG CAG ACG CAG
 R   V   R   Q   I   Q   V   E   G   L   R   R   L   R   E   I   L   Q   T   Q
2145/321                                          2175/331
GGG CTG AAT ATC GAA GCG CTG TTC CGC GAG TAA GTA CCC TTG TCA
GGG CTG AAT ATC GAA GCG CTG TTC CGC GAG TAA GTA CCC TTG TCA
 G   L   N   I   E   A   L   F   R   E   *
                                    ← rpoS ends
```

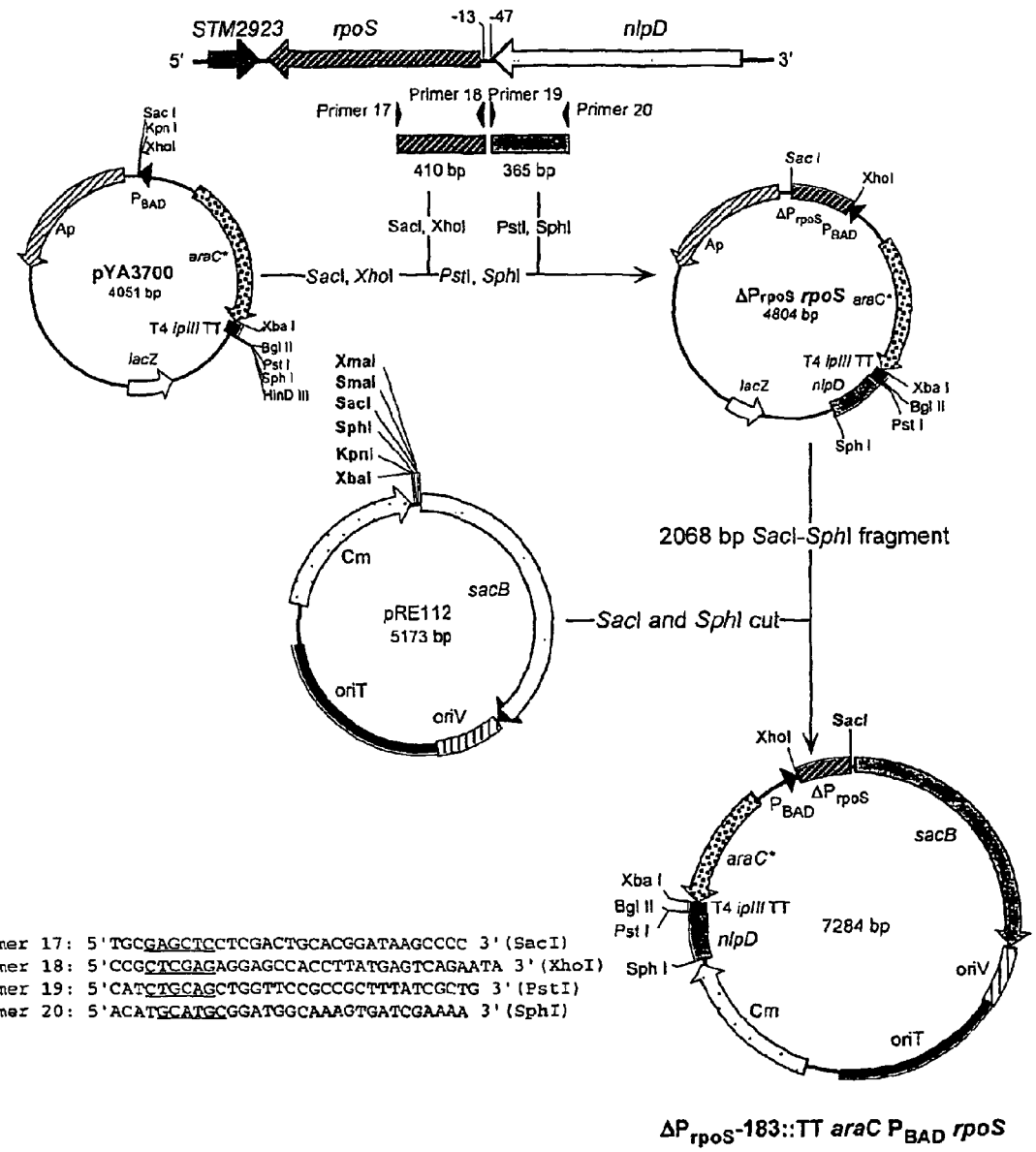
Figure 26. Construction of suicide vector for introducing ΔP_rpoS-183::TT araC P_BAD rpoS deletion-insertion mutation.
Primer 17: 5'TGCGAGCTCCTCGACTGCACGGATAAGCCCC 3' (SacI)
Primer 18: 5'CCGCTCGAGAGGAGCCACCTTATGAGTCAGAATA 3' (XhoI)
Primer 19: 5'CATCTGCAGCTGGTTCCGCCGCTTTATCGCTG 3' (PstI)
Primer 20: 5'ACATGCATGCGGATGGCAAAGTGATCGAAAA 3' (SphI)

Figure 27. Chromosomal map of ΔP$_{rpoS}$-183::TT araC P$_{BAD}$ rpoS deletion-insertion muation.
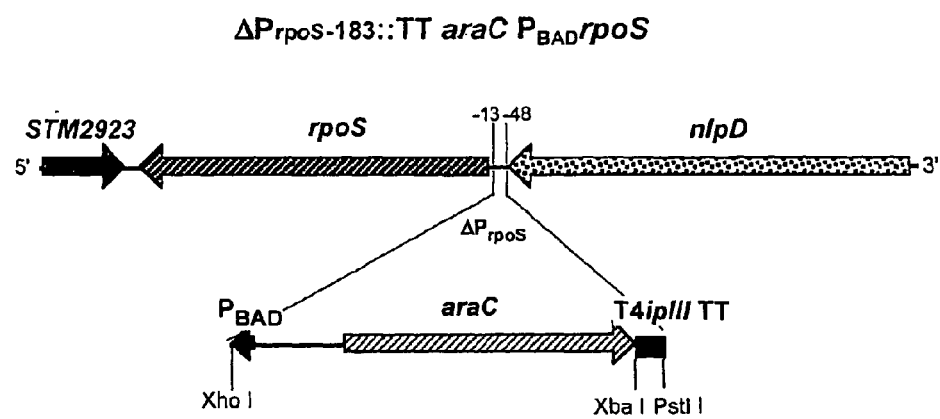
rpoS promoter region (-13 to -48) deleted and 1344 bp P$_{BAD}$ araC TT inserted.

Figure 28. DNA and amino acid sequences of th S. typhimurium P$_{phoPQ}$ and phoPQ and th flanking region.

```
PurB/asl →
ATT GCG TTG AAC CAT TTC AAA CAG AAA ACC ATC GCC GGG GAG ATC GGT TCT TCT ACC ATG
 I   A   L   N   H   F   K   Q   K   T   I   A   G   E   I   G   S   S   T   M CCG CAT AAA GTT AAC CCC ATT GAC TTT GAA AAC TCA GAA GGC AAC CTC GGT CTG TCT AAC
 P   H   K   V   N   P   I   D   F   E   N   S   E   G   N   L   G   L   S   N GCA GTG TTG CAC CAT CTG GCA AAC AAA CTG CCG GTT TCC CGC TGG CAG CGC GAT CTG ACC
 A   V   L   H   H   L   A   N   K   L   P   V   S   R   W   Q   R   D   L   T GAC TCA ACC GTC CTG CGT AAC CTG GGT GTC GGC ATC GGC TAT GCG CTT ATC GCT TAT CAG
 D   S   T   V   L   R   N   L   G   V   G   I   G   Y   A   L   I   A   Y   Q TCC ACC CTG AAG GGC GTC AGC AAG CTG GAA GTA AAC CGC GAT CAT CTG CTT GAC GAA CTG
 S   T   L   K   G   V   S   K   L   E   V   N   R   D   H   L   L   D   E   L GAT CAC AAC TGG GAA GTA TTA GCC GAA CCG ATC CAG ACC GTC ATG CGC CGC TAT GGT ATT
 D   H   N   W   E   V   L   A   E   P   I   Q   T   V   M   R   R   Y   G   I GAA AAA CCA TAT GAA AAA CTG AAA GAG TTG ACC CGT GGC AAG CGT GTT GAT GCC GAA GGA
 E   K   P   Y   E   K   L   K   E   L   T   R   G   K   R   V   D   A   E   G ATG AAA CAG TTT ATT GAT AGT CTG GCC CTG CCG GAA GCA GAA AAA ACG CGC CTT AAA GCC
 M   K   Q   F   I   D   S   L   A   L   P   E   A   E   K   T   R   L   K   A ATG ACG CCG GCA AAT TAT ATC GGT CGC GCT GTG ACT CTG GTC GAC GAA CTT AAA TAA TGC
 M   T   P   A   N   Y   I   G   R   A   V   T   L   V   D   E   L   K   *
                                                                    ←purB ends CTG CCT CAC CCT CTT TTC TTC AGA AAG AGG GTG ACT ATT TGT CTG GTT TAT TAA CTG TTT
             ↑
       phoPQ$_{-109}$         ΔP$_{phoPQ}$ (phoPQ-109 to phoPQ-12 deleted)

ATC CCC AAA GCA CCA TAA TCA ACG CTA GAC TGT TCT TAT TGT TAA CAC AAG GGA GAA GAG
                                                                 ‾‾‾‾‾‾‾
                                                                 ↑ SD
                                                                 phoPQ$_{-12}$
723/1                                 753/11
ATG ATG CGC GTA CTG GTT GTA GAG GAT AAT GCA TTA TTA CGC CAC CAC CTG AAG GTT CAG
‾‾‾ M   M   R   V   L   V   V   E   D   N   A   L   L   R   H   H   L   K   V   Q
phoP starts →

783/21                                813/31
CTC CAG GAT TCA GGT CAC CAG GTC GAT GCC GCA GAA GAT GCC AGG GAA GCT GAT TAC TAC
 L   Q   D   S   G   H   Q   V   D   A   A   E   D   A   R   E   A   D   Y   Y
843/41                                873/51
CTT AAT GAA CAC CTT CCG GAT ATC GCT ATT GTC GAT TTA GGT CTG CCG GAT GAA GAC GGC
 L   N   E   H   L   P   D   I   A   I   V   D   L   G   L   P   D   E   D   G
903/61                                933/71
CTT TCC TTA ATA CGC CGC TGG CGC AGC AGT GAT GTT TCA CTG CCG GTT CTG GTG TTA ACC
 L   S   L   I   R   R   W   R   S   S   D   V   S   L   P   V   L   V   L   T
963/81                                993/91
GCG CGC GAA GGC TGG CAG GAT AAA GTC GAG GTT CTC AGC TCC GGG GCC GAT GAC TAC GTG
 A   R   E   G   W   Q   D   K   V   E   V   L   S   S   G   A   D   D   Y   V
1023/101                              1053/111
ACG AAG CCA TTC CAC ATC GAA GAG GTA ATG GCG CGT ATG CAG GCG TTA ATG CGC CGT AAT
 T   K   P   F   H   I   E   E   V   M   A   R   M   Q   A   L   M   R   R   N
```

Figure 28. (cont'd)

```
1083/121                                        1113/131
AGC GGT CTG GCC TCC CAG GTG ATC AAC ATC CCG CCG TTC CAG GTG GAT CTC TCA CGC CGG
 S   G   L   A   S   Q   V   I   N   I   P   P   F   Q   V   D   L   S   R   R
1143/141                                        1173/151
GAA TTA TCC GTC AAT GAA GAG GTC ATC AAA CTC ACG GCG TTC GAA TAC ACC ATT ATG GAA
 E   L   S   V   N   E   E   V   I   K   L   T   A   F   E   Y   T   I   M   E
1203/161                                        1233/171
ACG CTT ATC CGT AAC AAC GGT AAA GTG GTC AGC AAA GAT TCG CTG ATG CTT CAG CTG TAT
 T   L   I   R   N   N   G   K   V   V   S   K   D   S   L   M   L   Q   L   Y
1263/181                                        1293/191
CCG GAT GCG GAA CTG CGG GAA AGT CAT ACC ATT GAT GTT CTC ATG GGG CGT CTG CGG AAA
 P   D   A   E   L   R   E   S   H   T   I   D   V   L   M   G   R   L   R   K
1323/201                                        1353/211
AAA ATA CAG GCC CAG TAT CCG CAC GAT GTC ATT ACC ACC GTA CGC GGA CAA GGA TAT CTT
 K   I   Q   A   Q   Y   P   H   D   V   I   T   T   V   R   G   Q   G   Y   L

1383/221       ← phoP ends
TTT GAA TTG CGC TAA TGA
 F   E   L   R   *   *
                phoQ starts →        1415/11
                ATG AAT AAA TTT GCT CGC CAT TTT CTG CCG CTG TCG CTG CGG GTT CGT
                 M   N   K   F   A   R   H   F   L   P   L   S   L   R   V   R
1445/21                                         1475/31
TTT TTG CTG GCG ACA GCC GGC GTC GTG CTG GTG CTT TCT TTG GCA TAT GGC ATA GTG GCG
 F   L   L   A   T   A   G   V   V   L   V   L   S   L   A   Y   G   I   V   A
1505/41                                         1535/51
CTG GTC GGC TAT AGC GTA AGT TTT GAT AAA ACC ACC TTT CGT TTG CTG CGC GGC GAA AGC
 L   V   G   Y   S   V   S   F   D   K   T   T   F   R   L   L   R   G   E   S
1565/61                                         1595/71
AAC CTG TTT TAT ACC CTC GCC AAA TGG GAA AAT AAT AAA ATC AGC GTT GAG CTG CCT GAA
 N   L   F   Y   T   L   A   K   W   E   N   N   K   I   S   V   E   L   P   E
1625/81                                         1655/91
AAT CTG GAC ATG CAA AGC CCG ACC ATG ACG CTG ATT TAC GAT GAA ACG GGC AAA TTA TTA
 N   L   D   M   Q   S   P   T   M   T   L   I   Y   D   E   T   G   K   L   L
1685/101                                        1715/111
TGG ACG CAG CGC AAC ATT CCC TGG CTG ATT AAA AGC ATT CAA CCG GAA TGG TTA AAA ACG
 W   T   Q   R   N   I   P   W   L   I   K   S   I   Q   P   E   W   L   K   T
1745/121                                        1775/131
AAC GGC TTC CAT GAA ATT GAA ACC AAC GTA GAC GCC ACC AGC ACG CTG TTG AGC GAA GAC
 N   G   F   H   E   I   E   T   N   V   D   A   T   S   T   L   L   S   E   D
1805/141                                        1835/151
CAT TCC GCG CAG GAA AAA CTC AAA GAA GTA CGT GAA GAT GAC GAT GAT GCC GAG ATG ACC
 H   S   A   Q   E   K   L   K   E   V   R   E   D   D   D   D   A   E   M   T
1865/161                                        1895/171
CAC TCG GTA GCG GTA AAT ATT TAT CCT GCC ACG GCG CGG ATG CCG CAG TTA ACC ATC GTG
 H   S   V   A   V   N   I   Y   P   A   T   A   R   M   P   Q   L   T   I   V
1925/181                                        1955/191
GTG GTC GAT ACC ATT CCG ATA GAA CTA AAA CGC TCC TAT ATG GTG TGG AGC TGG TTC GTA
 V   V   D   T   I   P   I   E   L   K   R   S   Y   M   V   W   S   W   F   V
1985/201                                        2015/211
TAC GTG CTG GCC GCC AAT TTA CTG TTA GTC ATT CCT TTA CTG TGG ATC GCC GCC TGG TGG
 Y   V   L   A   A   N   L   L   L   V   I   P   L   L   W   I   A   A   W   W
2045/221                                        2075/231
AGC TTA CGC CCT ATC GAG GCG CTG GCG CGG GAA GTC CGC GAG CTT GAA GAT CAT CAC CGC
 S   L   R   P   I   E   A   L   A   R   E   V   R   E   L   E   D   H   H   R
2105/241                                        2135/251
GAA ATG CTC AAT CCG GAG ACG ACG CGT GAG CTG ACC AGC CTT GTG CGC AAC CTT AAT CAA
 E   M   L   N   P   E   T   T   R   E   L   T   S   L   V   R   N   L   N   Q
2165/261                                        2195/271
```

Figure 28. (cont'd)

```
CTG CTC AAA AGC GAG CGT GAA CGT TAT AAC AAA TAC CGC ACG ACC CTG ACC GAC CTG ACG
 L   L   K   S   E   R   E   R   Y   N   K   Y   R   T   T   L   T   D   L   T
2225/281                                    2255/291
CAC AGT TTA AAA ACG CCG CTC GCG GTT TTG CAG AGT ACG TTA CGC TCT TTA CGC AAC GAA
 H   S   L   K   T   P   L   A   V   L   Q   S   T   L   R   S   L   R   N   E
2285/301                                    2315/311
AAG ATG AGC GTC AGC AAA GCT GAA CCG GTG ATG CTG GAA CAG ATC AGC CGG ATT TCC CAG
 K   M   S   V   S   K   A   E   P   V   M   L   E   Q   I   S   R   I   S   Q
2345/321                                    2375/331
CAG ATC GGC TAT TAT CTG CAT CGC GCC AGT ATG CGC GGT AGC GGC GTG TTG TTA AGC CGC
 Q   I   G   Y   Y   L   H   R   A   S   M   R   G   S   G   V   L   L   S   R
2405/341                                    2435/351
GAA CTG CAT CCC GTC GCG CCG TTG TTA GAT AAC CTG ATT TCT GCG CTA AAT AAA GTT TAT
 E   L   H   P   V   A   P   L   L   D   N   L   I   S   A   L   N   K   V   Y
2465/361                                    2495/371
CAG CGT AAA GGG GTG AAT ATC AGT ATG GAT ATT TCA CCA GAA ATC AGT TTT GTC GGC GAG
 Q   R   K   G   V   N   I   S   M   D   I   S   P   E   I   S   F   V   G   E
2525/381                                    2555/391
CAA AAC GAC TTT GTC GAA GTG ATG GGC AAC GTA CTG GAC AAC GCT TGT AAA TAT TGT CTG
 Q   N   D   F   V   E   V   M   G   N   V   L   D   N   A   C   K   Y   C   L
2585/401                                    2615/411
GAG TTT GTC GAG ATT TCG GCT CGC CAG ACC GAC GAT CAT TTG CAT ATT TTC GTC GAA GAT
 E   F   V   E   I   S   A   R   Q   T   D   D   H   L   H   I   F   V   E   D
2645/421                                    2675/431
GAC GGC CCA GGC ATT CCC CAC AGC AAA CGT TCC CTG GTG TTT GAT CGC GGT CAG CGC GCC
 D   G   P   G   I   P   H   S   K   R   S   L   V   F   D   R   G   Q   R   A
2705/441                                    2735/451
GAT ACC CTA CGA CCA GGA CAA GGC GTG GGG CTG GCT GTC GCG CGC GAG ATT ACG GAA CAA
 D   T   L   R   P   G   Q   G   V   G   L   A   V   A   R   E   I   T   E   Q
2765/461                                    2795/471
TAC GCC GGG CAG ATC ATT GCC AGC GAC AGT CTG CTC GGT GGC GCC CGT ATG GAG GTC GTT
 Y   A   G   Q   I   I   A   S   D   S   L   L   G   G   A   R   M   E   V   V
2825/481                                    2855/491
TTT GGC CGA CAG CAT CCC ACA CAG AAA GAG GAA TAA
 F   G   R   Q   H   P   T   Q   K   E   E   *
                                     ← phoQ ends
```

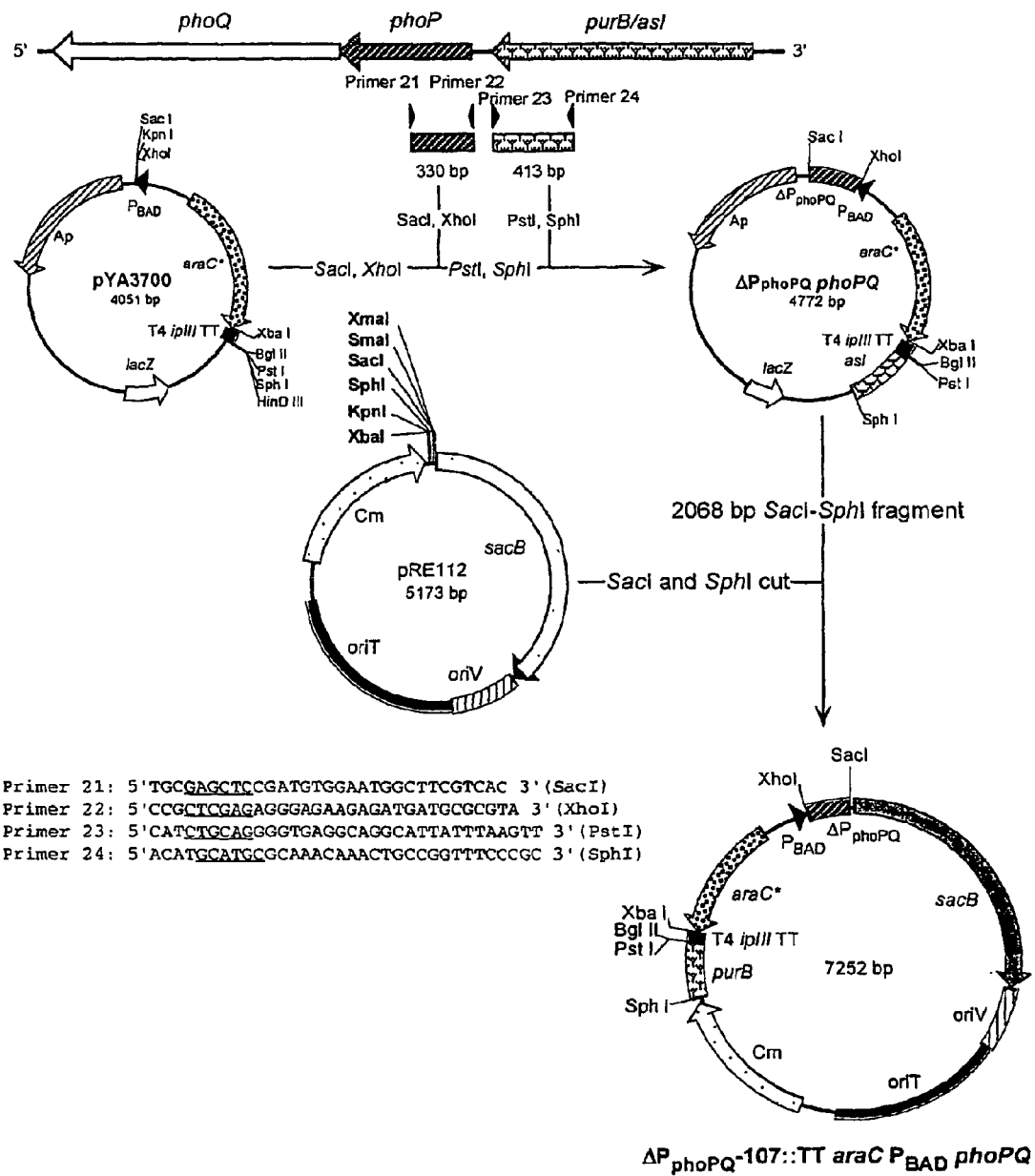
Figure 29. Construction of the suicide vector for introduing $\Delta P_{phoPQ}$-107::TT araC $P_{BAD}$ phoPQ deletion-insertion mutation.

Figure 30. Chromosomal map of $\Delta P_{phoPQ}$-107::TT araC $P_{BAD}$ phoPQ deletion-insertion mutation.
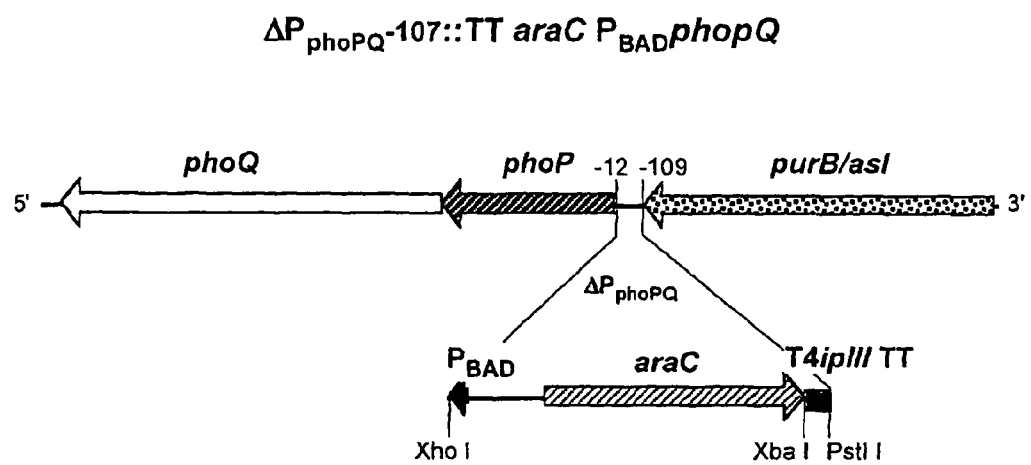
phoPQ promoter region (-12 to -109) deleted and 1344 bp $P_{BAD}$ araC TT inserted.

Figure 31. Diagrams of the suicide vectors for introducing the ΔaraBAD23 and ΔaraE25 deletion mutations.
1 ΔaraBAD23
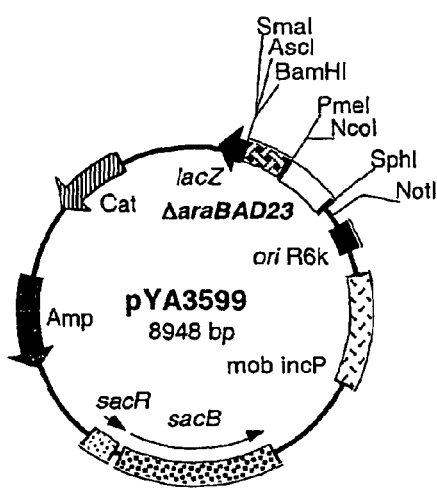
2. ΔaraE25
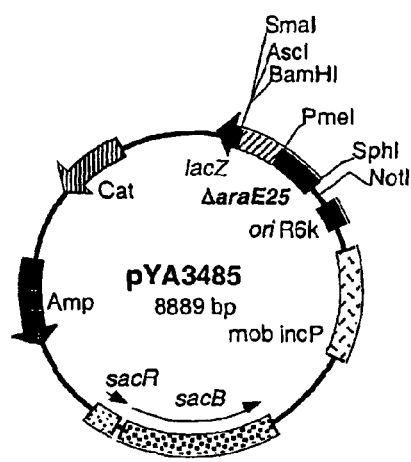
In *Salmonella* chromosome:
1. ΔaraBAD23
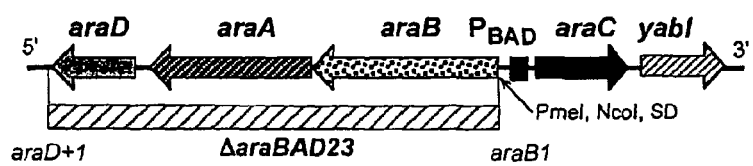
araBAD (araB1 to araD+1, total of 4101 bp) deleted and SD, NcoI, and PmeI sites generated
2. ΔaraE25
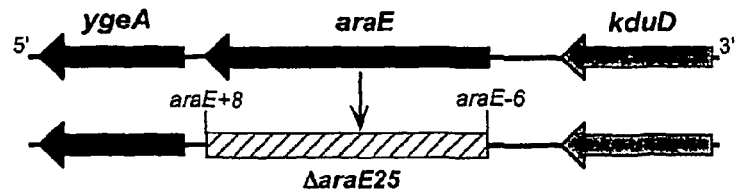
araE-6 to araE+8, total of 1433 bp was deleted Figure 32. Construction of the suicide vector for introducing the Δ(*gmd-fcl*)-26 deletion mutation.

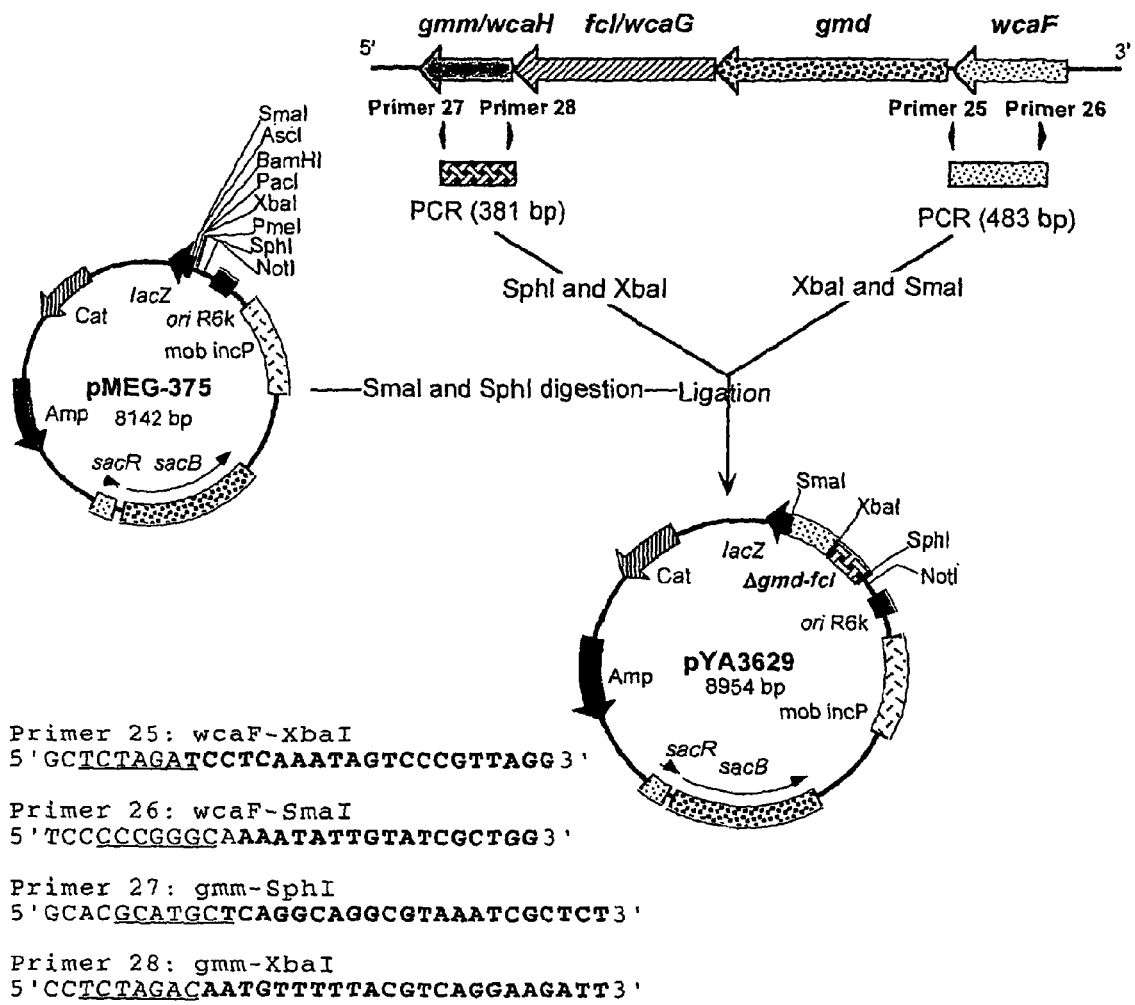

Primer 25: wcaF-XbaI
5'GC<u>TCTAGA</u>TCCTCAAATAGTCCCGTTAGG 3'

Primer 26: wcaF-SmaI
5'TCC<u>CCCGGG</u>CAAAATATTGTATCGCTGG 3'

Primer 27: gmm-SphI
5'GCAC<u>GCATGC</u>TCAGGCAGGCGTAAATCGCTCT 3'

Primer 28: gmm-XbaI
5'CC<u>TCTAGA</u>CAATGTTTTTACGTCAGGAAGATT 3'

*gmm/wcaH* : Guanosine di-P mannose mannosyl hydrolase
*fcl/wcaG*: Colanic acid gene cluster, bifunctional GDP fucose synthetase
*gmd*: Fucose biosynthesis; GDP-D-mannose 4,6-dehydratase
*wcaF*: Involved in lipopolysaccharide biosynthesis, putative acyltransferase Figure 33. Chromosomal map of the Δ(*gmd-fcl*)-26 deletion mutation.
In *Salmonella* chromosome:
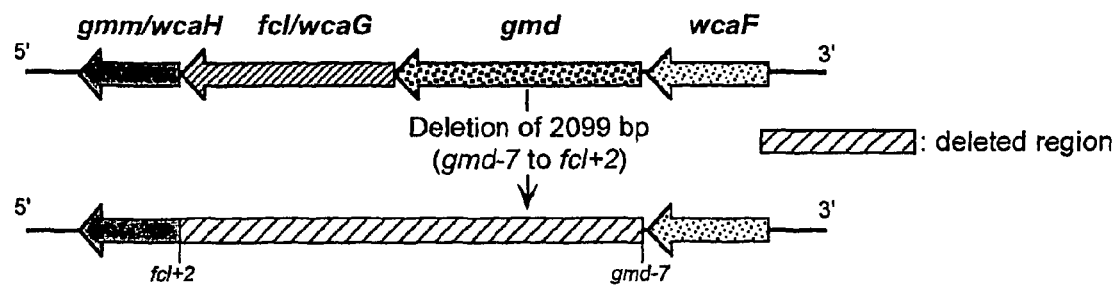

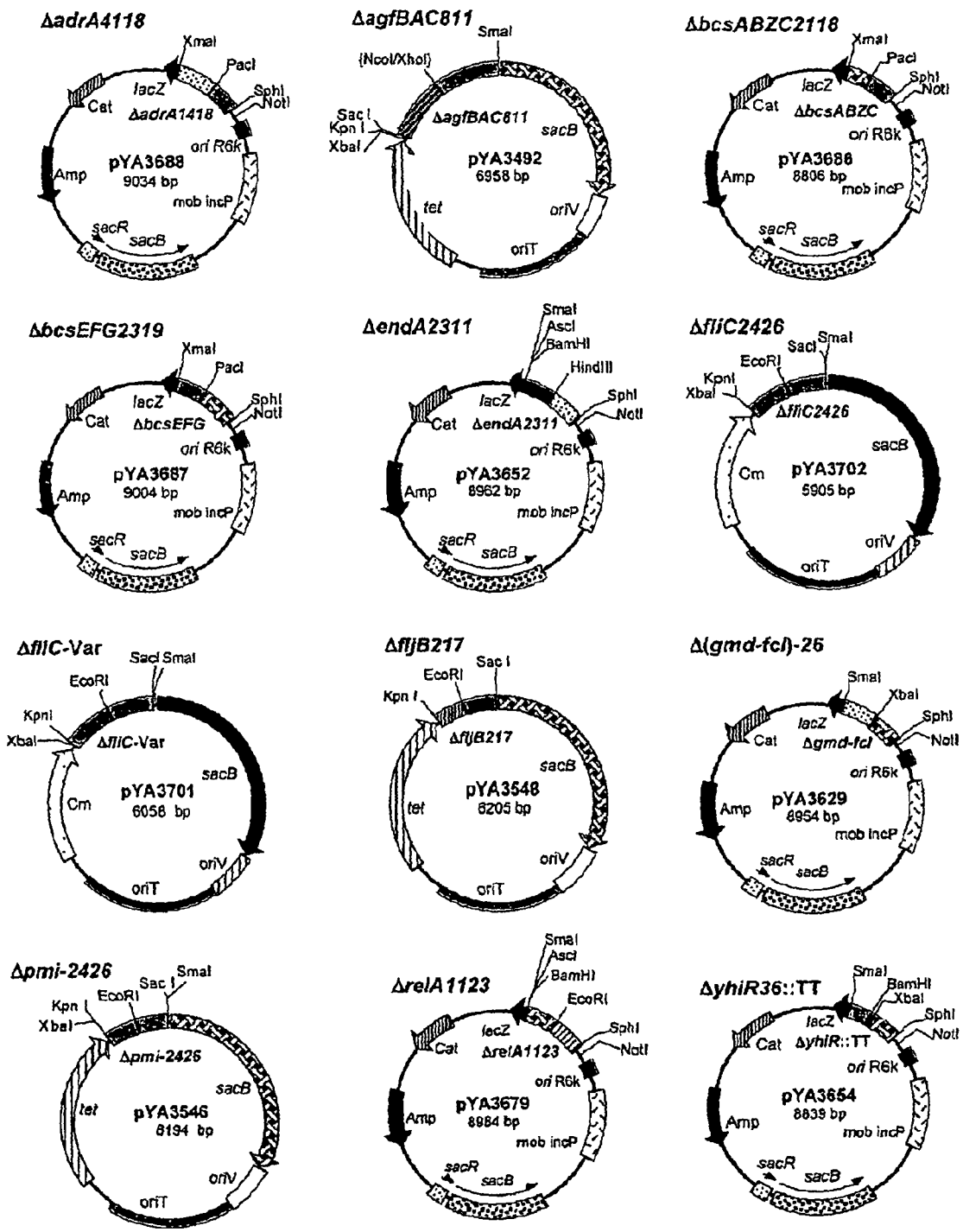
Figure 34. Diagrams of all the suicide vectors listed in Table 2.

Figure 35. Deletion mutations after insertion into *Salmonella* chromosome.
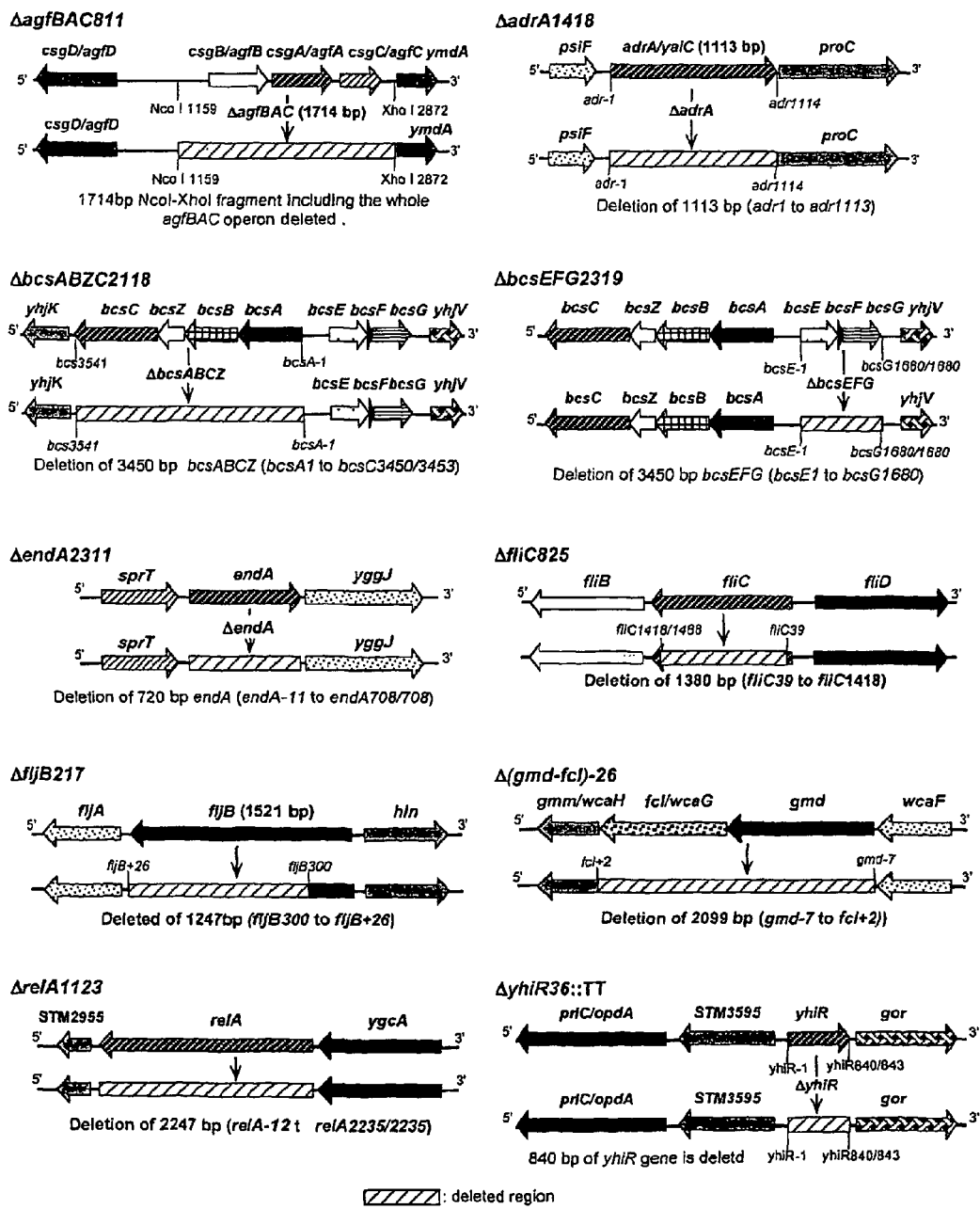

Figure 36. DNA and amino acid sequences of *sopB* and the flanking region of
S. typhimurium chromosome.

```
GGA ATA GGA AAA ACG AAT ATT CTT CGT CAC GGT CTT ACT TGT CCG GGG CTT TGC TGG CAT
 S   Y   S   F   R   I   N   K   T   V   T   K   S   T   R   P   K   A   P   M
                                                                  ←STM1092 starts ↑

ACA CAC ACC TGT ATA ACA TTT GAT GTA ACG CCG TTA CTT TAC GCA GGA GTA AAT CGG TGA
        ―――
        SD (STM1092)
ATT TGA TCT GAG TCA AGA AGG TGG GTT TTC AAT AAA AGT TGT GCC ATA AAT TGT GAA GTT

TGT AGA TTT TAT GAA CAT TTG ATG TAC CGA TCT CCC CCA TGA TCG CCA CTA CGT ATG GAC

GTC AGG ATG CCT CCC CGC CTG ATC AGA AGC GTT TCC TCA TTA AAA AGG ACA TTT TTT TAA

AGT TCC TGG TGC ATA AAA GTC ACA TCC TTT TAA AGG GTT GTT AAC CCT GTT GAA TGT TCC
                    SD
CAC TCC CCT ATT CAG GAA TAT TAA AAA CGC  T
                ―――――――
              ↑SD-sopB deleted (sopB-18 to sopB1686)
sopB starts →
1/1                                                 31/11
ATG CAA ATA CAG AGC TTC TAT CAC TCA GCT TCA CTA AAA ACC CAG GAG GCT TTT AAA AGC
 M   Q   I   Q   S   F   Y   H   S   A   S   L   K   T   Q   E   A   F   K   S
61/21                                               91/31
CTA CAA AAA ACC TTA TAC AAC GGA ATG CAG ATT CTC TCA GGC CAG GGC AAA GCG CCG GCT
 L   Q   K   T   L   Y   N   G   M   Q   I   L   S   G   Q   G   K   A   P   A
121/41                                              151/51
AAA GCG CCC GAC GCT CGC CCG GAA ATT ATT GTC CTG CGA GAA CCC GGC GCG ACA TGG GGG
 K   A   P   D   A   R   P   E   I   I   V   L   R   E   P   G   A   T   W   G
181/61                                              211/71
AAT TAT CTA CAG CAT CAG AAG GCG TCT AAC CAC TCG CTG CAT AAC CTC TAT AAC TTA CAG
 N   Y   L   Q   H   Q   K   A   S   N   H   S   L   H   N   L   Y   N   L   Q
241/81                                              271/91
CGC GAT CTT CTT ACC GTC GCG GCA ACC GTT CTG GGT AAA CAA GAC CCG GTT CTA ACG TCA
 R   D   L   L   T   V   A   A   T   V   L   G   K   Q   D   P   V   L   T   S
301/101                                             331/111
ATG GCA AAC CAA ATG GAG TTA GCC AAA GTT AAA GCG GAC CGG CCA GCA ACA AAA CAA GAA
 M   A   N   Q   M   E   L   A   K   V   K   A   D   R   P   A   T   K   Q   E
361/121                                             391/131
GAA GCC GCG GCA AAA GCA TTG AAG AAA AAT CTT ATC GAA CTT ATT GCA GCA CGC ACT CAG
 E   A   A   A   K   A   L   K   K   N   L   I   E   L   I   A   A   R   T   Q
421/141                                             451/151
CAG CAG GAT GGC TTA CCT GCA AAA GAA GCT CAT CGC TTT GCG GCA GTA GCG TTT AGA GAT
 Q   Q   D   G   L   P   A   K   E   A   H   R   F   A   A   V   A   F   R   D
481/161                                             511/171
GCT CAG GTC AAG CAG CTT AAT AAC CAG CCC TGG CAA ACC ATA AAA AAT ACA CTC ACG CAT
 A   Q   V   K   Q   L   N   N   Q   P   W   Q   T   I   K   N   T   L   T   H
541/181                                             571/191
AAC GGG CAT CAC TAT ACC AAC ACG CAG CTC CCT GCA GCA GAG ATG AAA ATC GGC GCA AAA
 N   G   H   H   Y   T   N   T   Q   L   P   A   A   E   M   K   I   G   A   K
601/201                                             631/211
GAT ATC TTT CCC AGT GCT TAT GAG GGA AAG GGC GTA TGC AGT TGG GAT ACC AAG AAT ATT
 D   I   F   P   S   A   Y   E   G   K   G   V   C   S   W   D   T   K   N   I
```

Figure 36. (cont'd)

```
661/221                                     691/231
CAT CAC GCC AAT AAT TTG TGG ATG TCC ACG GTG AGT GTG CAT GAG GAC GGT AAA GAT AAA
 H   H   A   N   N   L   W   M   S   T   V   S   V   H   E   D   G   K   D   K
721/241                                     751/251
ACG CTT TTT TGC GGG ATA CGT CAT GGC GTG CTT TCC CCC TAT CAT GAA AAA GAT CCG CTT
 T   L   F   C   G   I   R   H   G   V   L   S   P   Y   H   E   K   D   P   L
781/261                                     811/271
CTG CGT CAC GTC GGC GCT GAA AAC AAA GCC AAA GAA GTA TTA ACT GCG GCA CTT TTT AGT
 L   R   H   V   G   A   E   N   K   A   K   E   V   L   T   A   A   L   F   S
841/281                                     871/291
AAA CCT GAG TTG CTT AAC AAA GCC TTA GCG GGC GAG GCG GTA AGC CTG AAA CTG GTA TCC
 K   P   E   L   L   N   K   A   L   A   G   E   A   V   S   L   K   L   V   S
901/301                                     931/311
GTC GGG TTA CTC ACC GCG TCG AAT ATT TTC GGC AAA GAG GGA ACG ATG GTC GAG GAC CAA
 V   G   L   L   T   A   S   N   I   F   G   K   E   G   T   M   V   E   D   Q
961/321                                     991/331
ATG CGC GCA TGG CAA TCG TTG ACC CAG CCG GGA AAA ATG ATT CAT TTA AAA ATC CGC AAT
 M   R   A   W   Q   S   L   T   Q   P   G   K   M   I   H   L   K   I   R   N
1021/341                                    1051/351
AAA GAT GGC GAT CTA CAG ACG GTA AAA ATA AAA CCG GAC GTC GCC GCA TTT AAT GTG GGT
 K   D   G   D   L   Q   T   V   K   I   K   P   D   V   A   A   F   N   V   G
1081/361                                    1111/371
GTT AAT GAG CTG GCG CTC AAG CTC GGC TTT GGC CTT AAG GCA TCG GAT AGC TAT AAT GCC
 V   N   E   L   A   L   K   L   G   F   G   L   K   A   S   D   S   Y   N   A
1141/381                                    1171/391
GAG GCG CTA CAT CAG TTA TTA GGC AAT GAT TTA CGC CCT GAA GCC AGA CCA GGT GGC TGG
 E   A   L   H   Q   L   L   G   N   D   L   R   P   E   A   R   P   G   G   W
1201/401                                    1231/411
GTT GGC GAA TGG CTG GCG CAA TAC CCG GAT AAT TAT GAG GTC GTC AAT ACA TTA GCG CGC
 V   G   E   W   L   A   Q   Y   P   D   N   Y   E   V   V   N   T   L   A   R
1261/421                                    1291/431
CAG ATT AAG GAT ATA TGG AAA AAT AAC CAA CAT CAT AAA GAT GGC GGC GAA CCC TAT AAA
 Q   I   K   D   I   W   K   N   N   Q   H   H   K   D   G   G   E   P   Y   K
1321/441                                    1351/451
CTC GCA CAA CGC CTT GCC ATG TTA GCC CAT GAA ATT GAC GCG GTA CCC GCC TGG AAT TGT
 L   A   Q   R   L   A   M   L   A   H   E   I   D   A   V   P   A   W   N   C
1381/461                                    1411/471
AAA AGC GGC AAA GAT CGT ACA GGG ATG ATG GAT TCA GAA ATC AAG CGA GAG ATC ATT TCC
 K   S   G   K   D   R   T   G   M   M   D   S   E   I   K   R   E   I   I   S
1441/481                                    1471/491
TTA CAT CAG ACC CAT ATG TTA AGT GCG CCT GGT AGT CTT CCG GAT AGC GGT GGA CAG AAA
 L   H   Q   T   H   M   L   S   A   P   G   S   L   P   D   S   G   G   Q   K
1501/501                                    1531/511
ATT TTC CAA AAA GTA TTA CTG AAT AGC GGT AAC CTG GAG ATT CAG AAA CAA AAT ACG GGC
 I   F   Q   K   V   L   L   N   S   G   N   L   E   I   Q   K   Q   N   T   G
1561/521                                    1591/531
GGG GCG GGA AAC AAA GTA ATG AAA AAT TTA TCG CCA GAG GTG CTC AAT CTT TCC TAT CAA
 G   A   G   N   K   V   M   K   N   L   S   P   E   V   L   N   L   S   Y   Q
1621/541                                    1651/551
AAA CGA GTT GGG GAT GAA AAT ATT TGG CAG TCA GTA AAA GGC ATT TCT TCA TTA ATC ACA
 K   R   V   G   D   E   N   I   W   Q   S   V   K   G   I   S   S   L   I   T
1681/561
TCT TGA  GTCTTGAGGTAACTAT    ATG GAA AGT CTA TTA AAT CGT TTA TAT GAC GCG TTA GGC
 S   *↑          SD           M   E   S   L   L   N   R   L   Y   D   A   L   G
  (sopB1686)                 pipC starts
```

Figure 37. Construction of the suicide vector for introducing the ΔsopB deletion mutation into the *Salmonella* chromosome.

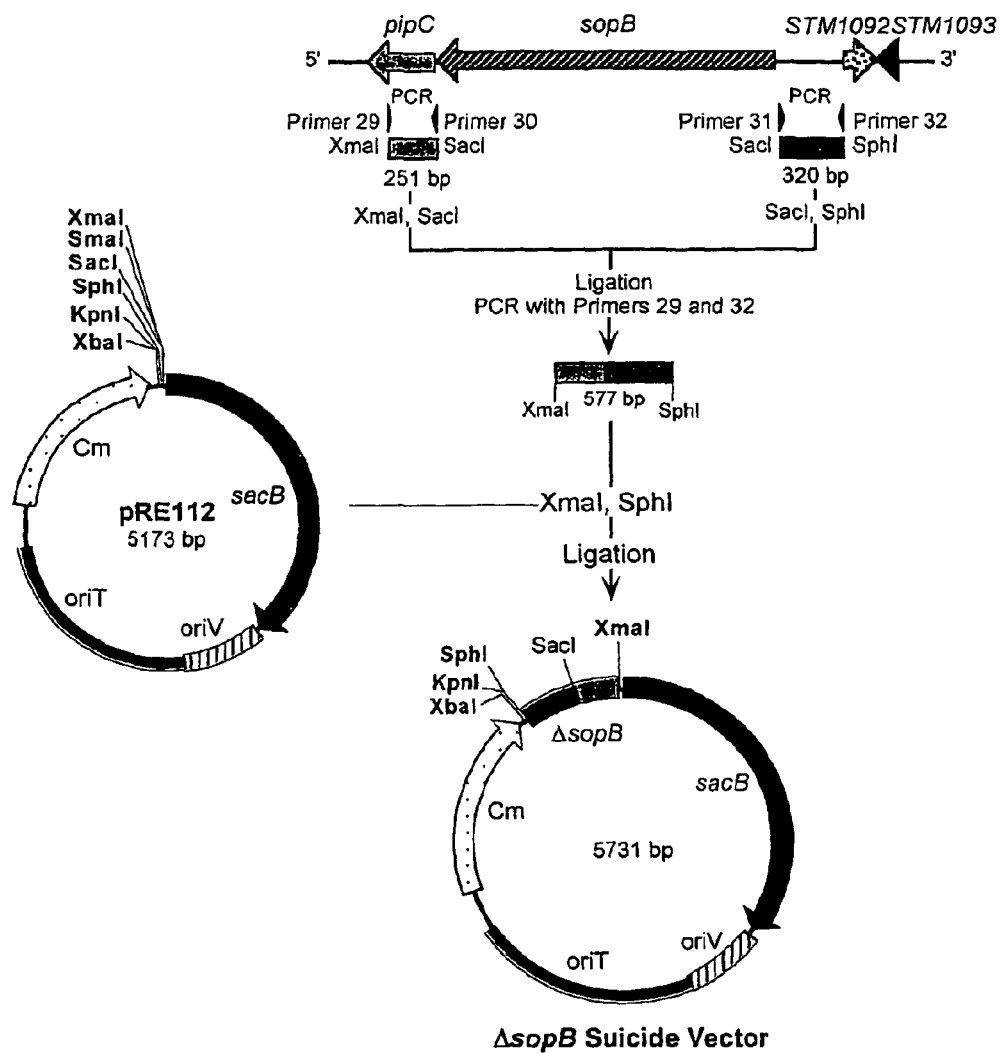

Primer 29: 5' TTCC<u>CCCGGGG</u>CAGTATTGTCTGCGTCAGCG 3' (XmaI-N)
Primer 30: 5' TTGA<u>GAGCTC</u>GTCTTGAGGTAACTATATGGAAAG 3' (SacI-N)
Primer 31: 5' TTGA<u>GAGCTC</u>GAATAGGGGAGTGGGAACATTC 3' (SacI-C)
Primer 32: 5' ACAT<u>GCATGC</u>GGCATACACACACCTGTATAACA 3' (SphI-C)

Figure 38. Chromosomal map of ΔsopB deletion mutation.
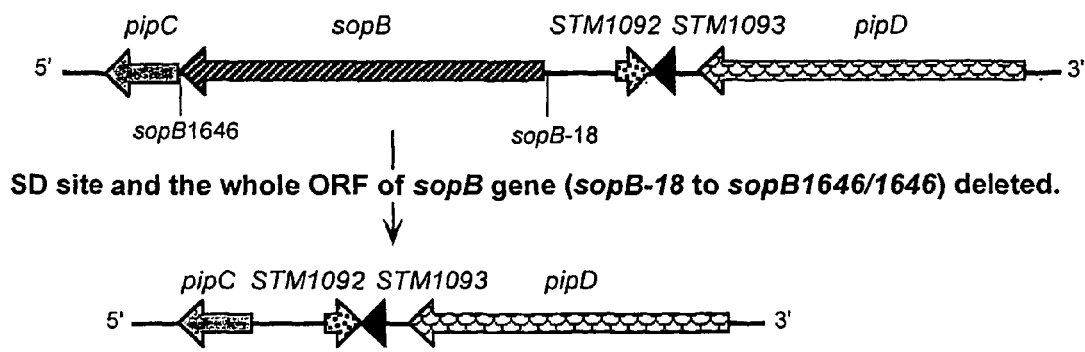

Figure 39. Diagrams of the suicide vectors for introducing ΔasdA16 into S. typhimurium and ΔasdA25 into S. paratyphi A and S. typhi strains.

Figure 40. Chromosomal maps of ΔasdA16 and ΔasdA25 deletion mutation.
ΔasdA16 for S. typhimurium
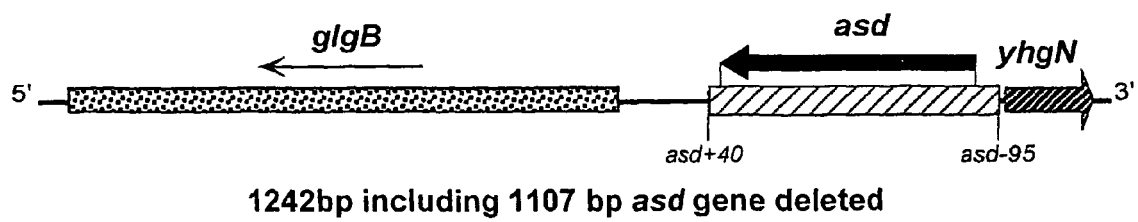
1242bp including 1107 bp asd gene deleted
ΔasdA25 for S paratyphi A and S. typhi
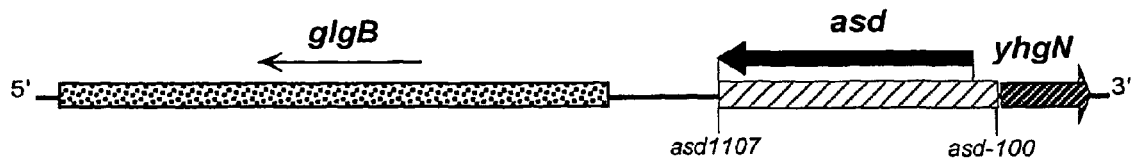
~1200 bp including 1107 bp asd gene deleted
(flanking region sequences are from Salmonella paratyphi A)
▨ : deleted region

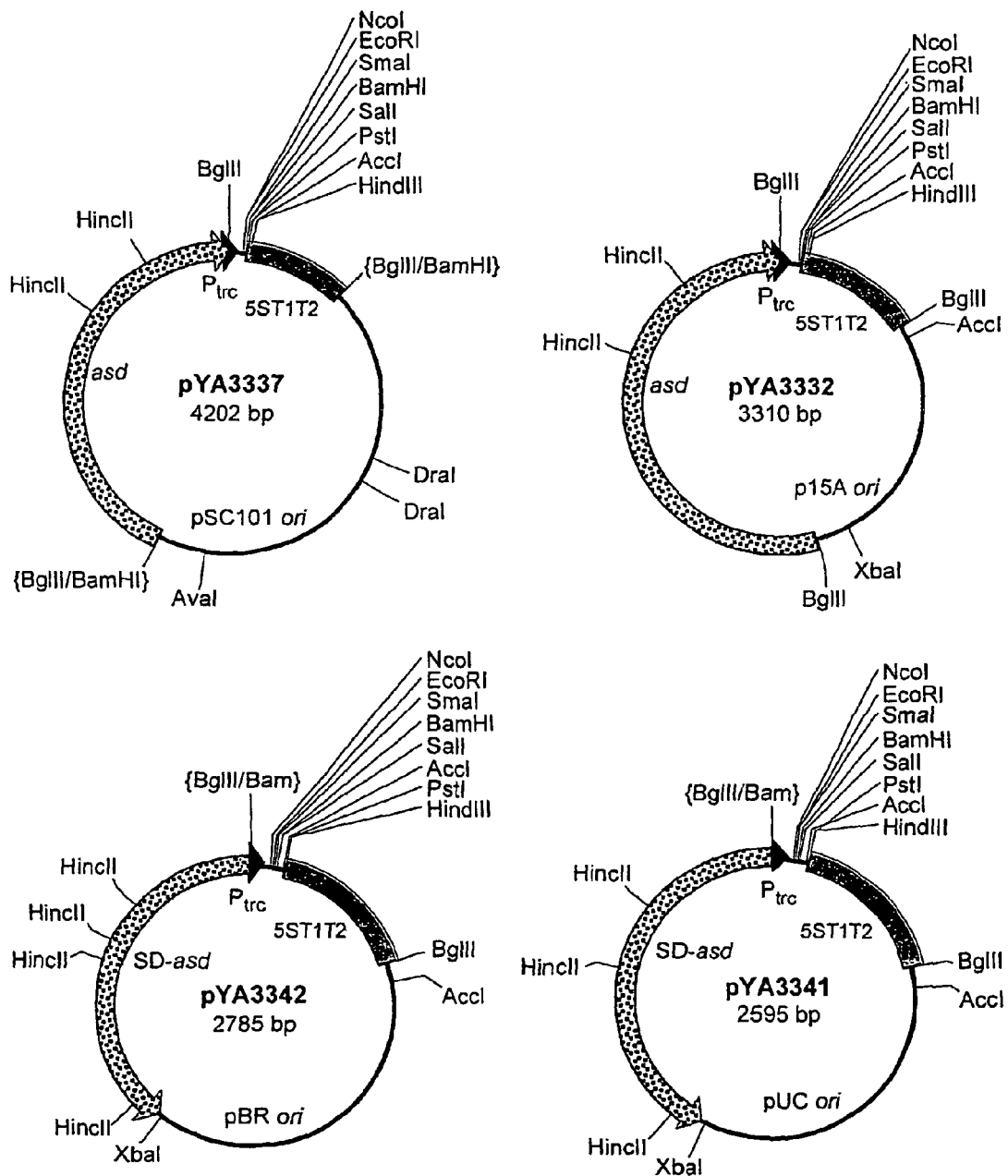
Figure 41. Asd+ vectors with pSC101, p15A, pBR and pUC origins of replication to regulate plasmid copy numbers.

Figure 42. Nucleotide sequ nce of P$_{trc}$ and the multiple cloning sites (MCS) of Asd⁺ vectors in Figure 41.

```
                        -35                              -10
ATT CTG AAA TGA GCT GTT GAC AAT TAA TCA TCC GGC TCG TAT AAT GTG TGG AAT TGT

EcoRI
GAG CGG ATA ACA ATT TCA CAC AGG AAA CAG ACC ATG GAA ATT CGC AAT TCC CGG GGA
                                SD         NcoI                    SmaI
                                           Met Gly Ile Arg Asn Ser Arg Gly
BamHI        PstI
TCC GTC GAC CTG CAG CCA AGC TCC CAA GCT T
    SalI                        HindIII
Ser Val Asp Leu Gln Pro Ser Ser Gln Ala
```

Figure 43. Diagram of the suicide vector f r introducing Δ*ilvG3*::TT *araC* P$_{BAD}$ *lacI* TT deletion-insertion mutation and map of Δ*ilvG3*::TT *araC* P$_{BAD}$ *lacI* TT mutation in the *Salmonella* chromosome.
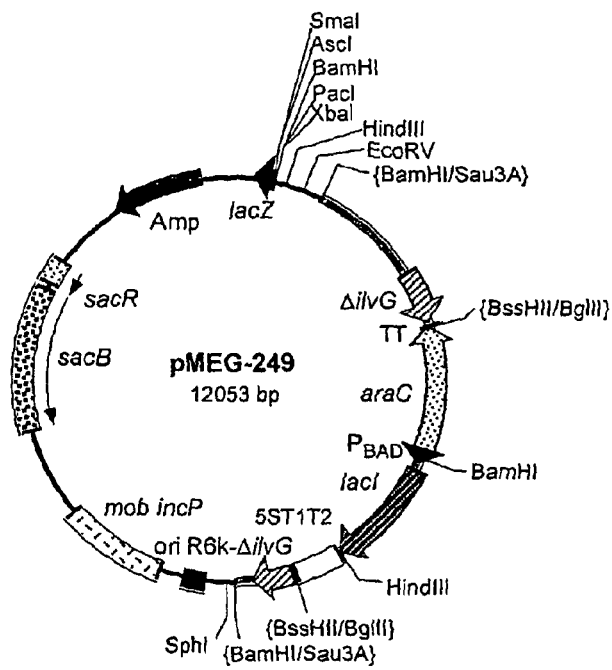
In *Salmonella* chromosome:
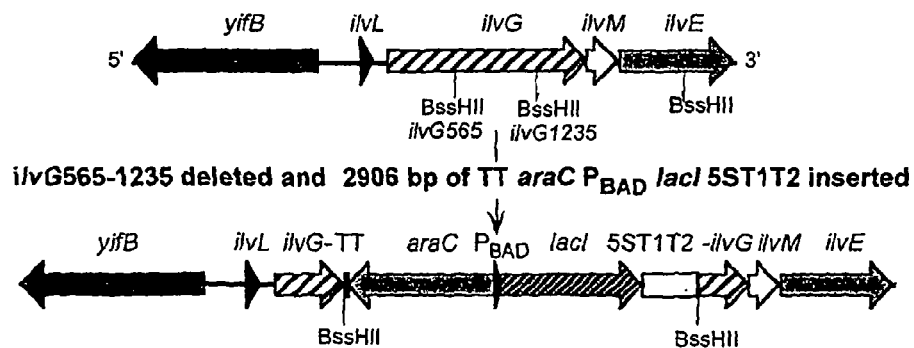

Figure 44: Nucleotide and amino acid sequnces of *S. typhimurium* *fimH* and FimH protein

```
1/1                                    31/11
atg aaa ata tac tca gcg cta ttg ctg gcg ggg acc gcg ctc ttt ttc acc cat ccc gcg
 M   K   I   Y   S   A   L   L   L   A   G   T   A   L   F   F   T   H   P   A
61/21                                  91/31
ctg gcg acg gtt tgc cgt aat tca aac ggg acg gcg acc gat atc ttt tac gac ctg tca
 L   A ↑ T   V   C   R   N   S   N   G   T   A   T   D   I   F   Y   D   L   S
121/41                                 151/51
gat gtt ttc acc agc ggc aat aat cag ccg gga cag gtg gtg acg ctg ccg gaa aaa tca
 D   V   F   T   S   G   N   N   Q   P   G   Q   V   V   T   L   P   E   K   S
181/61                                 211/71
ggt tgg gtc ggc gta aac gcg acg tgc ccg gcg ggg aca acg gtg aat tat acc tac cga
 G   W   V   G   V   N   A   T   C   P   A   G   T   T   V   N   Y   T   Y   R
241/81                                 271/91
agc tat gta tca gaa tta ccg gta caa agt acc gaa gga aat ttt aaa tac ctc aag ttg
 S   Y   V   S   E   L   P   V   Q   S   T   E   G   N   F   K   Y   L   K   L
301/101                                331/111
aat gac tac ctt ctg ggc gcg atg agc atc acc gat agt gtc gct ggc gta ttt tat ccg
 N   D   Y   L   L   G   A   M   S   I   T   D   S   V   A   G   V   F   Y   P
361/121                                391/131
ccc cgt aac tat att ctc atg ggc gtc gac tat aac gtg tcg cag caa aag ccg ttt ggc
 P   R   N   Y   I   L   M   G   V   D   Y   N   V   S   Q   Q   K   P   F   G
421/141                                451/151
gtg cag gac tca aag ctg gtt ttt aaa tta aaa gtg ata cgg cct ttt att aat atg gtg
 V   Q   D   S   K   L   V   F   K   L   K   V   I   R   P   F   I   N   M   V
481/161                                511/171
acg atc cct cgc cag aca atg ttt acc gtc tat gtg acg acc tct acc ggc gac gcg ttg
 T   I   P   R   Q   T   M   F   T   V   Y   V   T   T   S   T   G   D   A   L
541/181                                571/191
agc acg ccg gta tat acc att agc tac agc ggc aaa gtg gaa gtg ccg caa aac tgt gaa
 S   T   P   V   Y   T   I   S   Y   S   G   K   V   E   V   P   Q   N   C   E
601/201                                631/211
gtg aat gcc gga cag gtc gtg gag ttt gat ttc ggc gat atc ggc gcg tcg tta ttt agt
 V   N   A   G   Q   V   V   E   F   D   F   G   D   I   G   A   S   L   F   S
661/221                                691/231
cag gcg ggg gcg ggt aat cgt ccg caa ggc gtc acg ccg caa acg aaa acc att gct atc
 Q   A   G   A   G   N   R   P   Q   G   V   T   P   Q   T   K   T   I   A   I
721/241                                751/251
aaa tgt acc aac gtc gcg gcg cag gcc tat tta tcg atg cgg ctt gaa gcc gaa aag gcc
 K   C   T   N   V   A   A   Q   A   Y   L   S   M   R   L   E   A   E   K   A
781/261                                811/271
tca ggg cag gcg atg gtg tcc gat aat ccg gat tta ggc ttt gtg gtt gct aat agc aac
 S   G   Q   A   M   V   S   D   N   P   D   L   G   F   V   V   A   N   S   N
841/281                                871/291
ggt acg ccg ctt aca ccc aat aat ttg tcg agt aaa att ccg ttt cat ctt gat gat aac
 G   T   P   L   T   P   N   N   L   S   S   K   I   P   F   H   L   D   D   N
901/301                                931/311
gcc gcc gct cgc gta ggt att cgc gcc tgg cca atc agc gtg acg ggg att aaa ccg gcg
 A   A   A   R   V   G   I   R   A   W   P   I   S   V   T   G   I   K   P   A
961/321                                991/331
gaa ggg ccg ttt act gcg cgc ggc tat cta cga gtc gat tat gat taa
 E   G   P   F   T   A   R   G   Y   L   R   V   D   Y   D   *
```

Amino acids 1-22 constitute the signal sequence cleaved from the mature protein (amino acids 23 to 335). Arrow indicates site of signal peptidase cleavage.

Figure 45: Construction of *fimH* Asd⁺ vectors
```
Primer1: FimH-NcoI (starting with amino acid 23)
5'- CAT GCC ATG GCA TGC ACG GTT TGC CGT AAT TCA AAC G-3'
Primer2: FimH₁₀₀-HindIII (starting with amino acid 122)
5'-GCC CAA GCT TA TTA ACG GGG CGG ATA AAA TAC GCC AGC-3'
Primer3: FimH-HindIII (starting with terminal codon)
5'- GCC CAA GCT TTT AAT CAT AAT CGA CTC GTA GAT AGC C-3'
```
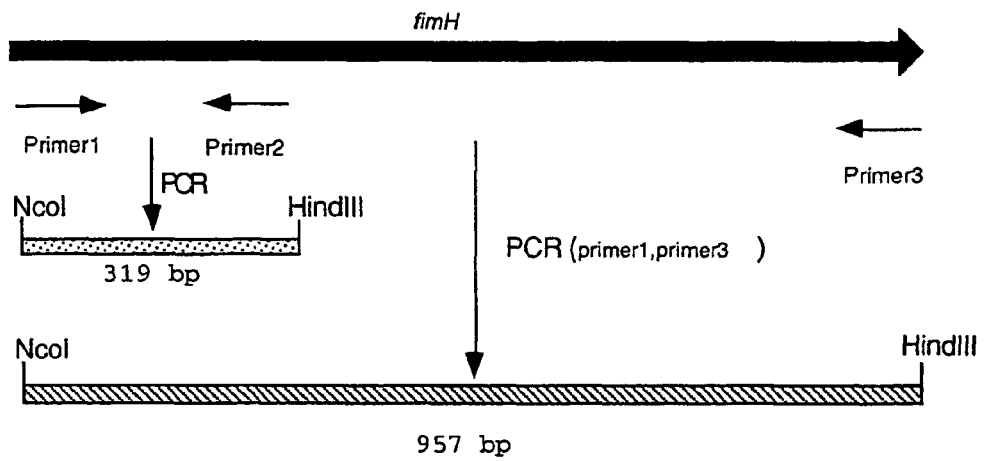
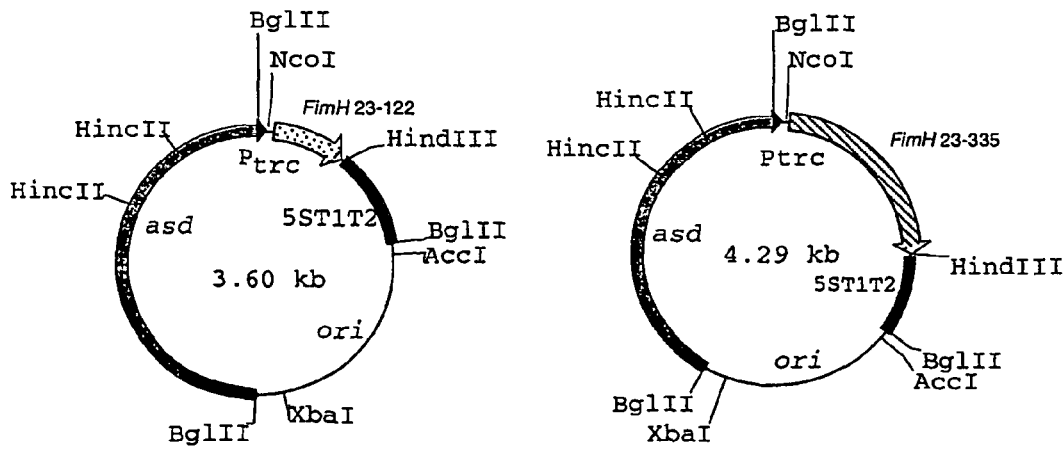

REGULATED ATTENUATION OF LIVE VACCINES TO ENHANCE CROSS-PROTECTIVE IMMUNOGENICITY

REFERENCE TO GOVERNMENT GRANT

This invention was made with government support under Grant No. 2001-02944 by the United States Department of Agriculture and/or Grant No. DE06669 and AI24533 by the National Institutes of Health. The United States government may have certain rights in the invention.

CROSS-REFERENCE TO RELATED APPLICATIONS

This application claims priority to provisional application serial number 60/372,616 filed Apr. 15, 2002 and to provisional application serial number 60/373,626 filed Apr. 18, 2002.

SEQUENCE LISTING

This application contains a paper copy of a Sequence Listing and appended hereto is a computer readable form of the same Sequence Listing, which is hereby incorporated by reference. The sequence listing information recorded in computer readable form is identical to the written sequence listing.

FIELD OF THE INVENTION

The invention relates generally to the field of recombinant attenuated bacteria, and more specifically to construction of bacterial strains which have the ability to induce immune responses that result in protection against infection by a diversity of bacterial serotypes and species.

BACKGROUND OF THE INVENTION

Citations to some documents may be indicated as numbers in parentheses; those numbers refer to the bibliography under the heading "Related Art" at the end of this section. Those references, as well as others cited in this document are hereby incorporated by reference.

Live bacterial vaccine vectors have been used successfully to elicit effective immune responses in order to prevent infection. Such vectors have been used to induce protective immunity against infection from homologous and heterologous bacterial strains. Live attenuated bacterial vectors are also useful for food safety, for example to prevent or reduce infection of livestock animals such as poultry or cattle by bacterial strains that are pathogenic to humans, such as *Salmonella* or *E. coli*.

The ability of live attenuated pathogenic bacteria of the Enterobacteriaceae family to colonize the gut-associated lymphoid tissue (GALT; Peyer's patches) and the deep tissues following oral administration is beneficial in that it stimulates all arms of the immune response, including mucosal, humoral and cellular immunities (Curtiss/Doggett/Nayak/Srinivasan 1996; Galan and Sansonetti 1996; Medina/Guzman 2001). Colonization of the intestinal tract by gram negative bacteria is dependent in part upon the expression of a number of surface antigens, including LPS O-antigen side chains, a diversity of fimbrial adhesins, flagella and certain outer membrane proteins. Thus, rough mutants, i.e., those with little or no O-antigen on their LPS, that have mutational lesions precluding synthesis of LPS O-antigen or parts of the LPS core tend not to colonize the intestinal tract (Roantree, 1971; Nnalue, 1990) and are defective in attaching to and invading intestinal cells and surviving in cells on the other side of the intestinal wall barrier. (25, 26). This latter phenotype is due to the fact that LPS is needed for bacteria to display resistance to killing by macrophages (27, 28) and also for the display of serum resistance (29, 30), that is, the ability to multiply in blood. In accord with these observations, rough mutants defective in LPS synthesis and thus defective in infection are among the most frequently isolated using signature tagged mutagenesis (31) and genes for LPS biosynthesis are very often up-regulated during infection as revealed by use of in vivo expression technology (32). Rough mutants have generally not been very effective when used as live vaccines. (33, 34, Hill abstract). Thus, it follows that an attenuated immunogenic live bacterial vaccine, to be safe and efficacious must not only display avirulence and not induce disease symptomology, but also must be able to reach, multiply and persist for a while in those lymphoid organs necessary to stimulate a protective immune response. Permanently rough strains cannot achieve the latter. The use of bacterial strains with mutations in the galE locus encoding UDP-galactose epimerase, an enzyme that interconverts UDP-glucose and UDP-galactose (UDP-gal) (35), has been considered as a way of overcoming the above limitation. UDP-gal is needed for the synthesis of both the LPS core and O-antigen in many bacterial strains. (36). When *Salmonella* galE mutants are provided low levels of galactose, they make normal LPS, but when deprived of galactose, they rapidly lose the ability to synthesize a complete LPS O-antigen and core. (37). One of the difficulties with galE mutants is that they are exceedingly sensitive to galactose (38, 39) and accumulate Gal-resistant mutants that are permanently rough and therefore not only avirulent, but also non immunogenic. Because of the LPS core defect, these galE mutants are somewhat hyper attenuated and do not induce high-level protective immunity. (40, 41). Another alternative to generate a reversibly rough phenotype is to make use of pmi mutants that have a mutation in the gene for phosphomannose isomerase (42), which interconverts mannose 6-phosphate and fructose 6-phosphate. Mannose 6-phosphate is then converted to GDP-mannose which is used for synthesis of O-antigen side chains (43). pmi mutants are not mannose sensitive and, as shown by Collins et al. (44), are attenuated and somewhat immunogenic. pmi mutants, when grown in media containing mannose, synthesize wild-type levels of LPS O-antigen side chains. In addition, pmi mutants do not lose the ability to synthesize LPS core.

Immune responses to iron-regulated outer membrane proteins (IROMPS) are known to be effective in preventing septicemic infection with enteropathogens. (Bolin 1987). Further, many bacterial serotypes and species in the Enterobacteriaceae family synthesize IROMPs and other proteins involved in iron uptake that share significant antigenic homology such that antibodies induced to proteins from one bacterial serotype or species are effective in binding to IROMPS and other iron uptake proteins from other serotypes and species. (Jun Lin 2001).

The fur gene encodes a repressor that represses all genes encoding IROMPS, in the presence of free iron. (Earhart 1996). When iron concentrations become low, as is the case in most animal host tissues beyond the intestinal wall barrier, the fur repression decreases and higher level expression of IROMPS and other fur-regulated genes needed to sequester iron is observed. fur mutants are attenuated when fed orally, giving a two to three log higher LD50 when administered either to mice (52) or day-of-hatch chicks. On the other hand, administering a fur mutant of *S. typhimurium* by the intraperitoneal route leads to only a slightly elevated LD50 compared to that of the wild-type parent. (53). In the intestinal tract iron is plentiful, both due to non absorption of dietary iron and the presence of iron from hemoglobin breakdown contributed into the intestinal tract as a component of bile. Green et al. 1968. It is also well known that iron, unless in a complex form, can promote the formation of damaging hydroxyl radicals, which may account, in part, for the toxicity of iron (51). Thus the high oral LD50 of fur mutants may be due to toxicity of free iron encountered in the intestinal tract. fur mutants are also acid sensitive (55) and are thus potentially sensitive to the gastric acidity barrier and to killing in acidified phagosomes in macrophages (56, 57). In summary, while fur mutant bacterial strains would display higher levels of IROMPs that likely would induce protective immunity, their avirulence properties when administered orally make them poor immunogens. So, while mutants unable to produce Fur are attenuated when delivered orally, because of substantial iron induced death they do not induce a significant immune response.

Members of the Enterobacteriaceae family cause a wide variety of human and animal diseases, including gram-negative sepsis, food poisoning, and typhoid fever. In addition, many farm animals are colonized with diverse enteric bacteria such as many serotypes of *Salmonella* without causing disease. Such bacteria are capable of transmission through the food chain to cause diseases in humans. Developing vaccines to prevent all the types of enteric diseases caused by bacterial enteric pathogens of diverse genera, species and serotypes and to prevent colonization by these diverse bacterial types in farm animals to enhance food safety would be prohibitively expensive. The incidence of these diseases and the prevalence of colonization of farm animals highlights the need for vaccines that would cross-protect against the numerous species and serotypes of enteric bacteria. Thus, it would be useful to develop attenuated bacterial vaccine strains that are capable of inducing cross-protective immunity.

RELATED ART

1. Tauxe, R N. 1991. *Salmonella*: a postmodern pathogen. J. Food Prot. 54:563-568.
2. Mead P. S., L. Slutsker, V. Dietz, L. P. McCaig, J. S. Bresee, C. Shapiro, P. M. Griffin, and R. V. Tauxe. 1999. Food-related illness and death in the United States. Emerg. Infect. Dis. 5:607-625.
3. CDC. 1996. Surveillance for food-borne disease outbreaks—United States, 1988-1992. MMWR CDC Surveillance Summaries 45:1-66.
4. Goodman, L., J. Segreti. 1999. Infectious diarrhea. Dis. Mon. 45:268-299.
5. Edwards, B. H. 1999. *Salmonella* and *Shigella* species. Clin. Lab. Med. 19:469-487.
6. LeMinor, L., and M. Y. Popoff. 1987. Designation of *Salmonella enterica* sp. nov., nom. rev., as the type and only species of the genus *Salmonella*. Int. J. Syst. Bacteriol. 37:465-468.
7. Food Safety and Inspection Service. 1999. *Salmonella* serotypes isolated from raw meat and poultry, Jan. 26, 1998 to Jan. 25, 1999. U.S. Department of Agriculture. http://www.fsis.usda.gov/OPHS/haccp/sero lyr.htm
8. Keller, L. H., C. E. Benson, K. Krotec, and R. J. Eckroade. 1995. *Salmonella enteritidis*, colonization of the reproductive tract and forming and freshly laid eggs of chickens. Infect. Immun. 63:2443-2449.
9. Keller, L. H., D. M. Schifferli, C. E. Benson, S. Aslam, and R. J. Eckroade. 1997. Invasion of chicken reproductive tissues and forming eggs is not unique to *Salmonella enteritidis*. Avian Dis. 41:535-539.
10. Gast, R. K., and C. W. Beard. 1990. Production of *Salmonella enteritidis*-contaminated eggs by experimentally infected hens. Avian Dis. 34:438-446.
11. Mason, J. 1994. *Salmonella enteritidis* control programs in the United States. Int. J. Food Microbiol. 21:155-169.
12. Trepka M. J., J. R. Archer, S. F. Altekruse, M. E. Proctor, and J. P. Davis. 1999. An increase in sporadic and outbreak-associated *Salmonella enteritidis* infections in Wisconsin: the role of eggs. J. Infect. Dis. 180:1214-1219.
13. Stadelman, W. J., R. K. Singh, P. M. Muriana, and H. Hou. 1996. Pasteurization of eggs in the shell. Poult. Sci. 75:1122-1125.
14. Curtiss, R. III, S. B. Porter, M. Munson, S. A. Tinge, J. O. Hassan, C. Gentry-Weeks, and S. M. Kelly. 1991. Nonrecombinant and recombinant avirulent *Salmonella* live vaccines for poultry, p. 169-198. In L. C. Blankenship, J. S. Bailey, N. A. Cox, N. J. Stern, and R. J. Meinersmann (eds.), Colonization Control of Human Bacterial Enteropathogens in Poultry. Academic Press, New York.
15. Porter, S. B., S. A. Tinge, and R. Curtis III. 1993. Virulence of *Salmonella typhimurium* mutants for White Leghorn Chicks. Avian Dis. 37:265-273.
16. Curtiss, R. III, and S. M. Kelly. 1987. *Salmonella typhimurium* deletion mutants lacking adenylate cyclase and cyclic AMP receptor protein are avirulent and immunogenic. Infect. Immun. 55:3035-3043.
17. Smerdou, C. A., Urniza, R., Curtiss III, and L. Enjuanes. 1996. Characterization of transmissible gastroenteritis coronavirus S protein expression products in virulent *S. typhimurium* Δcya Δcrp: persistence, stability and immune response in swine. Vet. Microbiol. 48:87-100.
18. Kennedy, M. J., R. J. Yancey Jr, M. S. Sanchez, R. A. Rzepkowski, S. M. Kelly, and R. Curtis III. 1999. Attenuation and immunogenicity of Δcya Δcrp derivatives of *Salmonella choleraesuis* in pigs. Infect. Immun. 67:4628-4636.
19. Hassan, J. O., and R. Curtis III. 1990. Control of colonization by virulent *Salmonella typhimurium* by oral immunization of chickens with avirulent Δcya Δcrp *S. typhimurium*. Res. Microbiol. 141:839-850.
20. Hassan, J. O., and R. Curtis III. 1994. Development and evaluation of an experimental vaccination program using a live avirulent *Salmonella typhimurium*, strain to protect immunized chickens against challenge with homologous and heterologous *Salmonella* serotypes. Infect. Immun. 62:5519-5527.
21. Hassan, J. O., and R. Curtis III. 1996. Effect of vaccination of hens with an avirulent strain of *Salmonella typhimurium* on immunity of progeny challenged with wild-type *Salmonella* strains. Infect. Immun. 64:938-944.
22. Hassan, J. O., and R. Curtiss III. 1997. Efficacy of a live avirulent *Salmonella typhimurium* vaccine in preventing colonization and invasion of laying hens by *Salmonella typhimurium*, and *Salmonella enteritidis*. Avian Dis. 41:783-791.
23. Roantree, R. J. 1971. The relationship of lipopolysaccharide structure to bacterial virulence, p. 1-37. In W. Kadis (ed.), Microbial toxins. New York, N.Y.: New York Acad. Press, Inc., New York, N.Y.
24. Nnalue, N. A., and A. A. Lindberg. 1990. *Salmonella choleraesuis* strains deficient in O antigen remain fully virulent for mice parenteral inoculation but are avirulent by oral administration. Infect. Immun. 58:2493-2501.

25. Stone, B. J., C. M. Garcia, J. L. Badger, T. Hassett, R. I. Smith, and V. L. Miller. 1992. Identification of novel loci affecting entry of *Salmonella enteritidis* into eukaryotic cells. J. Bacteriol. 174:3945-3952.
26. Finlay, B. B., M. N. Stambach, C. L. Francis, B. A. Stocker, S. Chatfield, G. Dougan, and S. Falkow. 1988. Identification and characterization of TnphoA mutants of *Salmonella* that are unable to pass through a polarized MDCK epithelial cell monolayer. Molec. Microbiol. 2:757-766.
27. Fields, P. I., R. V. Swanson, C. G. Haidaris, and F. Heffron. 1986. Mutants of *Salmonella typhimurium* that cannot survive within the macrophage are avirulent. Proc. Natl. Acad. Sci. USA 83:5189-5193.
28. Finlay, B. B., and J. H. Brumell. 2000. *Salmonella* interactions with host cells: in vitro to in vivo. Philos. Trans. R. Soc. Lond. B. Biol. Sci. 355:623-631.
29. Reeves, P. 1995. Role of O-antigen variation in the immune response. Trends Microbiol. 3:381-386.
30. Rowley, D. 1968. Sensitivity of rough gram-negative bacteria to the bactericidal action of serum. J. Bacteriol. 95:1647-1650.
31. Hensel, M., J. E. Shea, C. Gleeson, M. D. Jones, E. Dalton, and D. W. Holden. 1995. Simultaneous identification of bacterial virulence genes by negative selection. Science 269:400-403.
32. Mahan, M. J., D. M. Heithoff, R. L. Sinsheimer, and D. A. Low. 2000. Assessment of bacterial pathogenesis by analysis of gene expression in the host. Annu. Rev. Genet. 34:139-164.
33. Smith, H. W. 1956. The use of live vaccines in experimental *Salmonella gallinarum* infection in chickens with observations on their interference effect. J. Hygiene 54:419-432.
34. Muotiala, A. M., Hovi, P., H. Makela. 1989. Protective immunity in mouse salmonellosis: comparison of smooth and rough live and killed vaccines. Microbial Pathog. 6:51-60.
35. Lin, E. C. C. 1996. Dissimilatory pathways for sugars, polyols, and carbohydrates, p. 307-342. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (eds.), *Escherichia coli* and *Salmonella:* 2nd ed. Cellular and Molecular Biology. Washington D.C.: ASM Press, Washington D.C.
36. Raetz, C. R. H. 1996. Bacterial lipopolysaccharides: a remarkable family of bioactive macroamphiphiles, p. 1035-1063. In F. C. Neidhardt, R. Curtiss III, J. L. Ingraham, E C. Lin, K. B. Low, B. Magasanik, W. S. Reznikoff, M. Riley, M. Schaechter, and H. E. Umbarger (eds.), *Escherichia coli* and *Salmonella:* 2nd ed. Cellular and Molecular Biology. Washington D.C.: ASM Press, Washington D.C.
37. Germanier, R., and E. Furer. 1971. Immunity in experimental salmonellosis. Infect. Immun. 4:663-673.
38. Fukasawa, T., and H. Nikaido. 1959. Galactose-sensitive mutants of *Salmonella*. Nature, London. 184:1168-1169.
39. Fukasawa, T., and H. Nikaido. 1961. Galactose-sensitive mutants of *Salmonella* II. Bacteriolysis induced by galactose. Biochem. Biophys. Acta 48:470-483.
40. Nnalue, N. A., and B. A. Stocker. 1987. Test of the virulence and live vaccine efficacy of auxotrophic and galE derivatives of *Salmonella choleraesuis*. Infect. Immun. 55:955-962.
41. Clarke, R. C., and C. L. Gyles. 1986. Galactose epimeraseless mutants of *Salmonella typhimurium* as live vaccines for calves. Can. J. Vet. Res. 50:165-173.
42. Markovitz, A. R., J. Sydiskis, and M. M. Lieberman. 1967. Genetic and biochemical studies on mannose-negative mutants that are deficient in phosphomannose isomerase in *Escherichia coli* K-12. J. Bacteriol. 94:1492-1496.
43. Rosen, S. M., L. D. Zeleznick, D. Fraenkel, I. M. Wiener, M. J. Osborn, and B. L. Horecker. 1965. Characterization of the cell wall lipopolysaccharide of a mutant of *Salmonella typhimurium* lacking phosphomannose isomerase. Biochem. Z. 342:375-386.
44. Collins, L. V., S. Attridge, and J. Hackett. 1991. Mutations at rfc or pmi attenuate *Salmonella typhimurium* virulence for mice. Infect. Immun. 59:1079-1085.
45. Stanislavsky, E. S., T. A. Makarenko, E. V. Kholodkova, and C. Lugowski. 1997. R-form lipopolysaccharides (LPS) of Gram-negative bacteria as possible vaccine antigens. FEMS Immunol. Med. Microbiol. 18:139-145.
46. Nnalue, N. A. 1999. All accessible epitopes in the *Salmonella* lipopolysaccharide core are associated with branch residues. Infect. Immun. 67:998-1003.
47. Lüderitz, O., O. Westphal, A. M. Staub, and H. Nikaido. 1971. Isolation and chemical and immunological characterization of bacterial lipopolysaccharides, p. 145-233. In G. Weinbaum, S. Kadis, and S. Sjl (eds.), Microbial toxins, vol. 4. Bacterial endotoxins. Academic Press, Inc., New York.
48. Jansson, P. E., A. A. Lindberg, B. Lindberg, and R. Wollin. 1981. Structural studies on the hexose region of the core lipopolysaccharides from Enterobacteriaceae. Eur. J. Biochem. 115:571-577.
49. Olsthoorn, M. M., B. O. Petersen, S. Schlecht, J. Haverkamp, K. Bock, J. E. Thomas-Oates, and Hoist. 1998. Identification of a novel core type in *Salmonella* lipopolysaccharide. Complete structural analysis of the core region of the lipopolysaccharide from *Salmonella enterica* sv. Arizonae O62. J. Biol. Chem. 273:3817-3829.
50. Bolin, C. A., and A. E. Jenson. 1987. Passive immunization with antibodies against iron regulate outer membrane proteins protects turkeys from *Escherichia coli* septicemia. Infect. Immun. 55:1239-1242.
51. Earhart, C. F. 1996. Uptake and metabolism of iron and molybdenum, p. 1075-1090. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (eds.), *Escherichia coli* and *Salmonella:* 2nd ed. Cellular and Molecular Biology. Washington D.C.: ASM Press, Washington D.C.
52. Wilmes-Riesenberg, M. R., B. Bearson, J. W. Foster, and R. Curtis III. 1996. Role of the acid tolerance response in the virulence of *Salmonella typhimurium*. Infect. Immun. 64:1085-1092.
53. Garcia-del Portillo, F., J. W. Foster, and B. B. Finlay. 1993. Role of acid tolerance response genes in *Salmonella typhimurium* virulence. Infect. Immun. 61:4489-4492.
54. Green, R., R. Charlton, H. Seftel, T. Bothwell, F. Mayet, B. Adams, C. Flinch, and M. Layrisse. 1968. Body iron excretion in man. Am. J. Med. 45:336-353.
55. Foster, J. W., and H. K. Halt. 1992. Effect of *Salmonella typhimurium* ferric uptake regulator (fur) mutations on iron- and pH-regulated protein synthesis. J. Bacteriol. 174:4317-4323.
56. Alpuche-Aranda, C. M., J. A. Swanson, W. P. Loomis, and S. I. Miller. 1992. *Salmonella typhimurium* activates virulence gene transcription within acidified macrophage phagosomes. Proc. Natl. Acad. Sci. USA 89:10079-10083.
57. Rathman, M. M., D. Sjaastad, and S. Falkow. 1996. Acidification of phagosomes containing *Salmonella typhimurium* in murine macrophages. Infect. Immun. 64:2765-2773.
58. Hall, H. K., and J. W. Foster. 1996. The role of Fur in the acid tolerance response of *Salmonella typhimurium* is physiologically and genetically separable from its role in iron acquisition. J. Bacteriol. 178:5683-5691.

59. Englesberg, E, Irr J. Power, and N. Lee. 1965. Positive control of enzyme synthesis by gene C in the L-arabinose system. J. Bacteriol. 90:946-957.

60. Guzman, L. M., D. Belin, M. S. Carson., and J. Beckwith. 1995. Tight regulation, modulation, and high-level expression by vectors containing the arabinose PBAD promoter. J. Bacteriol. 177:4121-4130.

61. Lin, J., J. S. Hogan, and K. L. Smith. 1999. Antigenic homology of the inducible ferric citrate receptor (FecA) of coliform bacteria isolated herds with naturally occurring bovine intramammary infections. Clin. Diagn. Lab. Immunol. 6:966-969.

62. Baumler, A. J., A. J. Gilde, R. M. Tsolis, van der Velden, B. M. Ahmer, and F. Heffron. 1997. Contribution of horizontal gene transfer and deletion events to development of distinctive patterns of fimbrial operons during evolution of Salmonella serotypes. J. Bacteriol. 179:317-322.

63. van der Velden, A. W., A. J. Baumler, R. M. Tsolis, and F. Heffron. 1998. Multiple fimbrial adhesins are required for full virulence of Salmonella typhimurium in mice. Infect. Immun. 66:2803-2808.

64. Tsai, C. M., and C. E. Frasch. 1982. A sensitive silver stain for detecting lipopolysaccharides in polyacrylamide gels. Anal. Biochem. 119:115-119.

65. Hitchcock, P. J., and T. M. Brown. 1983. Morphological heterogeneity among Salmonella lipopolysaccharide chemotypes in silver-stained polyacrylamide gels. J. Bacteriol. 154:269-277.

66. Galan, J. E., and R. Curtiss III. 1990. Expression of Salmonella typhimurium genes required for invasion is regulated by changes in DNA supercoiling. Infect. Immun. 58:1879-1885.

67. Curtiss, R. III, S. M. Kelly, and J. O. Hassan. 1993. Live oral avirulent Salmonella vaccines. Vet. Microbiol. 37:397-405.

68. Zhang, X., S. M. Kelly, W. S. Bollen, and R. Curtiss III. 1997. Characterization and immunogenicity of Salmonella typhimurium SL1344 and UK-1 Δcrp and Δcdt deletion mutants. Infect. Immun. 65:5381-5387.

69. Zhang, X., S. M. Kelly, W. Bollen, and R. Curtiss III. 1999. Protection and immune responses induced by attenuated Salmonella typhimurium UK-1. Microb. 26:121-130.

70. Nakayama, K., S. M. Kelly, and R. Curtiss III. 1988. Construction of an Asd* expression cloning vector: Stable maintenance and high level expression of cloned genes in a Salmonella vaccine strain. Bio/Tech. 6:693-697.

71. Doggett, T. A., E. K. Jagusztyn-Krynicka, and R. Curtiss III. 1993. Immune responses to Streptococcus sobrinus surface protein antigen A expressed by recombinant Salmonella typhimurium. Infect. Immun. 61:1859-1866.

72. Hanahan, D. 1983. Studies on transformation of Escherichia coli with plasmids. J. Mol. Biol. 166:557-580.

73. Provence, D. L., and R. Curtiss III. 1994. Isolation and characterization of a gene involved in hemagglutination by an avian pathogenic Escherichia coli strain. Infect. Immun. 62:1369-80.

74. Provence, D. L., and R. Curtiss III. 1992. Role of crl in avian pathogenic Escherichia coli: a knockout mutation of crl does not affect hemagglutination activity, fibronectin binding, or Curli production. Infect. Immun. 60:4460-4467.

75. Pourbakhsh, S. A., M. Boulianne, B. Martineau-Doizé, C. M. Dozois, C. Desautels, and M. Fairbrother. 1997. Dynamics of Escherichia coli infection in experimentally inoculated chickens. Avian Dis. 41:221-233.

76. Dho-Moulin, M., J. F. van den Bosch, J. P. Girardeau, A. Bree, T. Barat, and J. P. Lafont. 1990. Surface antigens from Escherichia coli O2 and O78 strains of avian origin. Infect. Immun. 58:740-745.

77. Brown, P. K., and R. Curtis III. 1996. Unique chromosomal regions associated with virulence of an avian pathogenic Escherichia coli strain. Proc. Natl. Acad. Sci. USA 93:11149-11154.

78. PCR protocols: A Guide to Methods and Applications. 1990. M. A. Innis, D. H. Gelfand, J. J. Sninsky, and T. J. White, (eds.). Academic Press, Inc. San Diego.

79. Schmieger, H. 1972. Phage P22-mutants with increased or decreased transduction abilities. Mal. Gen. Genet. 119:75-88.

80. Kuo, T. T., and B. A. Stocker. 1970. ES18, a general transducing phage for smooth and nonsmooth Salmonella typhimurium. Virology. 42:621-632.

81. Newell, D. G., H. McBride, and A. D. Pearson. 1984. The identification of outer membrane proteins and flagella of Campylobacter jejuni. J. Gen. Microbiol. 130:1201-1208.

82. Ausubel, P. M., ed. 1988. Current Protocols in Molecular Biology. Wiley Interscience: New York, N.Y.

83. Hassan, J. O., S. B. Porter, R. Curtis III. 1993. Effect of infective dose on humoral immune responses and colonization in chickens experimentally infected with Salmonella typhimurium. Avian Dis. 37:19-26.

84. Bergey's Manual of Systematic Bacteriology, vol. 1. 1984. J. G. Halt, and N. R. Krieg (eds.). Williams and Wilkins, Baltimore, Md.

85. Vaerman, J. P. 1994. Phylogenetic aspects of mucosal immunoglobulins, p. 99-104. In Handbook of Mucosal immunology. Academic Press.

86. Peighambari, S. M., and C. L. Gyles. 1998. Construction and characterization of avian Escherichia coli cya crp mutants. Avian Dis. 42:698-710.

87. QIAGEN Product Guide 2000.

88. Crichton, P. B., D. E. Yakubu, D. C. Old, and S. Clegg. 1989. Immunological and genetical relatedness of type-1 and type-2 fimbriae in Salmonellas of serotypes Gallinarum, Pullorum and Typhimurium. J. Appl. Bacterial. 67:283-291.

89. Stentebjerg-Olesen, B., T. Chakraborty, and P. Klemm. 2000. FimE-catalyzed off-to-on inversion of the type 1 fimbrial phase switch and insertion sequence recruitment in an Escherichia coli K-12 fimB strain. FEMS Microbial Lett. 182:319-325.

90. Evans, D. G., D. J. Evans Jr, and W. Tjoa. 1977. Hemagglutination of human group A erythrocytes by enterotoxigenic Escherichia coli isolated from adults with diarrhea: correlation with colonization factor. Infect Immun. 18:330-337.

91. Low, D., B. Braaten, and M van derWoude. 1996. Fimbriae, p. 146-151. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (eds.), Escherichia coli and Salmonella: 2nd ed. Cellular and Molecular Biology. Washington D.C.: ASM Press, Washington D.C.

92. Boyd, E. F., and D. L. Hard. 1999. Analysis of the type I pilin gene cluster film. In Salmonella: its distinct evolutionary histories in the 5' and 3' regions. J. Bacterial. 181:1301-1308.

93. Korhonen, T. K. 1979. Yeast cell agglutination by purified enterobacterial pili. FEMS Microbial. Lett. 6:421-425.

94. Goldhar, J. 1995. Erythrocytes as target cells for testing bacterial adhesins, p. 43-50. In R. J. Doyle, and I. Ofek (eds.), Adhesion of Microbial Pathogens. Academic Press, San Diego.

95. Collinson, S. K., P. C. Doig, J. L. Doran, S. Clouthier, T. J. Trust, and W. W. Kay. 1993. Thin, aggregative fimbriae mediate binding of *Salmonella enteritidis* to fibronectin. J. Bacterial. 175:12-18.

SUMMARY OF THE INVENTION

The inventors have discovered that by combining, in a live attenuated derivative of an Enterobacteriaceae, a genetic construction that allows regulated expression of a regulatory protein such that antigenic proteins which are conserved among Enterobacteriaceae are expressed in vivo, and a means for regulatable synthesis of LPS O-antigens such that said O-antigens cease to be expressed in vivo, said live attenuated derivative has enhanced ability to induce cross-protective immunity against a diversity of gram negative pathogens. As used herein, the term "pathogen" refers to organisms that cause disease symptoms in an animal. A pathogen need not necessarily cause disease symptoms in the animal to which the live attenuated derivative is administered. For example, many *Salmonella* serotypes are not pathogens for chickens and swine, but persist commensally, and then become pathogens in humans when transferred through the food chain. Thus, the term pathogen as used herein would apply to such *Salmonella* serotypes.

The inventors have shown that the above described live attenuated derivatives are effective in colonizing in the intestinal tract of an individual and invading into lymphoid tissue such that a high-level immune response is induced which protects the individual from infection from a diversity of species or serotypes of bacterial pathogens. A further advantage of such a live attenuated derivative is that even when administered to an individual at exceedingly high doses, the risk of death is low.

In one embodiment of the invention, the regulatory protein is a ferric uptake regulator protein (Fur), which is encoded by the fur gene. The inventors have shown that by replacing the fur promoter with a regulatable promoter, the bacterial strain can be attenuated while still maintaining its immunogenicity. In a preferred embodiment of the invention, such regulated expression can be achieved by replacing the promoter for the fur gene with a metabolically controlled promoter such as that of the arabinose operon, the araCP$_{BAD}$ activator-repressor-promoter system. In other embodiments, the regulatory protein may be, for example, the protein encoded by the rpoS, phoPQ, dam, ompR, cya or crp gene.

Synthesis of LPS O-antigen can be regulated by any means known in the art. For example, synthesis of O-antigen may be regulated by mutation of or regulation of any of the genes in the rfb gene cluster, or by mutation or regulation of RfaH or the JUMPstart sequence located upstream of the O-antigen gene cluster, or by mutation of or regulation of any of the other genes involved in regulation of any of the genes of the O-antigen gene cluster. (Iredell 1998; Wang 1998; Schnaitman 1993; Klena 1998; Kelly 1996). In one embodiment of the invention, synthesis of LPS O-antigen is regulated by means of a mutation in a pmi gene, which encodes phosphomannose isomerase. Live attenuated derivatives harboring such a pmi mutation cannot synthesize LPS O-antigen side chains unless grown in the presence of free mannose. Thus, such mutants are unable to synthesize O-antigen side chains in vivo, as mannose in a free non-phosphorylated form is not prevalent in animal tissues. The presence of the pmi mutation leads to a gradual elimination of LPS O-antigen side chains in vivo, which then better exposes the LPS core and the IROMPs and other proteins involved in iron uptake, along with other surface proteins, which are conserved among genera and species within the Enterobacteriaceae family. Thus, the live attenuated derivative comprising the combination of the above described elements, when administered to an animal has enhanced ability to induce immune responses to IROMPs and other Fur regulated proteins and to the LPS core antigen to confer cross-protection against infection by diverse genera species and serotypes of Enterobacteriaceae. The term "comprising" or "comprise" is intended to be inclusive or open-ended and does not exclude additional, unrecited elements or method steps. By "comprising", it is meant that the named elements are essential, but other elements may be added and still form a construct within the scope of the claim.

Some embodiments of the invention may further comprise a means for decreasing the expression of antigenic proteins and carbohydrates that show a great degree of diversity among the Enterobacteriaceae. These embodiments have the advantage of directing the immune response of the host animal to the conserved antigens, such that the cross-protective immunity is enhanced. Examples of such non-conserved antigenic proteins and carbohydrates include the flagella, LPS O-antigens, and fimbriae. In one embodiment, the fliC or fljB genes, which encode flagella are mutated. In another embodiment, both the fliC and fljB genes are mutated. In other embodiments the deletion mutations in the fliC and fliB genes only delete regions encoding antigenic variable domains and retain constant flagellar domains that induce T-cell immunity and recruit an inate immune response by interaction of the flagellar constant domains with the TLR5 receptor.

BRIEF DESCRIPTION OF THE FIGURES

FIGS. 1A and 1B illustrate the construction of a suicide vector for transfer of ΔPfur223::TTaraCP$_{BAD}$fur deletion-insertion mutation.

FIG. 2 shows the ΔPfur223::TTaraCP$_{BAD}$fur deletion-insertion chromosomal construction.

FIG. 3 illustrates the construction of a suicide vector for pmi deletion.

FIG. 4 shows the chromosomal deletion for Δpmi-2426.

FIG. 5 demonstrates the reduction of LPS O-side chains in χ8650 as a function of time (hours) or numbers of generations of growth.

FIG. 6 demonstrates the outer membrane protein expression profile of ΔPfur223::TT araCP$_{BAD}$fur mutants grown in nutrient broth +/−arabinose.

FIG. 7 is a graphic illustration of colonization of Peyer's patches and spleens in 8-week-old female BALB/c mice as a function of time after oral inoculation with χ634 ΔPfur:: TTaraCP$_{BAD}$fur.

FIG. 8 is a graphic illustration of colonization of Peyer's patches and spleens in 8-week-old female BALB/c mice as a function of time after oral inoculation with χ8650 Δpmi-2426.

FIG. 9 is a graphic illustration of colonization of Peyer's patches and spleens in 8-week-old female BALB/c mice as a function of time after oral inoculation with χ8754 Δpmi-2426 ΔPfur223::araCP$_{BAD}$fur.

FIG. 10 illustrates the ability of χ8754, grown either in the presence or absence of mannose, to colonize the Peyer's patches and spleen of 8-week-old female BALB/c mice at designated intervals after oral inoculation.

FIG. 11 is a graphic illustration of the ability of serum antibodies collected from mice 30 days after oral inoculation with either χ8650 or χ8634 to react with the OMPs present in various *Salmonella* and *E. coli* strains grown in media containing excess iron such that the synthesis of IROMPs is minimal.

FIG. 12 is a graphic illustration of the ability of serum antibodies collected from mice 30 days after oral inoculation with either χ8650 or χ8634 to react with the IROMPS present in various *Salmonella* and *E. coli* strains grown in media substantially free of iron such that constitutive expression of fur-regulated proteins occurs.

FIG. 13 is a graphic illustration of colonization of day-of-hatch chicks as a function of time after oral inoculation with χ8754 Δpmi-2426 ΔPfur223::araCP$_{BAD}$fur.

FIG. 14 illustrates construction of the suicide vector for transfer of ΔfliC825 deletion mutation.

FIG. 15 illustrates construction of a suicide vector for transfer of ΔfljB217 deletion mutation.

FIG. 16 shows the ΔfliC825 (A) and ΔfljB217 (B) chromosomal deletion mutations.

FIG. 17 illustrates construction of a suicide vector for transfer of ΔfliC-Var mutation.

FIG. 18 illustrates construction of a suicide vector for transfer of ΔfliC 2426 mutation.

FIG. 19 shows S. typhimurium UK-1 chromosomal map for ΔfliC-Var and ΔfliC 2426 deletion mutations.

FIG. 20 shows the DNA nucleotide sequence of improved araC* P$_{BAD}$ region in pYA3624.

FIG. 21 shows the DNA and amino acid sequences of P$_{fur}$ and fur gene of S. paratyphi A.

FIG. 22 illustrates construction of the suicide vector to introduce new ΔPfur-33::TT araC P$_{BAD}$ fur deletion-insertion mutation.

FIG. 23 shows a chromosomal map of ΔPfur-33::TT araC P$_{BAD}$fur deletion-insertion mutation.

FIG. 24 shows the DNA sequence of the ΔPfur-33::TT araC* P$_{BAD}$fur.

FIG. 25 shows the DNA and amino acid sequences of P$_{rpoS}$, rpoS and flanking region of S. typhimurium and S. typhi.

FIG. 26 illustrates construction of suicide vector for introducing ΔPrpoS-183::TT araC P$_{BAD}$ rpoS deletion-insertion mutation.

FIG. 27 shows a chromosomal map of ΔPrpoS-183::TT araC P$_{BAD}$ rpoS deletion-insertion mutation.

FIG. 28 shows the DNA and amino acid sequences of the S. typhimurium P$_{phoPQ}$ and phoPQ and the flanking region.

FIG. 29 illustrates construction of the suicide vector for introducing ΔP$_{phoPQ}$-107::TT araCP$_{BAD}$ phoPQ deletion-insertion mutation.

FIG. 30 shows a chromosomal map of ΔP$_{phopQ}$-107::TT araC P$_{BAD}$PhoPQ deletion-insertion mutation.

FIG. 31 shows suicide vectors for introducing the ΔaraBAD23 and ΔaraE25 deletion mutations.

FIG. 32 illustrates construction of the suicide vector for introducing the Δ(gmd-fcl)-26 deletion mutation.

FIG. 33 shows a chromosomal map of the Δ(gmd-fcl)-26 deletion mutation.

FIG. 34 shows diagrams of the suicide vectors shown in Table 2.

FIG. 35 illustrates various deletion mutations after insertion into Salmonella chromosome.

FIG. 36 shows the DNA and amino acid sequences of sopB and the flanking region of the S. typhimurium chromosome.

FIG. 37 illustrates construction of the suicide vector for introducing the ΔsopB deletion mutation into the Salmonella chromosome.

FIG. 38 shows a chromosomal map of ΔsopB deletion mutation.

FIG. 39 shows diagrams of the suicide vectors for introducing ΔasdA16 into S. typhimurium and ΔasdA25 into S. paratyphi A and S. typhi strains.

FIG. 40 shows chromosomal maps of ΔasdA16 and ΔasdA25 deletion mutations.

FIG. 41 shows maps of Asd$^+$ vectors with pSC101, p15A, pBR and pUC origins of replication to regulate plasmid copy numbers.

FIG. 42 shows the nucleotide sequence of P$_{trc}$ and the multiple cloning sites (MCS) of Asd$^+$ vectors in FIG. 41.

FIG. 43 shows a diagram of the suicide vector for introducing ΔilvG3::TT araC P$_{BAD}$ lacI TT deletion-insertion mutation and map of ΔilvG3::TT araC $P_{BAD}$ lacI TT mutation in the *Salmonella* chromosome.

FIG. 44 shows the nucleotide and amino acid sequences of *S. typhimurium* fimH and FimH protein.

FIG. 45 illustrates construction of fimH $Asd^+$ vectors.

DESCRIPTION OF THE INVENTION

The invention is directed to live attenuated strains of Enterobacteriaceae that are capable of inducing cross-protective immunity to a diversity of Enterobacteriaceae species and serotypes. This objective has been achieved by the means and methods described herein.

The Enterobacteria family comprises species from the following genera, any of which are considered to be useful in practicing the claimed invention: *Alterococcus, Aquamonas, Aranicola, Arsenophonus, Brenneria, Budvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus, Yersinia, Yokenella*. Due to their clinical significance, *Escherichia coli, Shigella, Edwardsiella, Salmonella, Citrobacter, Klebsiella, Enterobacter, Serratia, Proteus, Morganella, Providencia* and *Yersinia* are considered to be particularly useful. Some embodiments of the instant invention comprise species of the *Salmonella* genera, as this genera has been widely and extensively studied and characterized.

The LPS of Enterobacteriaceae comprises three distinct domains: 1) the O-specific polysaccharide (O-antigen); 2) the core oligosaccharide (consisting of the inner and outer core oligosaccharides); and 3) the lipid A. LPS is both a major virulence factor and a target for protective immune responses. The core region of LPS is highly conserved, in contrast to the O-antigen which is the basis for distinguishing the various serotypes of many Enterobacteriaceae species. In *Salmonella*, for example, over 2,000 serotypes have been identified on the basis of the diversity of their O-antigen type and their flagella type. In contrast, those serotypes of *Salmonella* share only two closely related LPS core types.

The ability of Enterobacteriaceae to colonize the intestinal tract of animals is dependent upon, among other factors, the expression of a number of surface antigens, including LPS O-antigen side chains, a diversity of fimbrial adhesins, flagella and other outer membrane proteins. LPS O-antigens are antigenically diverse as between strains of Enterobacteriaceae, and are a major factor in the variable immune response of host organisms to different strains of bacteria. It is known in the art that bacterial strains defective in the ability to synthesize LPS O-antigen substantially lack the ability to colonize the intestinal tract and to attach to and invade intestinal cells and survive in cells on the other side of the intestinal wall (i.e., internal tissues).

Thus, the bacterial strains of the invention comprise a means for regulatable synthesis of LPS O-antigens, such that O-antigens are synthesized when the strain is grown in vitro, and O-antigens cease to be synthesized in vivo, i.e., when the bacterial strains are administered to an animal. LPS O-antigen synthesis is dependent on a host of genes, including the genes of the rfb gene cluster. Regulation of synthesis of LPS O-antigens can be achieved by any suitable means. In some embodiments of the invention, regulation is achieved by mutations to or regulation of genes involved in synthesis of the O-antigens.

In some embodiments, the pmi gene is mutated such that the gene product is not expressed. The pmi gene encodes phosphomannose isomerase, a sugar transferase which inter converts mannose 6-phosphate and fructose 6-phosphate. In the process of O-antigen synthesis, mannose 6-phosphate is then converted to GDP-mannose which is then used for synthesis of O-antigen side chains. Thus, bacterial strains with a mutation which renders the pmi gene inoperable fail to produce O-antigen side chains. However, when such mutants are grown on media containing mannose, they are able to produce wild-type levels of O-antigen side chains. This is advantageous because of the important role that the LPS, including the O-antigen side chains, plays in the colonization of the gut and deep tissues of the animal. When the strain is administered to the animal, where free non-phosphorylated mannose is no longer available, the strain ceases to synthesize O-antigen side chain and over the course of several generations the strain no longer has significant levels of O-antigen associated with the cell wall, thus exposing the LPS core to enhance the immune response to this highly conserved antigen. Therefore, another advantage of the pmi gene mutation is that the mutation does not affect the ability of the strain to synthesize LPS core. Thus, the mutant strain can be grown on media containing mannose to maintain wild-type expression of O-antigen and then when administered to an animal, will continue to express wild-type levels of LPS core while at the same time expression of the O-antigen side chains will be significantly diminished, resulting in enhanced immune response of the animal to the LPS core and diminished immune response to the O-antigen side chain.

Other means of regulating the synthesis of O-antigen side chains are expected to achieve the same advantages as described above with respect to the pmi mutation. Those of ordinary skill in the art will be able to devise other means of regulated synthesis of O-antigen side chains that meet the criteria of the invention based on the knowledge in the art of the process by which O-antigen is synthesized in Enterobacteriaceae. It is contemplated that those means are within the scope of the present invention. For example, the promoter for any of the rfb genes, which are needed for the synthesis of the LPS O-antigen, can be replaced with the araCP$_{BAD}$ activator-repressor-promoter system so that expression of the particular rfb gene is dependant on the presence of arabinose supplied in media during growth of the vaccine.

The bacterial strains of the invention also comprise a genetic construction that allows regulated expression of a regulatory protein, such that antigenic proteins or carbohydrates which are conserved among the Enterobacteriaceae are expressed in vivo. Among the proteins or carbohydrates expressed in the cell membrane and wall of Enterobacteriaceae, some have been shown to be conserved to varying degrees among the various genera and species. For example, the LPS core and iron regulated outer membrane proteins (IROMPs) have been shown to be antigenically conserved among the Enterobacteriaceae.

IROMPS are encoded by a number of genes, the expression of which is controlled by a repressor protein (Fur) encoded by the fur gene. In the presence of iron, such as in the intestinal lumen, Fur represses the expression of IROMPs. In the absence of iron, such as for example in most animal host tissues beyond the intestinal wall barrier (internal tissues), Fur repression ceases, and thus IROMPs and other Fur-regulated genes are highly expressed. This level of IROMP expression in vivo can be reduced by the presence of glucose and/or $H_2O_2$ by the activation of the fur gene promoter by the Crp and OxyR positive regulators, respectively, to cause transcription of the fur gene. This sythesis of Fur causes a reduced level of IROMP sythesis even in the absence of iron. While fur mutants have been shown to be attenuated when administered orally to animals, such fur mutants may be susceptible to iron toxicity in the intestinal lumen due to non absorption of dietary iron and the presence of iron from hemoglobin breakdown contributed into the intestinal tract as a component of bile. In addition, unless in a complex form, iron can promote the formation of damaging hydroxyl radicals, which may account in part for the toxicity of iron. Further, since fur has been shown to play a role in the acid tolerance of Enterobacteriaceae, fur mutants are potentially sensitive to the gastric acidity barrier and to killing in acidified phagosomes in macrophages. All of these factors contribute to the fact that while fur mutants would display high levels of IROMPs that induce cross protective immunity, the avirulence properties of such mutants make them poor immunogens.

Thus, some embodiments of the bacterial strains of the present invention comprise a genetic construction which allows for regulated expression of the fur gene, such that fur is expressed when the strain is grown in vitro, and in the intestinal lumen, but is not expressed when the bacterial strain is in the host tissue beyond the intestinal wall barrier. Thus, the bacterial strain exhibits wild-type repressed levels of IROMP expression during growth in vitro and during the initial stage of infection, i.e. when in the intestinal lumen. Then after colonization of the lymphoid organs beyond the intestinal wall barrier, the strain exhibits constitutive high-level expression of IROMPs and other Fur-regulated proteins independent of the presence of absence of iron, glucose or $H_2O_2$.

The regulated expression of the gene encoding a regulatory protein, structural protein or biosynthetic enzyme protein (as shown in the Examples) may be achieved by any means available in the art. For example, it is common practice to delete the wild type promoter associated with a particular gene and replace it with a promoter from the same or a different organism that is regulatable. In one embodiment of the present invention, the genetic construction is one in which expression of the fur gene is dependent upon the presence of arabinose. Arabinose can be supplied in culture media, and is also present in the intestinal tract of animals, as a component of plants which constitute a common part of animal diets. However, arabinose is not present in animal tissues beyond the intestinal wall barrier. This is achieved by replacing the fur promoter with the araCP$_{BAD}$ activator-repressor-promoter system. The araCP$_{BAD}$ activator-repressor-promoter is dependent on the presence of arabinose, which binds to the araC gene product to activate transcription from the P$_{BAD}$ promoter. So, when the araCP$_{BAD}$ activator-repressor-promoter is operatively linked to the fur gene, in place of the fur promoter, expression of the fur gene is then dependent on the presence or absence of arabinose. For example, when the bacterial strain harboring such a genetic construction is grown in media supplemented with arabinose, or alternatively when the strain is in the lumen of the intestinal tract of an animal where arabinose is present, the fur gene is expressed and the expression IROMPs and other fur regulated proteins is repressed. On the other hand, when such a bacterial strain invades the tissue on the other side of the intestinal wall barrier, where arabinose is absent, the fur gene is no longer expressed leading to high level of expression of all of the fur regulated proteins including IROMPs. The elimination of the fur gene promoter also eliminates any influence of either glucose or products of oxidative metabolism in reducing the level of synthesis of fur regulated proteins including IROMPs.

Some embodiments of the bacterial strains of the invention comprise mutations in genes that encode other antigenic proteins expressed on the surface of Enterobacteriaceae, but which proteins are not antigenically conserved among the genera and species of the Enterobacteriaceae family. Such mutations cause diminished expression of those proteins, such that the host immune response is focused on the conserved antigenic proteins and carbohydrate antigens, further enhancing cross-protective immunity. It is important that such mutations be selected such that the diminished expression of the particular gene product does not significantly inhibit the bacterial strain's ability to colonize the intestinal tract and invade and persist in the tissue beyond the intestinal wall barrier. Examples of other surface proteins that are not antigenically conserved among the Enterobacteriaceae include flagella, pili, and fimbriae among others. Some embodiments of the bacterial strains of the invention comprise genetic constructions that diminish the expression of flagella. In particular embodiments, the bacterial strains comprise mutations in the fliC or fljB genes, or both the fliC and fljB genes. Such mutations do not alter the ability of the bacterial strains to colonize the mucosal tissue of the animal or invade and persist in the tissue beyond the lumen of the intestine. It is expected, since the flagella are antigenically diverse among the Enterobacteriaceae, that such mutations will enhance the cross-protective immunity elicited by such strains upon administration to animals. This can be achieved by complete deletion of the fliC and fljB genes or by deleting only regions of the genes encoding antigenic variable domains. This enables retention of constant flagellar comains that induce T-cell immunity and recruit an innate immune response by interaction of the flagellar constant domains with the TLR5 receptor. The skilled artisan will appreciate that diminished expression of other surface proteins that are antigenically diverse will confer similar characteristics as described with respect to the fliC and fljB mutations, thus achieving the same advantages as those mutations.

In a particular embodiment, the bacterial strains of the invention comprise a mutation in the pmi gene which renders that gene inoperable. A particularly preferred embodiment comprises the Δpmi-2426 mutation, which is described below in the Examples. The strain further comprises a genetic construction wherein the native fur gene promoter has been replaced by the araCP$_{BAD}$ activator-repressor-promoter system. A particularly preferred embodiment comprises the ΔPfur223::TT araCP$_{BAD}$fur construction. A particularly preferred bacterial strain, which comprises the above mentioned genetic constructs is χ8754, the construction of which is described in detail in the Examples. The χ8754 strain exhibits wild-type levels of LPS O-antigen and wild-type repressed levels of IROMPs both during growth of the strain and during initial stages of infection of visceral organs whether administered orally or by course spray to young chickens. Then after colonization of visceral lymphoid organs, LPS O-antigen synthesis ceases and overexpression of IROMPs commences. Thus, this strain is attenuated, efficiently colonizes lymphoid tissues following oral administration to animals and induces high-level protective immunity to subsequent challenge with a plurality of wild-type Enterobacteriaceae.

In an alternative of the embodiment described immediately above, instead of mutating the pmi gene, the pmi promoter is replaced with the araCP$_{BAD}$ activator-promoter. Thus, only after several generations of growth in vivo would LPS O-antigen cease.

Other embodiments, as shown in Example 19, comprise construction of candidate vaccine strains with mutational alterations that prevent display of motility to access food sources, ability to produce exopolysaccharide capsules that enhance survival, ability to make components of the extracellular matrix that enhance Biofilm formation and survival, reduce survival to starvation stresses and uncouple the necessity of protein synthesis to display any trait to prevent sustained survival of the vaccine strain in vivo or following excretion into the environment.

Other embodiments comprise the design and construction of vaccine strains of S. typhimurium, S. paratyphi A and S. typhi to be used to immunize humans and to include mutations in such vaccines as described in Examples 20 and 21 to prevent vaccine induction of gastroenteritis in human vaccinees.

Other embodiments comprise means to use constructed vaccine strains to serve as antigen delivery vectors as described in Example 22, and to exhibit regulated delayed expression in vivo of protective antigens that are immunologically cross reactive and very similar on many enteric bacteria as described in Example 23, so as to enhance induction by the vaccine strain of cross-protective immunity to many enteric bacteria of differing serotypes and species.

The invention further comprises methods for inducing an immune response comprising administering any of the above described bacterial strains to an animal. Such bacterial strains may be administered by any means known in the art. Preferred methods of administration include, for example, oral administration, gastric intubation, or in the form of aerosols, for example by the whole-body spray method described in PCT publication WO 00/04920. Other methods of administration are also possible, for example by injection. Dosages required for induction of cross-protective immunity will vary, although routine experimentation will allow the skilled artisan to make such determinations. Pharmaceutical carriers, in which the bacterial strains are suspended are also known in the art.

Administration of the bacterial strains of the invention can be a single dose, or as is not uncommon, in a series of two or more doses. Such subsequent administrations of the bacterial strain are commonly referred to as boosters, and in many instances such boosters result in prolonged protection of the host animal.

The above disclosure describes several embodiments of the invention, and the examples below further illustrate the invention. The skilled artisan will recognize that other embodiments that provide the same advantages may also be employed in the practice of this invention. The scope of this invention is intended to be defined by the claims, and the description and examples are intended to be non-limiting.

EXAMPLES

Table 1 lists the bacterial strains referred to throughout the Description and Examples, and Table 2 lists the plasmids used in the following Examples.

TABLE 1

| | | Bacterial Stains | |
|---|---|---|---|
| Strain # | Strain | Phenotype/Genotype or | Reference/ Source |
| | | A. *Escherichia coli* | |
| DH5α | *E. coli* K-12 | Δ(lacZYA-arg F)U169 (φ80 lacZ ΔM15) glnV44 recA1 endA1 gyrA96 thi-1 relA1 hsdR17 | 1 |
| MGN-617 | *E. coli* K-12 | SM10 λpir ΔasdA4 Δzhf-2::Tn10 | 2 |
| χ289 | *E. coli* K-12 | F-prototroph | 3 |

TABLE 1-continued

Bacterial Stains

| Strain # | Strain | Phenotype/Genotype or | Reference/Source |
|---|---|---|---|
| χ6206 | E. coli O26:H11 | EPEC | S. Ashkenazi |
| χ6212 | E. coli K-12 | ΔasdA4 Δzhf-2::Tn10 derivative | DH5α |
| χ7122 | Avian E. coli | O78:K80:H9 | 4 |
| χ7235 | Avian E. coli TK3 | O1:K1:H7 | 5 |
| χ7302 | Avian E. coli MT512 | O2:K1:H+ | 6 |
| | B. Salmonella enterica | | |
| χ3201 | S. agona NR1 | wild-type group B (1, 4, 12) | 7 |
| χ3202 | S. albany NR2 | wild-type group $C_3$ (8, 20) | 7 |
| χ3203 | S. anatum NR3 | wild-type group $E_1$ (3, 10) | 7 |
| χ3206 | S. bredeney NR8 | wild-type group B (1, 4, 12, 27) | 7 |
| χ3210 | S. hadar NR14 | wild-type group $C_2$ (6, 8) | 7 |
| χ3212 | S. heidelberg NR99 | wild-type group B (1, 4, 5, 12) | 7 |
| χ3213 | S. infantis NR29 | wild-type group $C_1$ (6, 7) | 7 |
| χ3217 | S. montevideo NR35 | wild-type group $C_1$ (6, 7) | 7 |
| χ3220 | S. panama NR38 | wild-type group D (1, 9, 12) | 7 |
| χ3246 | S. choleraesuis | wild-type group $C_1$ (6, 7) | 8 |
| χ3339 | S. typhimurium SL1344 | hisG46 | 9 |
| χ3700 | S. enteritidis 4973 | wild-type group D (1, 9, 12) PT13A | 7 |
| χ3744 | S. typhi ISP1820 | wild-type group D (9, 12) | 10 |
| χ3761 | S. typhimurium UK-1 | wild-type group B (1, 4, 12) | 11 |
| χ3796 | S. gellinarium | wild-type group D (1, 9, 12) | C. Poppe |
| χ3847 | S. enteritidis Y-8P2 | wild-type group D (1, 9, 12) PT8 | 7 |
| χ3848 | S. enteritidis 27A | wild-type group D (1, 9, 12) PT8 | 7 |
| χ3850 | S. enteritidis B6996 | wild-type group D (1, 9, 12) PT13A | 7 |
| χ3851 | S. enteritidis | wild-type group D (1, 9, 12) PT4 | Curtiss Collection |
| χ3985 | S. typhimurium UK-1 | Δcya-12 Δcrp-11 | 11 |
| χ4235 | S. kentucky | wild-type group $C_3$ (8, 20) | Curtiss Collection |
| χ4433 | S. typhimurium F98 | wild-type group B (1, 4, 12) | 7 |
| χ4860 | S. dublin | wild-type group D (1, 9, 12) | C. Maddox |
| χ4971 | S. typhimurium UK-1 | fur-1 | 12 |
| χ8387 | S. paratyphi A | cryptic plasmid cured | ATCC #9281 |
| χ8407 | S. muenster | wild-type group $E_1$ (3, 10) | Curtiss Collection |
| χ8409 | S. senftenberg | wild-type group $E_4$ (1, 3, 19) | Curtiss Collection |
| χ8438 | S. typhi Ty2 | Cys, rpoS+ group D (9, 12) | 13 |
| χ8634 | S. typhimurium UK-1 | ΔPfur223::TT araC $P_{BAD}$ fur | Curtiss Collection |
| χ8650 | S. typhimurium UK-1 | Δpmi-2426 | χ3761 |
| χ8754 | S. typhimurium UK-1 | Δpmi-2426 ΔPfur223::TT araC $P_{BAD}$ fur | χ8634 |
| χ8600 | S. typhimurium SL1344 | ΔfliC825 hisG46 | χ3339 |
| χ8601 | S. typhimurium SL1344 | ΔfljB217 hisG46 | χ3339 |
| χ8602 | S. typhimurium SL1344 | ΔfliC825 ΔfljB217 hisG46 | |
| χ8702 | S. typhimurium SL1344 | ΔmlrA::tetAR | 14 |
| χ8844 | S. typhimurium UK-1 | Δend2311 | χ3761 |
| χ8857 | S. typhimurium UK-1 | ΔyhiR::TT | χ3761 |
| χ8865 | S. typhimurium UK-1 | ΔyhiR::TT Δend2311 | χ3761 |
| χ8874 | S. typhimurium UK-1 | Δpmi-2426 ΔPfur::araC$P_{BAD}$fur ΔfljB217 | χ8754 |
| χ8882 | S. typhimurium UK-1 | ΔrelA1123 | χ3761 |

[1]Hanahan, D. 1983. Studies on transformation of *Escherichia coli* with plasmids. J. Mol. Biol. 166: 557-580.
[2]Roland, K., R. Curtiss III, and D. Sizemore. 1999. Construction and evaluation of a ΔcyaΔcrp *Salmonella typhimurium* strain expressing avian pathogenic *Escherichia coli* O78 LPS as a vaccine to prevent air sacculitis in chickens. "Received the P. P. Levine Award from American Association of Avian Pathologists for best manuscript published in 1999." Avian Dis. 43: 429-441.
[3]Curtiss, R. III, L. J. Charamella, C. M. Berg, and P. E. Harris. 1965. Kinetic and genetic analyses of D-cycloserine Inhibition and resistance in *Escherichia coli*. J. Bacteriol. 90: 1238-1250.
[4]Provence, D. L., and R. Curtissi II. 1994. Isolation and characterization of a gene involved in hemagglutination by an avian pathogenic *Escherichia coli* strain. Infect. Immun. 62: 1369-80.
[5]Pourbakhsh, S. A., M. Boulianne, B. Martineau-Doize, C. M. Dozois, C. Desautels, and M. Fairbrother. 1997. Dynamics of *Escherichia coli* infection in experimentally inoculated chickens. Avian Dis. 41: 221-233.
[6]Dho-Moulin, M., J. F. van den Bosch, J. P. Girardeau, A. Bree, T. Barat, and J. P. Lafont. 1990. Surface antigens fron *Escherichia coli* O2 and O78 strains of avian origin. Infect. Immun. 58: 740-745.
[7]Hassan, J. O., and R. Curtiss III. 1994. Development and evaluation of an experimental vaccination program using a live avirulent *Salmonella typhimurium* strain to protect immunized chickens against challenge with homologous and heterologous *Salmonella* serotypes. Infect. Immun. 62: 5519-5527.
[8]Kelly, S. M., B. A. Bosecker, and R. Curtiss III. 1992. Characterization and protective properties of attenuate mutants of *Salmonella choleraesuis*. Infect. Immun. 60: 4881-4890.
[9]Gulig, P. A., and R. Curtiss III. 1987. Plasmid-associated virulence of *Salmonella typhimurium*. infect. immun. 55: 2891-2901.
[10]Frey, S. E., W. Bollen, D. Sizemore, M. Campbell, and R. Curtiss III. 2001. Bacteremia associated with live attenuated χ8110 *Salmonella enterica* serovar Typhi ISP1820 in healthy adult volunteers. Clin. Immunol. 101: 32-37.
[11]Curtiss, R. III, S. B. Porter, M. Munson, S. A. Tinge, J. O. Hassan, C. Gentry-weeks, and S. M. Kelly. 1991. Nonrecombinant and recombinant avirulent *Salmonella* live vaccines for poultry, p. 169-198. in L. C. Blankenship, J. S. Bailey, N. A. cox, N. J. Stern, and R. J. Meinersmann (eds.), Colonization Control of Human Bacterial Enteropathogens in Poultry. Academic Press, New York.
[12]Wilmes-Riesenberg, M. R., B. Bearson, J. W. Foster, and R. Curtiss III. 1996. Role of the acid tolerance response in the virulence of *Salmonella typhimurium*. Infect. immun. 64: 1085-1092.
[13]WO 99/25 387
[14]Brown P. K., C. M. Dozois, C. A. Nickerson, A. Zuppardo, J. Terlonge, and R. Curtiss III. 2001. MlrA, a novel regulator of curli (AgF) and extracellular matrix synthesis by *Escherichia coli* and *Salmonella enterica* serovar *Typhimurium*. Mol. Microbiol. 41: 349-363.

TABLE 2

Plasmids

| Plasmids | Description | Derivation/source |
|---|---|---|
| pBAD/His A, B, and C | N- or C-Terminal 6xHis Tag vector | Invitrogen |
| pCR-Blunt II | TOPO vector | Invitrogen |
| pDMS197 | SacB suicide vector | Curtiss collection |
| pRE112 | SacB suicide vector | Curtiss collection |
| pMEG-208 | Asd$^+$ vector with TT araC P$_{BAD}$ | Megan Health, Inc |
| pMEG-375 | SacB SacR Pir-dependent suicide vector | Megan Health, Inc |
| pMEG-855 | Suicide vector for ΔPfur223::TT araCP$_{BAD}$ fur | Megan Health, Inc |
| pYA3485 | Suicide vector for ΔaraE25 | Curtiss collection |
| pYA3492 | Suicide vector for ΔagfBAC811 | Curtiss collection |
| pYA3546 | Suicide vector for Δpmi-2426 | Curtiss collection |
| pYA3547 | Suicide vector for ΔfliC825 | Curtiss collection |
| pYA3548 | Suicide vector for ΔfljB217 | Curtiss collection |
| pYA3582 | 6xHis tagged FljB | Curtiss collection |
| pYA3583 | 6xHis tagged FliC | Curtiss collection |
| pYA3599 | Suicide vector for ΔaraBAD23 | Curtiss collection |
| pYA3629 | Suicide vector for Δ(gmd-fcl)-26 | Curtiss collection |
| pYA3652 | Suicide vector for ΔendA2311 | Curtiss collection |
| pYA3654 | Suicide vector for ΔyhiR36::TT | Curtiss collection |
| pYA3679 | Suicide vector for ΔrelA1123 | Curtiss collection |
| pYA3686 | Suicide vector for ΔbcsABZC2118 | Curtiss collection |
| pYA3687 | Suicide vector for ΔbcsEFG2319 | Curtiss collection |
| pYA3688 | Suicide vector for ΔadrA4118 | Curtiss collection |
| pYA3701 | Suicide vector for ΔfliC2426 | Curtiss collection |
| pYA3702 | Suicide vector for ΔfliC-Var | Curtiss collection |

Example 1

Construction of a Bacterial Strain with Arabinose-Dependant Regulation of the Fur Gene which in Turn Regulates Expression of Numerous Genes Enabling Uptake of Iron by Bacterial Cells

*S. typhimurium* fur mutants are completely attenuated for mice and chickens but are not very immunogenic. This is undoubtedly due to the fact that fur mutants constitutively express a diversity of genes resulting in very efficient uptake of iron that is quite prevalent in the intestinal tract due to dietary non-absorption of iron and due to the presence of iron as a breakdown product of hemoglobin secreted in bile into the duodenal contents of the intestine. Since high intracellular iron concentrations are toxic to bacteria, fur mutants do not survive very well in the intestinal tract and therefore are not very efficient in colonization of the GALT, which is necessary in order to be immunogenic. One way to circumvent this problem would be to have the fur gene expressed when the bacterial cells are present in the intestinal contents so that efficient colonization of the GALT can take place followed by the gradual cessation in synthesis of the fur gene product in vivo to result in an attenuated phenotype. In addition, the gradual constitutive expression of fur regulated genes would expose the immunized animal host to over expression of iron regulated outer membrane protein (IROMP) antigens as well as other proteins involved in the acquisition, transport and delivery of iron to the bacterial cells. Since many fur regulated gene products are closely related structurally among Gram-negative bacterial species, antibodies induced in an immunized animal host to the IROMPs and other fur regulated gene products of one bacterial species react with the homologous proteins expressed by other Gram-negative bacterial pathogens. It should be emphasized that synthesis of fur regulated gene products in vivo is essential for virulence since a major host defense mechanism is to sequester iron via transferrin, lactoferrin and other iron binding proteins so as to make iron unavailable to invading bacterial pathogens. Thus, antibody responses to these proteins are often protective in preventing successful infection of bacterial pathogens that succeed by in vivo multiplication. A corollary is that induction of high-level immune responses to the IROMPs and other fur regulated gene products is quite effective in inducing antibodies that are cross protective and prevent infection of an immunized animal host by a diversity of Gram-negative bacterial pathogens.

One means to achieve regulated expression of the fur gene is to replace the promoter for the fur gene, whose function is regulated by both iron concentration and glucose concentration via the process of catabolite repression, with a metabolically controlled promoter such as that of the arabinose operon. The araC P$_{BAD}$ activator-promoter is dependent on the presence of arabinose that binds to the araC gene product to activate transcription from the P$_{BAD}$ promoter. Thus, if the araC P$_{BAD}$ activator-promoter is used to replace the fur promoter and the structural gene for the fur gene left intact, expression of the fur gene will be dependent on the presence or absence of arabinose. Since arabinose is quite prevalent in plants, some free arabinose exists in the diets consumed by many animals and humans thus contributing to the continued expression of a fur gene operationally linked to the araC P$_{BAD}$ activator-promoter while bacteria remain in the intestinal tract. On the other hand, arabinose is absent in animal tissues and the fur gene product will cease to be synthesized and will thus be diluted out as a consequence of bacterial cell division. Thus, after several cell divisions, constitutive expression off fur regulated genes will commence leading to attenuation, on the one hand, and exposure of the immunized animal host to all the fur regulated protein antigens, on the other.

To achieve these objectives, primers 1 (SEQ ID NO:1) and 2 (SEQ ID NO:2) (FIG. 1-A) were used to PCR amplify a 545 bp fragment from the chromosome of *S. typhimurium* UK-1 χ3761 containing 321 bp upstream of their gene and 224 bp of the fur gene. This blunt-ended PCR amplified DNA fragment was cloned by blunt-end ligation into the pCR-BluntII-TOPO vector (FIG. 1-A, Table 2) which is designed to facilitate blunt-end ligation. The resulting plasmid pMEG-840 (FIG. 1-A) was subjected to an inverse PCR reaction using primers 3 (SEQ ID NO:3) and 4 (SEQ ID NO:4) (FIG. 1-A) to delete 140 bp containing the fur gene promoter from 161 to 22 bp upstream of the fur gene ATG start site. The product of this reaction was subjected to blunt-end ligation to yield pMEG-853 FIG. 1-A). The ΔP fur mutation of 140 bp possessed internal restriction sites for BglII and NheI separated by 4 bp that would permit insertion of the araC $P_{BAD}$ activator-promoter. pMEG-853 was digested with SpeI and EcoRV and the 472 bp fragment containing the ΔPfur mutation was cloned into the suicide vector pRE112 (FIG. 1-A; Table 2) that had been digested with XbaI and SmaI enzymes to yield pMEG-854 (FIG. 1-A; 1-B). It should be noted that the restriction enzymes SpeI and XbaI generate the same CTAG internal overlapping sticky ends and both EcoRV and SmaI generate blunt ended sequences to enable success in the cloning and ligation of the 472 bp sequence from pMEG-853 cloned into pRE112 to yield pMEG-854. pMEG-854 contains a 405 bp fragment containing a sequence upstream of the fur gene promoter fused to a sequence encompassing the Shine-Dalgarno sequence and beginning of the fur gene, which thus contains the ΔPfur mutation. Oligonucleotide primers 5 (SEQ ID NO:5) and 6 (SEQ ID NO:6) (FIG. 1-B) were used to PCR amplify the sequence from pMEG-208 (FIG. 1-B) containing a transcription terminator (TT) and the araC $P_{BAD}$ activator-promoter. This DNA fragment contains a BglII site and an XbaI site encoded in primer 6 (see FIG. 1). Since the XbaI site generates a CTAG overhang, it is hybridizable with DNA fragments cut with the NheI restriction enzyme that also generates a CTAG hybridizable sequence. The PCR amplified TT araC $P_{BAD}$ fragment from pMEG-208 was therefore digested with BglII and XbaI and cloned into pMEG-854 digested with BglII and NheI to yield the suicide vector pMEG-855 (FIG. 1-B).

pMEG-855 was transferred to the suicide vector donor strain MGN-617 (Table 1) that was mated with χ3761 (Table 1). Chloramphenicol-resistant transconjugants that had inherited the suicide vector into the chromosome by a single crossover event were selected by plating on L agar containing chloramphenicol. Ten recombinant colonies were selected and purified on L agar medium with chloramphenicol and individual colonies picked into 1.0 ml of L broth lacking chloramphenicol and incubated at 37° C. Following growth to approximately $10^8$ CFU, sucrose-resistant isolates were obtained by plating on CAS plates containing 5% sucrose but lacking arabinose. This procedure is selective for a second crossover event in which the wild-type fur promoter would be replaced with the TT araC $P_{BAD}$ activator-promoter that would cause fur gene expression to be dependent on the presence of arabinose. Colonies containing cells lacking the ability to synthesize the fur gene product have a 3 to 4 mm orange halo surrounding colonies whereas this orange halo is only 1 mm when cells are plated on CAS medium containing 0.2% arabinose. The ΔPfur223::TT araC $P_{BAD}$fur construction present in the stocked strain χ8634 is diagramed in FIG. 2.

Example 2

Generation of a Defined Deletion Mutation in the pmi Gene and Construction of *Salmonella typhimurium* Mutants with this Δpmi-2426 Mutation An 1881 bp *S. typhimurium* DNA sequence encompassing the pmi gene was PCR amplified from the *S. typhimurium* UK-1 χ3761 chromosome. As depicted in FIG. 3, oligonucleotide primers 7 (SEQ ID NO:7) and 8 (SEQ ID NO:8) were designed to amplify the 298 bp sequence 5' to the ATG start codon of the pmi gene to yield the N-flanking fragment. Similarly, oligonucleotide primers 9 (SEQ ID NO:9) and 10 (SEQ ID NO:10) were designed to amplify the 301 bp sequence 3' to the TAG stop codon of the pmi gene to yield the C-flanking fragment. The N-flanking and C-flanking DNA fragments (FIG. 3) were then digested with EcoRI, ligated with polynucleotide joining enzyme after which oligonucleotide primers 7 and 10 were used to amplify the ligated N-flanking and C-flanking fragments by PCR. The PCR amplified oligonucleotide was then digested to completion with KpnI and SacI and cloned into the suicide vector pMDS197 (Table 2) similarly digested with KpnI and SacI. The resulting recombinant suicide vector, pY3546, is depicted in FIG. 3. This suicide vector contains the N-flanking and C-flanking sequences adjacent to the pmi gene, which has been deleted with the 1176 base pair pmi gene replaced with an EcoRI recognition sequence.

The suicide vector pYA3546 was introduced by electroporation into the suicide vector donor strain MGN-617 (Table 1). This recombinant strain was then mated with the *S. typhimurium* UK-1 strain χ3761 (Table 1) and tetracycline-resistant transconjugants were selected that arose due to single cross over events integrating pYA3546 into the chromosome of χ3761. Ten tetracycline-resistant transconjugants were selected, purified by restreaking on tetracycline-containing medium and grown in tetracycline-free Luria broth as 1 ml cultures to an approximate density of $10^8$ CFU/ml. These cultures were plated in the presence of 5% sucrose to select for a second crossover event to excise the suicide vector from the chromosome but leave in its place the deletion of 1176 bp encoding the pmi gene. Individual isolates were tested for inability to ferment mannose on MacConkey-Mannose agar and one isolate designated χ8650 was stocked and the pmi allele designated pmi-2426. The chromosomal Δpmi-2426 mutation present in χ8650 is diagramed in FIG. 4 along with the genes flanking the deleted pmi mutation in the *S. typhimurium* chromosome.

Example 3

Introduction of Δpmi-2426 Mutation into χ8634

The suicide vector pYA3546 (FIG. 3) for introduction of the Δpmi-2426 mutation by allele replacement was introduced into MGN-617 (Table 1) and this strain mated with χ8634 possessing the ΔPfur223::TT araC $P_{BAD}$fur mutation. Tetracycline-resistant transconjugants were selected on L agar medium containing tetracycline and 0.2% arabinose. It should be noted, that strains with the ΔPfur223::TT araC $P_{BAD}$fur mutation grow rather poorly on medium without any added arabinose. Ten tetracycline-resistant transconjugants were purified by restreaking on L agar medium containing tetracycline and 0.2% arabinose. Individual colonies were picked into 1.0 ml of L broth containing 0.2% arabinose. When cultures reached approximately $1\times10^8$ CFU, sucrose-resistant isolates, in which a second crossover event had occurred, were selected by plating on L agar medium containing 5% sucrose and 0.2% arabinose. Sucrose-resistant isolates were picked and tested for sensitivity to tetracycline indicating loss of the suicide vector and for inability to ferment mannose by streaking on MacConkey-Mannose agar. One isolate having all of the correct phenotypic properties with regard to the presence of the Δpmi-2426 and ΔPfur223::TT araC $P_{BAD}$fur mutations was stocked as χ8754.

Example 4

Phenotypic Properties of χ8634, χ8650 and χ8754

χ8634 with the ΔPfur223::TT araC $P_{BAD}$fur mutation, χ8650 with the Δpmi-2426 mutation and χ8754 with both mutations were compared to the wild-type *S. typhimurium* UK-1 strain χ3761 for ability to ferment various carbohydrates contained at a 0.5% concentration in MacConkey agar. As indicated by the data in Table 3, all strains are unable to ferment lactose whereas χ8650 and χ8754 are unable to ferment mannose. All other sugars were fermented by all four strains.

TABLE 3

Carbohydrate fermentations[a]

| Strains/genotype | Carbohydrates | | | | | | | |
|---|---|---|---|---|---|---|---|---|
| | Lac | Glc | Man | Mal | Srl | Xyl | Ara | Fru |
| χ3761 wild-type | − | + | + | + | + | + | + | + |
| χ8634 ΔPfur223::TT araC $P_{BAD}$fur | − | + | + | + | + | + | + | + |
| χ8650 Δpmi-2426 | − | + | − | + | + | + | + | + |
| χ8754 Δpmi-2426 ΔPfur223::TT araC $P_{BAD}$fur | − | + | − | + | + | + | + | + |

[a]Bacterial strains were grown in L broth at 37° C. overnight and the cultures streaked to observe isolated colonies on MacConkey agar with 0.5% each of the sugars indicated. Plates were incubated overnight. Lac, lactose; Glc, glucose; Man, mannose; Mal, maltose; Srl, sorbitol; Xyl, xylose; Ara, arabinose; Fru, fructose; −, no fermentation; +, fermentation.

The same four strains were evaluated for production of the group B LPS O-antigen side chains and for presence of flagellar antigens using slide agglutination assays with antisera obtained from Difco Laboratories. The results presented in Table 4 are as expected. It should be noted that L agar, which contains yeast extract, contains a low concentration of mannose. Thus strains with the Δpmi-2426 mutation when grown in L broth or on L agar make a lower than usual level of O-antigen side chains than if grown in medium with added mannose but a higher amount than when grown in a medium totally devoid of mannose. For example, if the strains are grown in Nutrient broth or on Nutrient agar medium without added mannose, the amount of O-antigen side chains synthesized is very negligible as revealed by resistance of the strains to infection with bacteriophage P22 whose attachment to *S. typhimurium* is dependent on the presence of O-antigen side chains.

TABLE 4

Slide agglutination assays with *Salmonella* O and H anti-sera[a]

| Strains/genotype | Group B O antiserum factors 1, 4, 5, 12 | H antiserum polyA |
|---|---|---|
| χ3761 wild-type | +++ | +++ |
| χ8634 ΔPfur223::TT araC $P_{BAD}$fur | +++ | +++ |
| χ8650 Δpmi-2426 | ++ | +++ |
| χ8754 Δpmi-2426 ΔPfur223::TT araC $P_{BAD}$fur | ++ | +++ |

[a]Bacterial strains were grown on L agar without mannose and arabinose. A single colony of each of the strains was picked and suspended in buffered saline with gelatin (BSG) on a microscope slide, and mixed with 5 μl of the anti-serum. Agglutination reactions were observed and compared. ++- moderate agglutination; +++- high agglutination.

FIG. 5 presents the results of an experiment with χ8650 with the Δpmi-2426 mutation, which demonstrates that as a function of time or number of generations of growth in Nutrient broth medium in the absence of added mannose there is a gradual loss of LPS O-antigen side chains. This behavior is as expected and would be reproduced in vivo when a vaccine strain, after immunization of an animal host, enters visceral tissues which lack free non-phosphorylated mannose.

Based on the nature of mutational changes in χ8634 and χ8754, which both possess the ΔPfur223::araC $P_{BAD}$fur mutation, synthesis of IROMPs should be constitutive when those strains are grown in the absence of arabinose and absent when grown in the presence of arabinose. The synthesis of IROMPs should be unaffected by the presence or absence of arabinose during growth of χ3761 with the level of IROMPs dependant on the iron concentration in Nutrient broth. These predictions were evaluated by preparing overnight cultures of χ3761, χ8634 and χ8754 growing statically in 10 ml of Nutrient broth containing 0.2% arabinose at 37° C. The cultures were then diluted 1:1000 into 10 ml of prewarmed Nutrient broth with and without 0.2% arabinose and grown with aeration to a cell density of about $8 \times 10^8$ CFU/ml. The cultures were centrifuged at 5000 rpm at 4° C. for 15 min in a refrigerated Sorvall clinical centrifuge and the cell pellets suspended in 10 mM HEPES buffer. The bacterial suspensions were lysed by sonication with six 10 s pulses at 40 w. The sonicated suspensions were centrifuged at 15,600 rpm for 2 min at 4° C. The supernatant fluid was centrifuged again at 15,600 rpm for 30 min at 4° C. The cell membrane pellets were suspended in HEPES buffer and an equal volume of 2% Sarkosyl added. The suspension was incubated at room temperature for 30 min with gentile shaking. Next, the outer membrane aggregate was sedimented by centrifugation at 15,600 rpm for 30 min at 4° C. and the supernatant was discarded. The membrane pellets were washed with and resuspended in HEPES buffer. The samples were prepared for the SDS-PAGE analysis by adding equal amounts of 2× sample buffer and boiling the samples for 10 min. Lastly, the samples were centrifuged at 12,000 rpm for 1 min in a microfuge and loaded onto gels containing SDS and 10% polyacrylamide. Following electrophoresis, the gel was stained with Coomassie Brilliant Blue. The results are depicted in FIG. 6 and give the expected results based on the strain genotypes.

Example 5

Ability of Mutant Strains to Colonize Lymphoid Tissues in Mice

The ability of *S. typhimurium* χ8634 with the ΔPfur223::araC $P_{BAD}$fur mutation to colonize eight-week-old female BALB/c mice following oral inoculation of $10^9$ CFU was investigated. The bacteria were grown in Luria broth containing 0.2% arabinose to an $OD_{600}$ of approximately 0.8. Bacteria were sedimented by centrifugation and concentrated by suspension in buffered saline with gelatin (BSG) so that 20 μl would contain approximately $10^9$ CFU of bacteria. Groups of immunized mice were euthanized as a function of time after oral inoculation and the data pertaining to colonization of Peyer's patches and spleens are depicted in FIG. 7. It is evident that χ8634 is quite effective in colonization of lymphoid tissues whereas a strain with a deletion of the fur gene colonizes tissues at very much lower titers such that animals do not develop immunity to subsequent challenge with virulent wild-type *S. typhimurium*. Results from an experiment done the same way for the *S. typhimurium* strain χ8650 with the Δpmi-2426 mutation are presented in FIG. 8. In this case, bacteria were grown in Luria-Bertani broth with or without 0.5% mannose prior to inoculation into mice. There were no significant differences for the two growth conditions.

Results of two other experiments with the *S. typhimurium* χ8754 strain that possesses both the ΔPfur223::TT araC P$_{BAD}$fur and Δpmi-2426 mutations are represented in FIGS. 9 and 10. It is evident that χ8754 persists for a sufficient time in lymphoid tissues to induce immunity before almost disappearing by 42 days (FIG. 9). Results were not significantly different depending upon whether the cultures were grown in the presence or absence of mannose and arabinose prior to inoculation (FIG. 10). This result is anticipated in that Luria broth, as indicated above, contains yeast extract that possesses both free arabinose and free mannose at low concentrations. When strains are grown in Nutrient broth, the differences are magnified but growth of *Salmonella* vaccine strains in Nutrient broth leads to a lesser degree of colonization and a lower immunogenicity. Growth in Nutrient broth is thus not a preferred method of evaluation for attenuated live vaccines.

Example 6

Avirulence and Immunogenicity of *S. typhimurium* Strains with Δpmi-2426 and/or ΔPfur223::TT araC P$_{BAD}$ Fur Mutations Table 5 presents results of an experiment to evaluate the attenuation and immunogenicity of χ8634 with the ΔPfur223::TT araC P$_{BAD}$fur mutation. χ8634 was grown in Luria broth either without or with 0.2% arabinose to an OD$_{600}$ of about 0.8. Bacterial cells were sedimented by centrifugation and suspended in BSG to a density so that there would be about 1×10$^9$ CFU in a 20 μl sample. Female BALB/c mice were purchased at 7 weeks of age and maintained for one week in our animal facilities to acclimate prior to use in experiments. At eight weeks of age, food and water were removed for four hours prior to oral inoculation with 20 μl of χ8634 cells suspended in BSG at appropriate densities. Morbidity and mortality were observed for 30 days, after which, survivors were challenged with virulent wild-type *S. typhimurium* UK-1 χ3761 grown in Luria broth to an OD$_{600}$ of approximately 0.8. It is apparent from the results that growth in Luria broth without added arabinose conferred total avirulence and induced the highest level of protective immunity. Since Luria broth contains yeast extract, which contains arabinose, it is evident that addition of an extra 0.2% arabinose must cause synthesis of too much Fur protein such that the total repression of all fur-regulated genes must starve cells for iron so that they are less able to survive and colonize in the intestine and thus are less immunogenic. This result has been observed in other experiments and thus growth of strains in Luria broth without added arabinose will be preferred to optimize immunogenicity. If, on the other hand, χ8634 is grown in Nutrient broth, which lacks arabinose, the addition of arabinose to 0.1 or 0.2% is necessary to achieve good immunogenicity.

TABLE 5

Virulence and protection of *S. typhimurium* UK-1 ΔPfur223::TT araC P$_{BAD}$fur mutant χ8634 in 8-week-old female BALB/c mice following oral inoculation[a]

| Growth condition | Inoculating dose | Survivors/total | Challenge dose | Survivors/total after challenge |
|---|---|---|---|---|
| Luria broth | 1.4 × 10$^9$ | 4/4 | 1.4 × 10$^9$ | 4/4 |
|  | 1.4 × 10$^8$ | 4/4 | 1.4 × 10$^9$ | 4/4 |

TABLE 5-continued

Virulence and protection of *S. typhimurium* UK-1 ΔPfur223::TT araC P$_{BAD}$fur mutant χ8634 in 8-week-old female BALB/c mice following oral inoculation[a]

| Growth condition | Inoculating dose | Survivors/total | Challenge dose | Survivors/total after challenge |
|---|---|---|---|---|
|  | 1.4 × 10$^7$ | 4/4 | 1.4 × 10$^9$ | 4/4 |
|  | 1.4 × 10$^6$ | 4/4 | 1.4 × 10$^9$ | 3/4 |
|  | 1.4 × 10$^5$ | 4/4 | 1.4 × 10$^9$ | 2/4 |
| (Total) |  | 20/20 |  | 17/20 |
| Luria broth with 0.2% arabinose | 1.1 × 10$^9$ | 4/4 | 1.4 × 10$^9$ | 4/4 |
|  | 1.1 × 10$^7$ | 3/4 | 1.4 × 10$^9$ | 2/3 |
|  | 1.1 × 10$^6$ | 4/4 | 1.4 × 10$^9$ | 1/4 |
|  | 1.1 × 10$^5$ | 4/4 | 1.4 × 10$^9$ | 0/4 |
| (Total) |  | 15/16 |  | 7/15 |

[a]Bacteria were grown in Luria broth with or without 0.2% arabinose to OD$_{600}$ of ~0.8. Bacterial cells were collected by centrifugation and suspended in buffered saline with gelatin (BSG). Female BALB/c mice, 8-weeks-old, were orally inoculated with 20 μl of the bacterial suspension. Morbidity and mortality were observed for 30 days. Surviving mice were challenged 30 days after the initial inoculation with virulent wild-type UK-1 χ3761 grown in Luria broth. Morbidity and mortality observations were recorded daily for an additional 30 days postchallenge. Both inoculating and challenge doses were measured in CFU.

To evaluate the attenuation and immunogenicity of *S. typhimurium* χ8650 possessing the Δpmi-2426 mutation, bacteria were grown in Nutrient broth with or without 0.5% mannose and 0.5% glucose to an OD$_{600}$ of approximately 0.8. Bacterial cells were collected by centrifugation and suspended in a concentrated form in BSG so that a 20 μl sample would possess approximately 1×10$^9$ CFU. Female BALB/c mice were purchased at 7 weeks of age and maintained for one week in our animal facilities to acclimate prior to use in experiments. At eight weeks of age, food and water were removed for four hours prior to oral inoculation with χ8650 cells suspended in BSG at appropriate densities. Morbidity and mortality were observed for 30 days, after which, survivors were challenged with virulent wild-type *S. typhimurium* UK-1 χ3761 grown in Luria broth to an OD$_{600}$ of approximately 0.8. It should be noted that the vaccine strain was grown in Nutrient broth since it is almost devoid of mannose to determine the influence of O-antigen side chain synthesis on the initial invasiveness of the candidate vaccine strain. On the other hand, we have demonstrated in many past studies that growth in Luria broth leads to optimal expression of the phenotype that is conducive to attachment to and invasion into the GALT of both virulent as well as of attenuated *Salmonella* vaccine strains. The results of this experiment are presented in Table 6. It is evident that growth of the vaccine strain under conditions that enable synthesis of LPS O-antigen side chains leads to morbidity and mortality at high doses (i.e., 1.5×10$^9$ CFU). However, mice that survived these high doses without morbidity, acquired protective immunity to high doses of the challenge strain. χ8650 grown in medium to preclude synthesis of LPS O-antigen side chains were totally attenuated and induced a high level of protective immunity (Table 6).

TABLE 6

Virulence and protection of *S. typhimurium* UK-1 Δpmi-2426 mutant χ8650 in 8-week-old female BALB/c mice following oral inoculation[a]

| Growth condition | Inoculating dose | Survivors/total | Challenge dose | Survivors/total after challenge |
|---|---|---|---|---|
| Nutrient Broth + 0.5% Man + 0.5% Glc | 1.5 × 10$^9$ | 3/8 | 8.0 × 10$^8$ | 3/3 |
|  | 1.5 × 10$^8$ | 7/8[b] | 8.0 × 10$^8$ | 4/4 |

TABLE 6-continued

Virulence and protection of *S. typhimurium* UK-1 Δpmi-2426 mutant
χ8650 in 8-week-old female BALB/c mice following oral inoculation[a]

| Growth condition | Inoculating dose | Survivors/ total | Challenge dose | Survivors/ total after challenge |
|---|---|---|---|---|
| | $1.5 \times 10^7$ | 7/8 | $8.0 \times 10^8$ | 3/4 |
| | $8.0 \times 10^7$ | 3/3 | | |
| | $1.5 \times 10^6$ | 4/4 | $8.0 \times 10^7$ | 4/4 |
| | $1.5 \times 10^5$ | 4/4 | $8.0 \times 10^7$ | 4/4 |
| | | (25/32) | | (21/22) |
| Nutrient Broth: | $1.7 \times 10^9$ | 8/8 | $8.0 \times 10^8$ | 4/4 |
| | $8.0 \times 10^7$ | 4/4 | | |
| | $1.7 \times 10^8$ | 8/8 | $8.0 \times 10^8$ | 4/4 |
| | $8.0 \times 10^7$ | 4/4 | | |
| | $1.7 \times 10^7$ | 7/8 | $8.0 \times 10^8$ | 3/3 |
| | $8.0 \times 10^7$ | 4/4 | | |
| | $1.7 \times 10^6$ | 4/4 | $8.0 \times 10^7$ | 4/4 |
| | $1.7 \times 10^5$ | 4/4 | $8.0 \times 10^7$ | 2/4 |
| | | (31/32) | | (28/31) |

[a]Bacteria were grown in Nutrient broth with or without 0.5% mannose and 0.5% glucose to $OD_{600}$ of ~0.8. Bacterial cells were collected by centrifugation and suspended in buffered saline with gelatin (BSG). Female BALB/c mice, 8-weeks-old, were orally inoculated with 20 μl of the bacterial suspension. Morbidity and mortality were observed for 30 days. Surviving mice were challenged 30 days after the initial inoculation with virulent wild-type UK-1 χ3761 grown in Luria broth. Morbidity and mortality observations were recorded daily for an additional 30 days postchallenge. Both inoculating and challenge doses were measured in CFU.
[b]Three of the seven surviving mice (in one cage) appeared sick with loss of hair and were therefore not challenged.

We next investigated the attenuation and immunogenicity of χ8754, which possesses both the ΔPfur223::TT araC $P_{BAD}$ fur and Δpmi-2426 mutations. χ8754 was grown in Luria broth supplemented with 0.5% mannose and 0.2% arabinose to an $OD_{600}$ of approximately 0.8. Bacterial cells were concentrated by centrifugation and suspended in BSG such that a 20 μl inoculum would contain approximately $1\times10^9$ CFU. Eight-week-old female BALB/c mice that had been acclimated for a week were orally inoculated with 20 μl of inocula containing differing densities of χ8754 cells. All mice survived for 30 days as indicated by the results presented in Table 7. The surviving mice were challenged with $1.0\times10^9$ CFU of the wild-type virulent *S. typhimurium* UK-1 strain χ3761 and all but one mouse survived the challenge. In that we had found that χ8634 with the ΔPfur223::TT araC $P_{BAD}$ fur mutation displayed total attenuation and highest immunogenicity when grown in Luria broth lacking added arabinose and since we had observed less morbidity and mortality when χ8650 with the Δpmi-2426 mutation was grown in Luria broth without added mannose, it has become our practice to grow the doubly mutant strain in Luria broth without added mannose or arabinose. These growth conditions yield total attenuation to inoculation with high titers of the vaccine strain and induce the highest level of protective immunity to challenge with wild-type *S. typhimurium*.

TABLE 7

Virulence and protection of *S. typhimurium* UK-1 Δpmi-2426
ΔPfur223::TT araC $P_{BAD}$fur mutant χ8754 in 8-week-old
female BALB/c mice following oral inoculation[a]

| Strain | Inoculating dose | Survivors/ total | Challenge dose | Survivors/ total after challenge |
|---|---|---|---|---|
| χ3761 wild-type | | | $1.0 \times 10^7$ | 0/5 |
| χ8754 | $1.1 \times 10^9$ | 5/5 | $1.0 \times 10^9$ | 5/5 |
| Δpmi-2426 | $1.1 \times 10^8$ | 5/5 | $1.0 \times 10^9$ | 5/5 |
| ΔPfur223::TT araC $P_{BAD}$fur | $1.1 \times 10^7$ | 5/5 | $1.0 \times 10^9$ | 4/5 |

[a]Bacteria were grown in Luria broth supplemented with 0.5% mannose and 0.2% arabinose to $OD_{600}$ of ~0.8. Bacterial cells were collected by centrifugation and suspended in buffered saline with gelatin (BSG). Female BALB/c mice, 8-weeks-old, were orally inoculated with 20 μl of the bacterial suspension. Morbidity and mortality were observed for 30 days. Surviving mice were challenged 30 days after the initial inoculation with virulent wild-type UK-1 χ3761 grown in Luria broth. Morbidity and mortality observations were recorded daily for an additional 30 days postchallenge. Both inoculating and challenge doses were measured in CFU.

Example 7

Induction of Cross Protective Immunity to Challenge with Wild-Type *S. enteritidis*

Eight-week-old female BALB/c mice were orally inoculated with decreasing doses of χ8754 grown in Luria broth (without added mannose or arabinose) to an $OD_{600}$ of approximately 0.8 and suspended in BSG. In this experiment, immunized mice were challenged 30 days later with *S. enteritidis* strain χ3700 (phage type 13a) also grown in Luria broth to an $OD_{600}$ of approximately 0.8 and resuspended in BSG. Eighty percent of mice immunized with either the highest dose of χ8754 or with a dose of χ8754 that was 10-times less than the challenge dose of χ3700, survived challenge with χ3700 (Table 8). Mice immunized with a vaccine inoculum only 1% of the challenge inoculum were not protected (Table 8). It is therefore evident that there is a significant level of cross protective immunity induced by the group B *S. typhimurium* ΔPfur223::TT araC $P_{BAD}$fur Δpmi-2426 candidate vaccine strain to challenge with a wild-type group D *S. enteritidis* strain known to be capable of egg-transmitted disease in humans. Based on past results, it would be expected that the level of cross protective immunity would be further enhanced by a booster immunization seven or so days after the initial immunization.

TABLE 8

Cross protection in mice immunized with *S. typhimurium* UK-1 Δpmi-2426
ΔPfur223::TT araC$P_{BAD}$fur strain ☐8754 and challenged with
*S. enteritidis* wild-type χ3700[a]

| Strain | Inoculating dose | Survivors/ total | Challenge dose | Survivors/ total after challenge | MDD[b] |
|---|---|---|---|---|---|
| χ3700 | | | $1.2 \times 10^9$ | 0/5 | wild-type |
| χ8754 | $1.0 \times 10^9$ | 5/5 | $1.2 \times 10^9$ | 4/5 | 12 |

TABLE 8-continued

Cross protection in mice immunized with *S. typhimurium* UK-1 Δpmi-2426
ΔPfur223::TT araCP$_{BAD}$fur strain χ8754 and challenged with
*S. enteritidis* wild-type χ3700[a]

| Strain | Inoculating dose | Survivors/ total | Challenge dose | Survivors/ total after challenge | MDD[b] |
|---|---|---|---|---|---|
| Δpmi-2426 | $1.0 \times 10^8$ | 5/5 | $1.2 \times 10^9$ | 4/5 | 14 |
| Δfur223::TT araCP$_{BAD}$fur | $1.0 \times 10^7$ | 5/5 | $1.2 \times 10^9$ | 0/5 | 10.5 |

[a]Bacteria were grown in Luria broth to OD$_{600}$ of ~0. Bacterial cells were collected by centrifugation and suspended in buffered saline with gelatin (BSG). Female BALB/c mice, 8-weeks-old, were orally inoculated with 20 μl of the bacterial suspension. Morbidity and mortality were observed for 30 days. Surviving mice were challenged 30 days after the initial inoculation with wild-type *S. enteritidis* χ3700 grown in Luria broth. Morbidity and mortality observations were recorded daily for an additional 30 days postchallenge. Both inoculating and challenge doses were measured in CFU.
[b]MDD: Mean day of death.

Example 8

Induction of Serum Antibody Responses Against OMPs and IROMPs in Diverse Serotypes of *Salmonella* and in Several Strains of *E. coli*

Serum antibodies were collected 30 days after oral inoculation of mice with either χ8650 with the Δpmi-2426 mutation or χ8634 with the ΔPfur223::TT araC P$_{BAD}$fur mutation by retro orbital bleeding. Serum IgG antibodies to *Salmonella* and *E. coli* OMPs and IROMPs were quantitated by ELISA. Briefly, 96-well ELISA plates were coated with OMPs or IROMPs isolated from *Salmonella* and *E. coli* strains (see below). The plates were blocked with 1% BSA in PBS plus 0.1% Tween 20 (blocking buffer). Serum samples were pooled from 4 mice and diluted 1:400 in blocking buffer. A volume on 100 μl of each diluted sample was added in duplicate to the 96-well plates, incubated at 37° C. for 2 h and washed with PBS plus 0.05% Tween 20. The plates were then incubated with biotin-avidin-labeled goat anti-mouse IgG (1:1000 in blocking buffer) and alkaline phosphatase-labeled Extravidin (1:4000 in blocking buffer). p-nitrophenylphosphate (1 mg/ml) in 0.1 M diethanolamine buffer was used as a substrate. The absorbency of the color reaction was read at 405 nm with an automated ELISA reader.

The OMPs and IROMPs as the test antigens for ELISA were isolated from bacteria of various serotypes of *Salmonella* and *E. coli* (Table 1). The bacteria were grown in Luria broth plus 200 mM FeCl$_3$ to repress synthesis of IROMPs and in Luria broth plus 200 mM α,α'-dipyridyl to sequester iron and cause IROMP synthesis to be constitutive. Bacterial cells were collected by centrifugation and the cell pellets suspended in 10 mM HEPES buffer. The cell suspension was sonicated with six 10 s pulses at 40 w. The sonicated suspension was centrifuged at 15,600×g for 2 min at 4° C. The supernatant fluid was centrifuged again for 30 min at 4° C. The cell membrane pellets were suspended in HEPES buffer and an equal volume of 2% Sarkosyl added. The suspension was incubated at room temperature for 30 min with gentile shaking. The suspension was then centrifuged at 15,600×g for 30 min and the supernatant was discarded. The membrane pellets were washed with and re-suspended in HEPES buffer. The concentration of protein in each preparation was determined. Separate ELISA plates were coated with OMP and IROMP preparations (200 ng/well) from each strain used in the analysis. It should be noted that the IROMP preparations also contain OMPs.

It is evident from the data presented in FIG. 11 that both bacterial vaccines induced significant titers of antibodies that react with the OMPs present in serogroups C1, C2, C3, D and E1. In addition, significant antibody titers were induced to the OMPs of most of the *E. coli* strains with the lowest titers to the OMPs present in the totally attenuated laboratory *E. coli* K-12 strain χ289 (FIG. 11).

The same serum antibodies were used to determine the antibody titers against IROMPs obtained from the same bacterial strains used in the proceeding experiment. As revealed by the data in FIG. 12, both χ8650 and χ8634 induced substantial antibody responses to the IROMPs from all strains of *Salmonella* and *E. coli* evaluated. The results of these two experiments are in accord with the evidence for cross protective immunity as revealed by challenge of immunized mice with a heterologous *S. enteritidis* group D strain (Table 8).

Example 9

Attenuation of *S. typhimurium* Strains with Δpmi-2426 and ΔPfur::TT araC P$_{BAD}$ Fur in Day-Of-Hatch White Leghorn Chicks Results presented in Table 9 indicate that *S. typhimurium* strain χ8754 is completely attenuated when used to inoculate day-of-hatch chicks at doses in excess of $1 \times 10^9$ CFU. For these experiments, the day-of-hatch chicks were infected before being provided with either food or water. These white leghorn chicks are hatched in our animal facility from fertile eggs obtained from SPAFAS. Bacteria for infection are grown in Luria broth and concentrated in BSG in the same manner as used for experiments to infect mice as described above. In this experiment, the LD$_{50}$ for χ8754 was in excess of $4 \times 10^9$ (Table 9). The same result was observed with χ8754 grown in Luria broth without added mannose and arabinose (data not shown). However, some chicks survived infection with $1 \times 10^7$ CFU of the wild-type χ3761, a dose that is far in excess of the LD$_{50}$. This result is sometimes observed due to a very rapid stimulation of a protective innate immune response by the high inoculating dose of virulent bacteria. This type of response is seen more often in birds that are naturally more refractory to infection by *Salmonella* than in inbred mice. Results are also more variable since the chickens are out bred and we do not get fertile eggs from the same flock of breeders for each shipment from SPAFAS.

TABLE 9

Virulence of S. typhimurium UK-1 Δpmi-2426 ΔPfur223::TTaraC
P_{BAD} fur mutant χ8754 in day-of-hatch chicks following oral inoculation

| Strains/Genotype | Inoculation Dose (cfu) | Survivors/total | LD50 |
|---|---|---|---|
| χ8754/ΔPfur::araC PBADfur11 | 4.3 × 10$^9$ | 4/4 | >4 × 10$^9$ |
|  | 2.3 × 10$^9$ | 4/4 |  |
|  | 1.3 × 10$^9$ | 4/4 |  |
| χ3761/wild-type | 1.2 × 10$^7$ | 2/4 |  |

Example 10

Ability of Candidate Vaccine Strains to Colonize and Persist in Lymphoid Tissues of Vaccinated Chicks Day-of-hatch chicks were orally inoculated with the candidate vaccine strain χ8754 grown in L broth to an OD$_{600}$ of 0.8 and suspended in BSG. Groups of chicks were euthanized on various days after initial infection to quantitate the titers of χ8754 in the bursa of Fabricius, the spleen and in cecal contents. Results of these studies are presented in FIG. 13. The increases in titers at 28 days after inoculation were unusual and unexpected. However, in the evaluation of the ability of χ8754 to colonize mice, the titers dropped significantly after 28 days (FIG. 9).

Example 11

Introduction of ΔfliC825 and ΔfljB217 Mutations into the Candidate Vaccine Strain χ8754

The various Salmonella serotypes generally have genetic information to express two antigenically different flagellar antigens (a minority express only one) and employ a genetic switching mechanism for phase variation to express one or the other flagellar antigenic type. Since the flagellar antigens are very immunogenetic and since there is great diversity of antigenic flagellar types in enteric bacteria infecting the intestinal tract that do not exhibit a significant degree of antigenic similarity, we have deleted the genes for the S. typhimurium fliC and fljB flagellar antigens. This decision was based on the fact that antibodies to the FliC and FljB flagellar antigens would not be of significance in inducing cross protective immunity and that induction of immune responses to these antigens would compete with the induction of antibody responses to the common LPS core antigen or to the highly cross reactive OMP and IROMP surface protein antigens that are important for induction of cross protective immunity. The construction of the suicide vector pYA3547 for introduction of the ΔfliC825 mutation into the chromosome is shown in FIG. 14. The construction of the suicide vector pYA3548 for introduction of the ΔfljB217 mutation into the chromosome is shown in FIG. 15. The molecular genetic attributes of the ΔfliC825 and ΔfljB217 mutations upon introduction into the chromosome are depicted in FIG. 16. Both of these suicide vectors are transferred to MGN-617 (Table 1) and the constructed strains used for conjugational transfer of the suicide vectors to χ8754 possessing the Δpmi-2426 and ΔPfur::TT araC P$_{BAD}$fur mutations. In the first step, transfer by MGN-617 of pYA3547 to χ8754 followed by selection for chloramphenicol resistance yields recombinants with the suicide vector integrated into the chromosome. These chloramphenicol-resistant recombinants are then grown in L broth in the absence of chloramphenicol and subjected to selection for sucrose-resistant isolates by plating on L agar containing 5% sucrose. This selection results in loss of the integrated suicide vector by a second reciprocal crossing over event to often result in allele replacement with inheritance of the ΔfliC825 mutation in place of the wild-type allele. The ΔflgB217 allele is introduced in the same way starting with the transfer by MGN-617 of the suicide vector pYA3548 and its subsequent integration (by selecting for tetracycline resistance) into and then excision (by selecting for sucrose resistance) from the chromosome for allele replacement. This generated the S. typhimurium strain χ8874 (Table 1) that possesses the ΔflgB217 mutation in addition to the mutations present in the χ8854 parent (Table 1). Following construction, strains are evaluated to demonstrate the absence of motility and the absence of flagellar antigens by a negative slide agglutination test with the Difco antisera against Salmonella flagellar antigens used previously (see Example 4). The presence of all four mutational alterations can be validated by PCR analyses and conduct of tests for the phenotype associated with each mutation as described in previous examples.

Example 12

Evaluation of Induction of Cross Protective Immunity in Chickens

Experiments to evaluate induction of cross protective immunity against diverse Salmonella serotypes is by a slight modification of the methods worked out and described by Hassan and Curtiss (1994, Infect, Immun. 62:5519-5527). Day-of-hatch chicks are immunized orally with 10$^8$ CFU of the vaccine described in Example 11 above with a booster immunization of the same dose administered 10 days later. These chicks and groups of unimmunized chicks as controls are challenged with Salmonella of numerous serotypes as listed in Table 1. Vaccine and challenge strains are grown in Luria broth and resuspended in BSG before oral inoculation. Groups of five challenged birds are euthanized 7 and 14 days after challenge and the titers of the challenge strain in the bursa of Fabricius, spleen, liver, ovaries and in the contents of the small intestine (ileum) and cecum determined. To evaluate induction of cross protective immunity against APEC infection, the APEC challenge strains can be administered by injection into the caudal air sac or by intratracheal inoculation.

Example 13

Construction of Mutant Derivatives of Host-Specific Salmonella Serotypes for Use as Vaccines to Induce Cross Protective Immunity to Gram-Negative Enteric Pathogens in Swine, Cattle and Humans S. choleraesuis is a host-adapted Salmonella that predominantly infects swine. S. dublin is a host-adapted Salmonella that predominately infects cattle. S. paratyphi A and S. typhi are host-adapted Salmonella that predominantly infect humans. The suicide vectors and methods for introducing the Δpmi-2426 and ΔPfur::TT araC P$_{BAD}$fur mutations are the same as described in the Examples given above. Each of these Salmonella serotypes possesses unique genes for the predominant flagellar antigens. Therefore, specific suicide vectors based on DNA sequence information for the flagellar genes in each of these serotypes is used to generate deletions for both flagellar antigen genes in each of the serotypes. The S. choleraesuis χ3246, S. dublin χ4860, S. paratyphi A χ8387 and S. typhi χ3744 and χ8438 strains that are altered by these genetic manipulations are listed in Table 1. The presence of each of the mutations can be ascertained by PCR analyses and testing for the specific phenotype associated with each mutation. Difco antisera is used to verify the presence of the appropriate group A, C1 or D O-antigens. The S. choleraesuis and S. dublin vaccines can initially be evaluated for induction of cross protective immunity in mice using challenge of immunized mice with a diversity of Salmonella strains of different serotypes (Table 1) as well as with other gram-negative enteropathogens. Subsequent evaluations would use pigs and calves to substantiate induction of cross protective immunity by the candidate S. choleraesuis and S. dublin vaccines, respectively. The S. paratyphi A and S. typhi candidate vaccines will be evaluated in human volunteers since there is no suitable animal model.

Example 14

Elimination of Serotype-Specific Flagellar Antigens while Retaining the Flagellar Constant Domains of FliC that Serve as a Pathogen-Associated Molecular Pattern (PAMP) to Trigger an Innate Immune Response by Specific Interaction with the Toll-Like Receptor 5 (TLR5)

Although eliminating the ability of vaccine strains designed to induce cross-protective immunity to induce immune responses to serotype-specific flagellar antigens as outlined in Example 11 is logical, these flagellar antigens, especially FliC, contain very strong T-cell epitopes (Cookson and Bevan, 1997, J. Immunol. 158:4310-4319) and thus might be important in inducing cellular immunity against Salmonella that would be protective against infection by diverse Salmonella serotypes. Potentially more important, flagella on bacteria serve as one of the pathogen-associated molecular patterns (PAMPs) and specifically trigger an innate immune response by their specific interaction with the toll-like receptor 5 (TLR5) (Hayashi et al., 2001, Nature 410: 1099-1103). It has recently been determined for the E. coli FliC protein that elimination of the central variable serotype-specific domains with retention of the N-terminal and C-terminal α-helical constant domains permits TLR5 recruitment and IL-8 production (Donnelly and Steiner, 2002, J. Biol. Chem. 277:40456-40461). Importantly, the flagellar T-cell epitope is contained within the conserved amino acid sequences of the flagellar antigens (Joys et al., 1993, Infect. Immun. 61:1146-1148; McSorley et al., 2000, J. Immunol. 164:986-993). We have therefore redesigned the deletion mutation for the flagellar fliC gene so that the modified fliC gene will no longer have any variable domains but will retain the N-terminal and C-terminal constant domains forming a conservative flagellar structure capable of interacting with TLR5 to stimulate the innate immune response and also in inducing cellular immune responses. We will use this mutation, ΔfliC-Var (minus variable region of fliC gene), in conjunction with the complete deletion mutation of the fljB gene, ΔfljB217. FIG. 17 diagrams the construction of the suicide vector (listed in Table 2) for delivery into the chromosome of the ΔfliC-Var deletion mutation that deletes the variable FliC flagellar amino acid domains. FIG. 17 also lists the oligonucleotide primers needed to generate the ΔfliC-Var mutation.

As described in Example 10 and diagramed in FIG. 14, we had constructed a suicide vector to introduce the ΔfliC825 mutation into the chromosomes of attenuated Salmonella vaccine strains. In this construction, we deleted 1380 bp of the 1488 bp encoding the entire fliC gene with short coding sequences for the N-terminal and C-terminal ends of FliC protein remaining. We have therefore constructed the suicide vector (Table 2) for the improved ΔfliC2426 mutation (FIG. 18) that deletes the entire coding sequence of the fliC gene. We will hereafter use this ΔfliC2426 mutation in strains to compare with the ΔfliC-Var mutation that retains the PAMP attributes but deletes serotype-specific flagellar antigen domains.

FIG. 19 diagrams the chromosomal ΔfliC-Var and ΔfljBC2426 mutations. (The ΔfljB217 mutation is diagramed in FIG. 16.) These mutations can be transferred to other Salmonella vaccine strains being constructed using the methods described by Kang et al (2002, J. Bacteriol. 184:307-312). As listed in Table 1, we have constructed recombinant pBAD/His vectors that generate production of His-tagged FliC and His-tagged FljB proteins and have purified these proteins by standard methods using nickel columns. These purified proteins have been used to generate anti-flagellar antibodies in rabbits that react with intact flagella possessing the serotype-specific antigenic determinants but should fail to interact with flagella that retain the constant domains but lack the variable amino acid sequences necessary for serotype specificity. To further complete this analysis, a His-tagged FliC-Var protein lacking the variable domains will be constructed by PCR cloning of the mutated sequences from the suicide vector diagramed in FIG. 17 into the pBAD/His vector (Table 2) and the protein purified to demonstrate that this protein does not significantly react with antibodies raised against the intact FliC protein but is able to interact with Caco-2 cells to elicit production of IL-8 (Donnelly and Steiner, 2002, J. Biol. Chem. 277:40456-40461).

Example 15

Method for Assessing Induction of Antibodies by Candidate Vaccine Constructions that Possess the Abilities to Interact with Surface Antig ns on Salmonella enterica Isolates of Divers Serotyp s and Other Closely Related Strains of Enterobacteriaceae Since quantitative antibody titers against isolated bacterial OMPs and IROMPs could represent antibodies that react, in part, with antigenic determinants that are masked in the intact bacterial cells, such antibody titers might be somewhat misleading as an indication of the ability of candidate vaccines to induce antibodies that would be cross reactive in a protective way against diverse enteric bacteria. For this reason, we have modified and refined for our use a quantitative ELISA to accurately measure antibodies that recognize whole live as well as whole killed bacteria of diverse serotypes and species. (see Mowat and Reed, 1994, In Current Protocols in Immunology, Gligan et al., eds., John Wiley and Sons, Inc., pp. 2.0.1-2.11.12; Marcjanna et al., 2001, Vet. Microbiol. 78:61-77). In this modified ELISA method, varying concentrations of washed bacteria ($10^5$ to $10^9$ CFU) are reacted with various dilutions of non-immune (as a control) and immune sera (diluted 1:100 to 1:3,200) in a crisscross serial dilution titration analysis. The S. enterica serotypes and E. coli strains used to collect the data in FIGS. 11 and 12 (Example 8) are used in these analyses as well as additional bacterial strains available to us (Table 1). The antibody titer determinations from such studies can be correlated with animal studies to evaluate the ability of candidate vaccines to induce cross protective immunity to viable pathogenic challenge strains. These studies will establish the antibody titers necessary as a correlate of inducing protective immunity and thus will eliminate the need for using vast numbers of animals immunized with candidate vaccines and challenged with a very large diversity of enteric bacterial pathogens. This method that we have developed will permit vaccine evaluation to be more economical and very much reduce the need for extensive animal experimentation, which would also be very costly. In addition to this modified whole-cell ELISA method, with either live or whole killed bacteria serving as antigens, we can also employ indirect immunofluorescence microscopy to determine whether antibodies in sera of animals immunized with candidate vaccines are reactive against surface bacterial antigens as visualized with intact bacteria.

Example 16

Construction of a New ΔPfur::TT araC $P_{BAD}$fur Deletion-Insertion Mutation with Tighter araC $P_{BAD}$ Regulation for Use in S. paratyphi A and S. typhi Vaccine Constructions Vaccine of the GALT. Because of these properties, *Salmonella* vaccine strains with rpoS mutations, although attenuated, are not very immunogenic and therefore are not very efficacious in inducing protective immunity either against *Salmonella* or against protective antigens specified by cloned genes present in recombinant attenuated *Salmonella* vaccines. These negative attributes associated with the presence of rpoS mutations in vaccine strains are detailed in U.S. Pat. No. 6,024,961 and U.S. Pat. No. 6,383,496 that also describe means to identify, select and/or construct vaccine strains that display wild-type RpoS+ phenotypes. Since the presence of a rpoS mutation in a vaccine strain reduces initial colonization of the GALT, there is also a reduced colonization of internal lymphoid tissues such as the mesenteric lymph node, liver and spleen that serve as major effectors sites for inducing immune responses (see Nickerson and Curtiss, 1997, Infect. Immun. 65:1814-1823). Replacement of the promoter for the rpoS gene with the improved tightly regulated araC $P_{BAD}$ activator-promoter sequence (FIG. 20) for fusion to a promoter-less rpoS gene would enable synthesis of the rpoS gene product when the vaccine strain is grown in the presence of arabinose as would be the case for growth of the vaccine strain prior to oral immunization of an immunized individual. Such a vaccine strain would therefore contain the RpoS regulatory protein and be able to express all RpoS-regulated genes necessary for efficient invasion of M cells and colonization of the GALT. Since arabinose is not present in animal tissues, further synthesis of the rpoS gene product would cease and gradually RpoS would be reduced in concentration either due to cell division of the vaccine strain and/or proteolytic breakdown of the RpoS protein. In this manner, the attenuation associated with a non functioning or non expressing rpoS gene would be delayed until the vaccine strain had efficiently colonized internal lymphoid tissues after which the vaccine strain would become defective in responding to starvation conditions and importantly to stresses encountered in vivo. In addition, as described below in Example 19, the rpoS gene product is necessary for the expression of genes for synthesis of thin aggregative fimbriae, encoded by the afg genes, and cellulose, encoded by the bcs genes, that collectively constitute an extracellular matrix that is necessary for *Salmonella* to synthesize biofilms and survive in various environments into which a vaccine strain might be excreted. The fact that vaccine strains with the inactive rpoS gene would not survive well in stationary phase and during starvation would enhance the benefit of using a regulated delayed non expression of the rpoS gene to provide a biological containment attribute that would diminish vaccine survival in nature and thus decrease the likelihood for non intentional immunization of individuals either not intended or not electing to be immunized. FIG. 25 provides DNA sequence information for the wild-type *S. typhimurium* 14028 and *S. typhi* CT18 rpoS genes (that have identical amino acid sequences) with their promoters and flanking sequences and indicates the nucleotide sequences encompassing the promoter of the rpoS gene ($P_{rpoS}$) (−12 to −48 from the ATG start of the rpoS gene) that will be deleted. FIG. 20 provides the DNA sequence information for the improved, tightly regulated araC $P_{BAD}$ sequence to be used to replace $P_{rpoS}$. FIG. 26 diagrams the construction of the suicide vector for introduction of the ΔPrpoS-183::TT araC $P_{BAD}$ rpoS insertion-deletion mutation into the chromosome of *Salmonella* vaccine strains. It should be noted that the T4 ipIII transcription terminator (TT) sequence is used after the C-terminus of the outwardly expressing araC gene so that potential transcription into adjacent genes does not result in unpredictable consequences for the vaccine strain such as its further attenuation. The uses of TT sequences for this purpose and as a means of attenuation of vaccine strains are fully described in a patent application filed Oct. 12, 2000 entitled "Microbes having an attenuating mutation comprising a transcription terminator" (U.S. Ser. No. 09/689,123). The deletion-insertion mutation in the chromosome is diagramed in FIG. 27 and this mutation can be moved into other vaccine strains using the transductional method described by Kang et al. (2002, J. Bacteriol. 184:307-312).

*Salmonella* strains with ΔphoP and/or ΔphoPQ mutations are highly attenuated and induce high-level protective immunity as reported by Galan and Curtiss (1989, Microbial Pathogen. 6:433-443) and as detailed in U.S. Pat. No. 5,424,065 and EUR 0,465,560B1. Nevertheless, it was originally observed (Galan and Curtiss, 1989, Microbial Pathogen. 6:433-443) that although such attenuated vaccines colonized the GALT reasonably well, they did so less efficiently than did *Salmonella* strains attenuated with Δcya and Δcrp mutations (Curtiss and Kelly, 1987, Infect. Immun. 55:3035-3043; U.S. Pat. No. 5,389,368). Furthermore, colonization levels by the phoQ12 (originally designated phoP12) mutant in the spleen were much lower than observed for vaccine strains attenuated by the presence of other mutations (Galan and Curtiss, 1989, Microbial Pathogen. 6:433-443). Subsequently, it has been learned that bile present in the intestinal tract of animal hosts can inhibit invasion of *Salmonella* into the intestinal mucosa and into the GALT (Van Velkinburgh et al., 1999, Infect Immun. 67:1614-1622) and, furthermore, that phoPQ mutants are more sensitive to bile than their wild-type parents (Prouty and Gunn, 2000, Infect. Immun. 68:6763-6769). In addition, it is now known that the PhoP regulated genes prgHIJK specify proteins that constitute and are essential for the assembly and function, in part, of the Type III secretion apparatus (Kimbrough and Miller, 2000, Proc. Natl. Acad. Sci. USA 97:11008-11013) that is critical to the ability of *Salmonella* to successfully invade cells in the intestinal mucosa and the GALT (Kubori et al., 1998, Science 280:602-605). It is noteworthy, that the prgHIJK genes are within the 40 kb inv gene cluster originally identified by us as of critical importance for the ability of *Salmonella* to invade cells in the intestinal mucosa and the GALT (Galan and Curtiss, 1989, Proc. Natl. Acad. Sci. USA 86:6383-6387). These inv genes are equally important for the ability of *Salmonella* to invade any mucosal cell surface, including the upper respiratory tract after intranasal immunization. It therefore follows, that the deletion of the promoter for the phoPQ operon and its replacement with the araC $P_{BAD}$ activator-promoter sequence would provide a means to enhance colonization of lymphoid tissues. This is because growth of the vaccine strain in medium with arabinose prior to oral immunization of an individual would maximize the ability of the vaccine strain to survive the bile encountered in the intestinal tract and to invade into and colonize the GALT. Such more efficient invasion and colonization of the GALT would also enhance the ability of the vaccine strain to colonize internal lymphoid tissues such as the mesenteric lymph nodes, liver and spleen more efficiently prior to display of attenuation due to non expression of the phoPQ regulatory genes (due to the absence of arabinose in animal tissues). FIG. 28 presents the nucleotide sequence of the *S. typhimurium* phoPQ operon (essentially identical to the sequences in *S. paratyphi* A and *S. typhi*) and its promoter with flanking gene sequences and indicates the nucleotides of the phoPQ promoter ($P_{phoPQ}$) deleted. FIG. 20 presents the nucleotide sequence of the improved araC $P_{BAD}$ activator-promoter to replace $P_{phoPQ}$. FIG. 29 diagrams the construction of the suicide vector for the introduction of the Δ$P_{phoPQ}$-107::TT araC $P_{BAD}$phoPQ insertion-deletion mutation into the chromosome of vaccine strains. FIG. 30 diagrams the Salmonella chromosome with this insertion-deletion mutation. This insertion-deletion mutation can be introduced into strains of S. typhimurium, S. paratyphi A and S. typhi to be used as attenuated vaccine strains using the method of Kang et al. (2002, J. Bacteriol. 184:307-312).

Live attenuated bacterial vaccines with deletion-insertion mutations such as ΔPfur-233::TT araC $P_{BAD}$fur, ΔPfur-33::TT araC $P_{BAD}$fur, ΔPrpoS-183::TT araC $P_{BAD}$ rpoS and ΔPphoPQ-107::TT araC $P_{BAD}$phoPQ will cease to express the gene fused to $P_{BAD}$ soon after the vaccine strain is used to immunize an individual and is subject to an arabinose-free environment such that activation of the AraC protein, which requires arabinose, that is necessary to activate transcription from $P_{BAD}$ can no longer occur. A delay in the cessation of such $P_{BAD}$ dependent expression can be achieved by introducing the ΔaraBAD23 mutation present in χ8767 (Table 1) into the chromosome of such vaccine strains. The deletion of the araBAD genes for the catabolic breakdown and metabolism of arabinose causes arabinose accumulated internally by vaccine cells during their growth in arabinose-containing media to persist and continue to be available for the activation of the AraC protein to cause transcription from $P_{BAD}$ for an additional generation or so of growth following immunization (Guzman et al., 1995, J. Bacteriol. 177:4121-4130). This delay in onset of transcriptional shutoff can be further delayed by also introducing the ΔaraE25 mutation present in χ8477 (Table 1) that both decreases arabinose uptake into vaccine cells and also enhances its retention once internalized into the cell. Vaccine strains with both the ΔaraBAD23 and ΔaraE25 mutations are therefore grown in higher concentrations of arabinose prior to use for immunization than strains with only the ΔaraBAD23 mutation. FIG. 31 diagrams the suicide vectors (listed in Table 2) for introducing the ΔaraBAD23 and ΔaraE25 mutations into the chromosomes of vaccine strains and also diagrams the mutations after being introduced into the chromosome. It should be reiterated that vaccines with any of these regulated attenuating mutations, will decrease in virulence to ultimately display total attenuation when the Fur, RpoS and/or PhoPQ proteins are diluted out as a consequence of vaccine strain cell division in vivo and/or to proteolytic breakdown of these proteins.

Strains with the ΔPrpoS-183::TT araC $P_{BAD}$rpoS and ΔPphoPQ-107::TT araC $P_{BAD}$ phoPQ insertion-deletion mutations can be readily identified phenotypically. Strains with the first mutation will synthesize catalase when grown in the presence of arabinose as revealed by generation of vigorous bubbling upon addition of $H_2O_2$ to cultures, whereas no catalase will be synthesized by cultures grown in the absence of arabinose. This and a simple glycogen synthesis assay for revealing expression vs. non-expression of the rpoS gene are fully described in U.S. Pat. No. 6,024,961. Strains with the second mutation are readily identified by the ability to synthesize acid phosphatase encoded by the PhoP-activated gene phoN when strains are grown in the presence of arabinose but not when grown in the absence of arabinose. This assay is fully described in U.S. Pat. No. 5,424,065. PCR analyses with appropriate oligonucleotide probes can be used to rigorously validate the location and composition of the insertion-deletion mutations in the chromosomes of vaccine strains and DNA sequencing can be used to fully corroborate the presence of correct functioning DNA sequences.

The procedures described above in the Examples can be used to generate a diversity of vaccine strains that exhibit wild-type attributes during the initial immunization phase and gradually become fully attenuated the longer the vaccine strain resides in various lymphoid tissues within the immunized animal or human host. It is only necessary to delete sequences for binding of activators and repressors and the promoter that are upstream (5') to the Shine-Dalgarno (SD) ribosome binding sequence and the structural gene encoding a trait necessary for virulence of a bacterial pathogen. It is well known that mutations in the aroA, aroC, aroD, cya, crp, cdt, ompR, htrA, hemA, purA, purB, rfa, rfb, asd, ompC, and ompD genes will render bacteria such as *Salmonella* avirulent. In some of these cases, mutants with such mutations are not very immunogenic, presumably due to poor colonization of lymphoid tissues. It would therefore be logical to remove the activator and/or repressor binding sites and promoter sequence for these genes and replace this deleted sequence with an araC $P_{BAD}$ sequence. In this way, the virulence gene would be expressed when the strain is growing in medium with arabinose and would gradually cease to be expressed in vivo when the vaccine strain is unable to acquire arabinose to result in attenuation (avirulence) of the vaccine strain. This means for regulated delay in display of avirulence (attenuation) has numerous benefited applications in the construction of safe, efficacious bacterial vaccines.

Example 18

Delay in Cessation in LPS O-Antigen Side Chain Synthesis in a Vaccine Strain with the Δpmi-2426 Mutation by Blocking the Conversion of GDP-Mannose to GDP-Fucose by Inclusion of the Δ(gmd-fcl)-26 Mutation As shown by data presented in Tables 5, 6 and 7 (Example 6), the strain χ8754 with both the ΔPfur-223::TT araC $P_{BAD}$-fur and Δpmi-2426 mutations was somewhat less immunogenic than strains with either insertion-deletion or deletion mutation alone. Strains with pmi mutations are unable to use mannose as an energy source but are able to take it up into the cell, phosphorylate it and convert it to GDP-Mannose, one of the substrates necessary for synthesis of the LPS O-antigen side chains present in almost all *Salmonella* serotypes. However, *Salmonella* and other enteric bacteria can synthesize the exopolysaccharide colanic acid that is often synthesized in response to stresses. Fucose makes up one-third of the mass of colanic acid and is incorporated into this polymer using GDP-Fucose as a substrate (Grant et al., 1970, J. Bacteriol. 103:89-96). GDP-Fucose is synthesized from GDP-Mannose in two steps catalyzed by two enzymes encoded by the gmd and fcl genes (Andrianopoulos et al., 1998, J. Bacteriol. 180: 998-1001). Therefore, a vaccine strain with the Δpmi-2426 mutation alone might use some of the mannose taken up from the medium during its growth prior to immunization of an individual to be diverted to the synthesis of colanic acid by the conversion of GDP-Mannose to GDP-Fucose rather than use all of the accumulated GDP-Mannose to synthesize LPS O-antigen side chains. This would have the impact of causing a more rapid cessation in synthesis of LPS O-antigen side chains after immunization with a more rapid onset of the attenuating features associated with the presence of the pmi mutation. We have constructed a suicide vector with the Δ(gmd-fcl)-26 mutation that deletes both genes encoding enzymes for the conversion of GDP-Mannose to GDP-Fucose (FIG. 32; Table 2) and used it to introduce the Δ(gmd-fcol)-26 mutation (diagramed in FIG. 33) into the wild-type *S. typhimurium* UK-1 strain χ3761 and into the Δpmi-2426 containing UK-1 strain χ8650 to yield χ8831 and χ8868, respectively. As evidenced by the data in Table 10, the Δ(gmd-fcl)-26 mutant has the same virulence as the UK-1 wild-type parent χ3761 and the two strains with the Δpmi-2426 mutation are equally attenuated independent of the presence or absence of the Δ(gnd-fcol)-26 mutation. (Table 10 needs to be inserted after it is first cited in text.) This result is important in demonstrating that the presence of the Δ(gmd-fcl)-26 mutation that precludes conversion of GDP-Mannose to GDP-Fucose does not result in the buildup of a pool of GDP-Mannose sufficient to cause the double mutant to demonstrate some lethal infections in mice at high doses. Table 10 also presents data to show that χ8650 and χ8868 have essentially equal immunogenicity when the vaccine strains are grown in Luria broth (which contains 0.1% glucose) with 0.5% mannose prior to oral immunization of mice with decreasing doses of vaccine and challenged with high $10^9$ CFU doses of the wild-type χ3761 thirty days later. Based on these results, the Δ(gmd-fcl)-26 mutation will be included in all vaccine strains with the Δpmi-2426 mutation that are designed to be used to induce cross-protective immunity against *S. enterica* serotypes and other related enteric bacterial pathogens.

TABLE 10

Virulence of *S. typhimurium* UK-1 strains with Δ(gmd-fcl)-26, Δpmi-2426, and Δ(gmd-fcl)-26 Δpmi-2426 mutations in 8-week-old female BALB/c mice following oral inoculation and protectiv immunity by strains with Δpmi-2426 with and without th Δ(gmd-fcl)-26 mutation[a]

| Strain Survivors/total challenge | Inoculating dose | Survivors/ total | Challenge dose | after |
|---|---|---|---|---|
| χ3761 (wild type) | $1.2 \times 10^7$ | 0/4 | | |
| χ8831 | $1.0 \times 10^5$ | 1/4 | ND | ND |
| Δ(gmd-fcl)-26 | $1.0 \times 10^4$ | 4/4 | | |
| | $1.0 \times 10^3$ | 4/4 | | |
| χ8650 | $1.1 \times 10^9$ | 4/5 | $1.2 \times 10^9$ | 4/4 |
| Δpmi-2426 | $1.1 \times 10^8$ | 4/5 | $1.2 \times 10^9$ | 3/4 |
| | $1.1 \times 10^7$ | 5/5 | $1.2 \times 10^9$ | 3/5 |
| | $1.1 \times 10^6$ | 5/5 | $1.2 \times 10^9$ | 2/5 |
| χ8868 | $1.1 \times 10^9$ | 5/5 | $1.2 \times 10^9$ | 4/5 |
| Δpmi-2426 | $1.1 \times 10^8$ | 4/5 | $1.2 \times 10^9$ | 4/4 |
| Δ(gmd-fcl)-26 | $1.1 \times 10^7$ | 5/5 | $1.2 \times 10^9$ | 3/5 |
| | $1.1 \times 10^6$ | 4/5 | $1.2 \times 10^9$ | 0/4 |

[a]Bacteria were grown in Luria broth (containing 0.1% glucose) supplemented with 0.5% mannose to $OD_{600}$ of ~0.8. Bacterial cells were collected by centrifugation and suspended in buffered saline with gelatin (BSG). Female BALB/c mice, 8-weeks-old, were orally inoculated with 20 μl of the bacterial suspension. Morbidity and mortality were observed for 30 days. Surviving mice were challenged 30 days after the initial inoculation with virulent wild-type UK-1 χ3761 grown in Luria broth. Morbidity and mortality observations were recorded daily for an additional 30 days postchallenge. Both inoculating and challenge doses were measured in CFU.

Example 19

Diminishing the Ability of Vaccine Strains Designed to Induce Cross-Protective Immunity Against Enteric Bacterial Pathogens to Persist In Vivo and/or be Shed and Persist in the Environment Live attenuated *Salmonella* vaccines used to prevent infection of broiler chickens with *Salmonella* and to diminish, if not eliminate, presence of pathogenic *Salmonella* on carcasses at slaughter should be designed to not persist in immunized animals for more than about three weeks after receiving the last immunizing dose. Broilers now go to market at about six weeks of age and receive a second booster immunization with live attenuated *Salmonella* vaccines at 10 to 14 days of age. This feature is not so important when using such vaccines to immunize larger animals including swine, calves, cattle, goats, sheep, turkeys and chickens raised as roasters or to supply meat for the "nugget" market that are slaughtered at a more advanced age than broiler chickens. On the other hand, persistence of live attenuated vaccine strains in the intestinal tract of immunized animals leads to their excretion in feces with the potential to contaminate and persist in various environmental niches. This is also undesirable since such surviving vaccines might cause immunization of individuals either not intended to be vaccinated or, in the case of human animal caretakers, not electing to be immunized. A further negative to potential persistence of vaccine strains in agricultural environments, would be to diminish need by producers/farmers to purchase new lots of vaccine to immunize every new lot of animals, and such a feature would dissuade commercial development and marketing of such live attenuated vaccines. In regard to these issues, note that the live attenuated vaccine strain χ8754 still demonstrates detectable low titers in mice (FIG. 9) 42 days after immunization. To address these concerns, we have and are continuing to develop genetic strategies to provide live attenuated bacterial vaccine strains with biological containment features to lessen their ability to persist in vivo and to survive in natural environments likely encountered if shed in feces.

It is most desirable that mutations that confer desirable biological containment features not attenuate infectivity of vaccine strains and permit the same level of initial colonization of lymphoid tissues as the attenuated vaccine strain without the mutation conferring biological containment. This is invariably the case if a wild-type virulent strain endowed with the mutation conferring biological containment has an $LD_{50}$ that is nearly identical to its wild-type parent. We have therefore used this parameter to initially select mutations that can or do provide biological containment that do not diminish infectivity and virulence.

Strains with mutations such as ΔfliC825 and ΔfljB217 are non-flagellate and are non-motile. These mutations have been introduced into live attenuated *Salmonella* vaccines to induce cross-protective immunity to diverse enteric bacterial pathogens since antibody responses to the FliC and FljB protein antigens are serotype specific and thus would be unimportant in inducing cross-protective immunity. Since *Salmonella* in polluted aqueous environments uses motility and chemotaxis to identify food sources and swim toward them, non-motile strains with ΔfliC and ΔfljB mutations would be less able to survive in nature due to an inability to identify and move toward food supplies. It should be noted that chemotaxis is also dependent on the presence of flagella and display of motility. A bacterial strain such as χ8602 (Table 1) has the ΔfliC825 and ΔfljB217 mutations. It is non-flagellate and non-motile and, importantly, has the same $LD_{50}$ as does its wild-type parent χ3339 (Table 11).

TABLE 11

Virulence of *S. typhimurium* strains with deletion and deletion-insertion mutations contributing to biological containment.

| Strain | Genotype | CFU/dose | Survival/total |
|---|---|---|---|
| χ3761 | UK-1 wild-type | $1 \times 10^7$ | 0/2 |
| | | $1 \times 10^6$ | 1/5 |
| | | $1 \times 10^5$ | 1/5 |
| χ3761 | wild-type | $1.5 \times 10^6$ | 0/4 |
| | | $1.5 \times 10^5$ | 1/4 |
| | | $1.5 \times 10^4$ | 3/4 |
| | | $1.0 \times 10^3$ | 4/4 |
| χ3761 | wild-type | $9 \times 10^5$ | 0/4 |
| | | $9 \times 10^4$ | 2/4 |
| χ8894 | ΔadrA1418 | $1.1 \times 10^8$ | 0/3 |
| | | $1.1 \times 10^7$ | 1/3 |
| | | $1.1 \times 10^5$ | 0/3 |
| χ8890 | ΔbcsABZC2118 | $1.5 \times 10^8$ | 0/3 |
| | | $1.5 \times 10^7$ | 0/3 |
| | | $1.5 \times 10^5$ | 1/3 |
| χ8892 | ΔbcsEFG2319 | $2.1 \times 10^9$ | 0/3 |
| | | $2.1 \times 10^7$ | 0/3 |
| | | $2.1 \times 10^5$ | 1/3 |

TABLE 11-continued

Virulence of S. typhimurium strains with deletion and deletion-insertion mutations contributing to biological containment.

| Strain | Genotype | CFU/dose | Survival/total |
|---|---|---|---|
| χ8844 | ΔendA2311 | $8.6 \times 10^6$ | 0/4 |
|  |  | $8.6 \times 10^5$ | 2/4 |
|  |  | $8.6 \times 10^4$ | 2/2 |
| χ8844 | ΔendA2311 | $3.0 \times 10^5$ | 0/2 |
|  |  | $3.0 \times 10^4$ | 1/2 |
| χ8831 | Δ(gmd-fcl)-26 | $5.9 \times 10^5$ | 1/4 |
|  |  | $5.9 \times 10^4$ | 4/4 |
|  |  | $5.9 \times 10^3$ | 4/4 |
|  |  | $5.9 \times 10^2$ | 4/4 |
| χ8831 | Δ(gmd-fcl)-26 | $8.6 \times 10^6$ | 0/4 |
|  |  | $8.6 \times 10^5$ | 0/4 |
|  |  | $8.6 \times 10^4$ | 0/4 |
|  |  | $8.6 \times 10^3$ | 1/4 |
| χ8882 | ΔrelA1123m | $8.0 \times 10^7$ | 0/4 |
|  |  | $8.0 \times 10^6$ | 1/5 |
|  |  | $8.0 \times 10^5$ | 1/4 |
|  |  | $8.0 \times 10^4$ | 3/4 |
|  |  | $8.0 \times 10^3$ | 4/4 |
| χ8857 | ΔyhiR36::TT | $2.0 \times 10^6$ |  |
|  |  | $2.0 \times 10^5$ | 1/4 |
|  |  | $2.0 \times 10^4$ | 4/4 |
| χ3339 | SL1344 wild-type | $1.0 \times 10^6$ | 0/4 |
| χ8602 | ΔfliC825 ΔfljB217 | $2.9 \times 10^6$ | 0/4 |
| SL1344 |  | $2.9 \times 10^5$ | 1/4 |
|  |  | $2.9 \times 10^4$ | 4/4 |

As discussed in Example 18, enteric bacteria are capable of synthesizing the exopolysaccharide colanic acid in response to stresses. The presence of colanic acid can enhance resistance to antibiotics and other anti-microbial drugs, enhance resistance to host defense mechanisms including attach by lysozyme, complement and phagocytes, and also confers enhanced resistance to death by desiccation (Lopez-Torres and Stout, 1996, Curr. Microbiol. 33:383-389)). The presence of the Δ(gmd-fcl)-26 mutation in vaccine strains would not only have the benefits described in Example 18, but would also contribute to the biological containment features of the vaccine. As presented in Table 10, χ8831 with the Δ(gmd-fcl)-26 mutation is as virulent as its wild-type parent χ3761.

Synthesis of the extracellular matrix composed of thin aggregative fimbriae (curli) and cellulose (Romling et al., 2001, Mol. Microbiol. 39:1452-1463) enables enteric bacteria to synthesize biofilms that enhance their ability to adhere to both biological and inanimate surfaces, that is to colonize and survive on these surfaces that are encountered in the intestinal tract and in the environment following excretion. We have thus constructed the ΔafgBAC811 mutation to abolish synthesis of thin aggregative fimbriae and introduced it into χ3339 to produce strain χ8606 (Table 1). We have also generated the ΔbcsABZC2118 and ΔbcsEFG2319 mutations to abolish ability to synthesize cellulose (Solano et al., 2002. Mol. Microbiol. 43:793-808) and introduced both mutations into χ3761 to produce χ8890 and χ8892, respectively (Table 1). As described in Example 17, synthesis of the extracellular matrix can also be abolished by various other mutations in regulatory genes. We thus constructed the ΔadrA1418 mutation that blocks the export of cellulose to the cell surface (Zogaj et al., 2001, Mol. Microbiol. 39:1452-1463; Romling et al., 2001, Mol. Microbiol. 36:10-23), even when there are no mutations in bcs genes, to generate strain χ8894. Strains with mutations in the mlrA gene (Brown et al., 2001, Mol. Microbiol. 41:349-363) are unable to synthesize either thin aggregative fimbriae or to export cellulose to the cell surface (since MlrA is necessary to express the adrA gene). A χ3339 derivative with a mutation in the mlrA gene, χ8702, is listed in Table 1. Data presented in Table 11 reveals that S. typhimurium strains with the ΔafgBAC811 (χ8606), ΔbcsABZC2118 (χ8890), ΔbcsEFG2319 (χ8892), ΔadrA1418 (χ8894) and mlrA34 (χ8702) mutations retain the virulence with similar $LD_{50}$ values as exhibited by their wild-type virulent parents. Thus these mutations preventing complete synthesis of the extracellular matrix are non attenuating.

Finkel and Kolter (2001, J. Bacteriol. 183:6288-93) demonstrated that E. coli could use exogenous DNA as a nutrient to survive during prolonged stationary phase growth and then found that a mutant strain with a mutation in the yhiR gene was less able to use DNA as a nutrient and thus survived very poorly during prolonged stationary phase growth in comparison to the wild-type parent. We have therefore generated the ΔyhiR36::TT mutation and introduced it into χ3761 to produce χ8857 (Table 1). In initial experiments during mixed cultivation, χ8857 only constituted 18% of the surviving bacterial population after four days in comparison to 82% for the wild-type strain. Since enteric bacteria have endonuclease I in their periplasmic space and could use this enzyme to initially degrade either linear or circular DNAs that might serve as nutrients, we generated the ΔendA2311 mutation and introduced it into χ3761 to yield χ8844 (Table 1) and into χ8857 to yield χ8865 with both ΔyhiR36 and endA2311 mutations (Table 1). χ8857, χ8854 and χ8865 all exhibit virulence similar to the wild-type parents (Table 11).

Enteric bacteria when subjected to nutrient starvation invoke a stringent regulatory response and shut down protein synthesis. This causes a cessation of any attempt at growth or cell division and thus invokes a "Rip van Winkle" type of survival response. To preclude this survival capability, we have generated the ΔrelA1123 mutation, since relA mutations uncouple the ability of bacteria to respond to starvation signals. Thus nutrient limitation results in continued attempts at macromolecular synthesis and growth and this unbalanced growth enhances the likelihood for cell death. χ8882 with the ΔrelA1123 mutation (Table 1) may exhibit a very low level of attenuation compared to its wild-type parent (Table 12).

FIG. 34 diagrams all the suicide vectors (listed in Table 2) for introducing each of the above-described mutations into the chromosomes of Salmonella vaccine strains to confer biological containment properties to the vaccine strains. FIG. 35 diagrams all the mutations after insertion into the chromosome. The transductional method of Kang et al. (2002, J. Bacteriol. 184:307-312) can be used to easily move these markerless deletion mutations to other bacterial vaccine strains being constructed. Some or all of these mutations can be included in any one strain to provide biological containment. This is facilitated by the fact that there are no antibiotic resistance genes or other selective markers needed to select for inheritance of the markerless deletion mutation being introduced into any vaccine strain. This is also desirable since expression of antibiotic resistance by live attenuated bacterial vaccines would be unsafe if not unethical and is usually not permitted by regulatory agencies charged with evaluation and licensing of live attenuated bacterial vaccines.

An additional independent means to achieve essentially total biological containment of live attenuated bacterial vaccines is the subject on an independent patent application filed on Sep. 1, 2002 entitled "Regulated bacterial lysis for genetic vector delivery and antigen release." The technologies described in that application can be used to confer a most complete type of biological containment on vaccine strains since vaccine cells ultimately all die due to their lysis either in vivo or shortly after their excretion.

Example 20

Generation of sopB Mutations so that Live Attenuated *S. typhimurium* Vaccines Used to Orally Immunize Humans to Induce Cross-Protective Immunity Against Enteric Bacterial Pathogens will not Induce Gastroenteritis (Diarrhea) as a Consequence of Immunization We anticipate evaluating a genetically modified live attenuated *S. typhimurium* vaccine with the ΔPfur-33::TT araC $P_{BAD}$fur, Δpmi-2426, Δ(gmd-fcl)-26, ΔfliC825, ΔfliC2426 or ΔfliC-Var, ΔfljB217, and a selected optimal array of deletion mutations to provide biological containment properties to the vaccine for immunization of humans to evaluate induction of cross-protective immunity to diverse enteric bacterial pathogens. *S. enterica* strains, including *S. typhimurium*, are frequently the cause of gastroenteritis in humans with associated diarrhea and other unpleasantries. We surmise that the live attenuated *S. typhimurium* vaccine strain with the above listed mutations would be capable of inducing such disease, at least in some vaccinees, since it is still invasive and colonizes all lymphoid tissues, at least in mice. Various studies have implicated the effector proteins SopA, SopB, SopD and SopE2 as responsible for the induction of fluid secretion in animals susceptible to *S. enterica* induced gastroenteritis (Paesold et al., 2001, Annual Meeting of the Federation of American Society for Experimental Biology on Experimental Biology, P. A825; Zhang et al., 2002, Infect. Immun. 70:3843-3855). These proteins, encoded by genes in various regions of the chromosome, are all delivered to the cytoplasm of host cells in the infected individual by the Type III secretion system encoded in *Salmonella* Pathogenicity Island 1 (SPI-1) that contains the genetic information essential for *Salmonella* invasion into mucosal tissues (Galan and Zhou, 2000, Proc. Natl. Acad. Sci. USA 97:8754-8761; Galan, 2001, Annu. Rev. Cell Dev. Biol. 17:53-86). Various mutations will block the ability of *S. typhimurium* and *S. dublin* to cause fluid secretion resulting in diarrhea, but many of these mutations, such as in the sipB gene, yield strains that are non-invasive and unable to induce apoptosis and are therefore likely to be non-immunogenic. We will therefore construct a defined deletion mutation of the sopB gene that encodes an inositol phosphate phosphatase since the absence of this gene results in the most substantial reduction in fluid secretion compared to a sipB mutant (Paesold et al., 2001, Annual Meeting of the Federation of American society for Experimental Biology on Experimental Biology, P. A825; Zhang et al., 2002, Infect. Immun. 70:3843-3855) without reducing invasion ability. FIG. 36 provides the nucleotide and amino acid sequences of the *S. typhimurium* sopB gene and specifies the extend of the deletion to be present in the suicide vector diagramed in FIG. 37 for introducing the ΔsopB1925 mutation into the chromosome of *Salmonella* vaccine strains. The oligonucleotide primers to generate the deletion and to construct the suicide vector are given in FIG. 37. FIG. 38 provides a diagram of this ΔsopB1925 mutation in the *S. typhimurium* chromosome along with flanking genes. The ΔsopB1925 mutation will initially be introduced into the wild-type *S. typhimurium* UK-1 χ3761 strain to fully evaluate its virulence in mice, invasiveness into cells in culture and inability to induce fluid secretion using the ligated ilial loop assay in rabbits (that are highly susceptible to *S. enterica* induced diarrhea). We anticipate that virulence and invasiveness will be closely similar to these attributes displayed by the wild-type χ3761 parent whereas fluid secretion in the rabbit will be minimal compared to the wild-type parent. The ΔsopB1925 mutation will then be introduced into a live attenuated *S. typhimurium* vaccine strain that is highly immunogenic to determine whether the vaccine strain with the ΔsopB mutation is as immunogenic as its parent. If it is, we will introduce the ΔsopB1925 mutation into the vaccine strains derived from *S. typhimurium*, and also derived from *S. paratyphi* A and *S. typhi* (see Example 21 below), to induce cross-protective immunity to pathogenic enteric bacterial pathogens. If the presence of the ΔsopB1925 mutation introduces undesired attributes to the vaccine strain, we will proceed to evaluate use of ΔsopE2, ΔsopD and ΔsopA mutations (in that order) to arrive at the optimal balance between invasivness and colonization of lymphoid tissues to engender high immunogenicity and decreased ability to cause gastroenteritis. The goal is a safe, efficacious vaccine that will be "user friendly".

Example 21

Construction of Live Attenuated *S. paratyphi* A and *S. typhi* Vaccines for Optimal Induction of Cross-Protective Immunity Against Enteric Bacterial Pathogens Since there is little information that would validate the concept that a live attenuated *S. typhimurium* vaccine to induce cross-protective immunity to diverse enteric bacterial pathogens would be efficacious in humans, it is appropriate to also construct and evaluate (in human volunteers) human host-adapted *S. paratyphi* A and *S. typhi* vaccines for this purpose. Such a vaccine derived from *S. paratyphi* A would be particularly beneficial since there is currently no live attenuated vaccine to protect against *S. paratyphi* A infection that results in enteric fever with considerable global morbidity and mortality. We will use a well-characterized *S. paratyphi* A strain, χ8387, that we derived from ATCC 9281. As the *S. typhi* parents we will use both our RpoS+ derivative of *S. typhi* Ty2, χ8438 (see U.S. Pat. No. 6,383,496), and the RpoS+ *S. typhi* ISP1820 strain χ3744. These parent strains are listed in Table 1. Using suicide vectors listed in Table 2, individual strains with each defined deletion or insertion-deletion mutation in its chromosome as listed in Table 1 and the transductional method for introducing markerless mutations into the chromosome of bacterial strains (Kang et al., 2002, J. Bacteriol. 184:307-312), we will construct derivatives of χ8387, χ8438 and χ3744 that possess the ΔPfur-33:: TT araC $P_{BAD}$fur, Δpmi-2426, Δ(gmd-fcl)-26, ΔfliC825 or ΔfliC-Var, ΔfljB217, and a selected optimal array of deletion mutations to provide biological containment. We will also introduce the ΔsopB1925 (or other Δsop mutation, if necessary) into each strain. This is due to the widespread observation that some 10 to 15 percent of vaccinees receiving a candidate attenuated *S. typhi* vaccine have diarrhea. Thus introducing a sopB mutation would eliminate this problem. Constructed strains will be fully characterized phenotypically and genotypically by all the relevant procedures described in the preceding Examples. Since there is no animal model to evaluate *S. paratyphi* A and *S. typhi* candidate vaccines, evaluation for safety and efficacy will require evaluation in human volunteers. Animal data correlated with induced antibody titers monitored by the modified ELISA method described in Example 15 will, however, be instructive in evaluating antibodies induced in humans in relation to their likely ability to induce cross-protective immunity to diverse enteric bacterial pathogens.

Example 22

Use of Live Attenuated *Salmonella* Vaccines Inducing Cross-Protective Immunity to Enteric Bacterial Pathogens or Displaying Regulated Delayed Display of Attenuation as Recombinant Attenuated Vaccine Antigen Delivery Vectors to Induce Immunity to More Distantly Related Enteric Pathogens Using Functional Balanced-Lethal Host-Vector Constructions Live attenuated *Salmonella* vaccines are very useful as antigen delivery vectors to induce protective immunity to pathogens whose genes for protective antigens are contained within and expressed by the live recombinant attenuated vaccine. These technologies are described in U.S. Pat. No. 5,888,799. The stable maintenance and high-level expression of cloned genes on plasmid vectors by these live recombinant attenuated *Salmonella* vaccines in vivo following immunization of an animal or human host is achieved by using a balanced-lethal host-vector system as fully described in U.S. Pat. No. 5,672,345 and in a pending application filed Oct. 11, 2000 entitled "Functional balanced-lethal host-vector system" (U.S. Ser. No. 09/868,499). In these vaccine constructs, the chromosome of the vaccine strain possesses a mutation such as ΔasdA16 that imposes an obligate requirement for diaminopimelic acid (DAP), an essential constituent of the rigid layer of the bacterial cell wall, an amino acid that is only synthesized by bacteria and that is unavailable in animal tissues. In the absence of DAP, a strain with an asd mutation (or other mutation imposing a requirement for DAP) will outgrow its wall due to DAP-less death, which occurs by cell lysis. This system is operable as a vaccine if the plasmid vector encoding a protective protein antigen from some pathogen possess a wild-type copy of the asd gene (or a wild-type homolog to the mutated chromosomal gene imposing the requirement for DAP) such that a complementation heterozygote is established. In this case, so long as the plasmid vector with the wild-type complementing gene is maintained in the mutant attenuated bacterial vaccine, the recombinant vaccine will survive in vivo and continue producing the protective antigen as a factory to continuously stimulate the immunized host to elicit immune responses that will later protect the immunized host against infection by the pathogen whose protective antigen was synthesized and delivered to the host by the live recombinant attenuated vaccine. FIG. 39 diagrams two suicide vectors (Table 2) for introducing the ΔasdA16 mutation into the *S. typhimurium* chromosome and the ΔasdA25 mutation into the *S. paratyphi* A and *S. typhi* chromosomes. The necessity for two suicide vectors is due to the existence of a 24 base pair difference and an additional 30 base pair insertion adjacent to the asd gene in the human host-adapted *S. paratyphi* A and *S. typhi* strains that are not present adjacent to the asd gene in *S. typhimurium*. FIG. 40 diagrams the mutations and flanking sequences within the chromosomes of the three *Salmonella* serotypes. The transductional procedure of Kang et al. (2002, J. Bacteriol. 184: 307-312) can be used to move the ΔasdA16 and ΔasdA25 mutations to other strains such as those with the insertion-deletion mutations ΔPfur-33::TT araC $P_{BAD}$fur, ΔPrpoS-183::TT araC $P_{BAD}$ rpoS and ΔPphoPQ-107::TT araC $P_{BAD}$ phoPQ causing regulated delayed expression of attenuation. These strains would be used in conjunction with $Asd^+$ plasmid vectors (FIG. 41) modified to specify synthesis of protective antigens from other pathogens. FIG. 42 gives the nucleotide sequence of the $P_{trc}$ promoter and the multiple cloning sites useful for such constructions with these $Asd^+$ vectors. Although the technology is applicable to expressing protective antigens from any pathogen, special attenuation would be focused on enhancing induction of immunity to enteric bacterial pathogens that are unrelated or not closely related to Salmonella. These might therefore include expression of protective antigens from enteric bacterial pathogens such as *Campylobacter jejuni, Listeria monocytogenes, Shigella* species, *E. coli* strains, *Enterococcus* species, *Clostridium* species, etc. In these cases, the host strain would also contain mutations to enhance induction of cross-protective immunity such as the ΔPfur-33::TT araC $P_{BAD}$fur, Δpmi-2426, Δ(gmd-fcl)-26, ΔfliC825, ΔfliC2426 or ΔfliC-Var, ΔfljB217 and selected mutations to enhance biological containment properties.

Example 23

Regulated Delayed Over-Expression of the Type I Fimbrial Adhesin Protein FimH to Enhance Induction of Cross-Protective Immunity Against Enteric Bacterial Pathogens The FimH adhesive protein on type 1 fimbriae is antigenically and structurally conserved (Abraham et al., 1988, Nature 336:682-684) and the amino acid sequence of the protein in all *S. enterica* serotypes for which sequence information exists are 98 to 99 percent identical (based on GenBank analysis). Therefore, the induction of a strong immune response, especially a mucosal immune response, will likely contribute significantly to the induction of cross-protective immunity. We (Lockman and Curtiss, 1990, Infect. Immun. 58:137-143; Lockman and Curtiss, 1992, Infect. Immun. 60:491-496; Lockman and Curtiss, 1992, Mol. Microbiol. 6:933-945) had previously found that bacterial cells expressing type 1 fimbriae were unaltered in virulence and colonizing ability but were more rapidly cleared from blood than mutants unable to synthesize type 1 fimbriae. Such cells are more susceptible to phagocytosis (Ofek and Sharon, 1988, Infect. Immun. 56:539-547) and may also be more rapidly cleared from lymphoid tissues. These attributes might be intensified with a vaccine strain genetically altered to over express either type 1 fimbriae or just the FimH adhesive protein, which in either case could lead to hyper attenuation of the vaccine strain to reduce its immunogenicity. We have therefore devised a means to construct a live recombinant attenuated *Salmonella* vaccine that will give a delayed over expression of the *S. typhimurium* FimH protein after the vaccine strain has colonized lymphoid tissues. We have $Asd^+$ vectors pYA3337 with the low copy number pSC101 ori, pYA3332 with the moderately low p15A ori, pYA3342 with the moderate to high pBR on and pYA3341 with the high copy number pUC ori. All of these $Asd^+$ vectors that are diagramed in FIG. 41 have the $P_{trc}$. promoter to drive expression of genes cloned into the multiple cloning site whose sequence (that is the same in all four vectors) is presented in FIG. 42. Transcription from $P_{trc}$ promoter is repressed (prevented) if the LacI repressor protein is present in the cytoplasm of the bacterial cell. To achieve this, we have constructed as diagramed in FIG. 43 the insertion-deletion mutation ΔilvG3::TT araC $P_{BAD}$ lacI TT and a suicide vector for its introduction into the chromosome of vaccine strains. When strains with this insertion-deletion mutation are grown with arabinose in the medium, LacI protein is synthesized. After immunization, LacI protein decreases in concentration as a consequence of cell division and the degree of repression of a $P_{trc}$ promoter would gradually decrease with an eventual high-level constitutive expression of any gene sequence controlled by $P_{trc}$.

Further delay in de-repression of genes controlled by $P_{trc}$ on Asd⁺ vectors can be achieved, as describe in Example 17, by introducing into the vaccine strain the ΔaraBAD23 and ΔaraE25 deletion mutations using the suicide vectors diagramed in FIG. 31. FIG. 44 provides the nucleotide and amino acid sequences of the S. typhimurium fimH gene and FimH protein. The strategy, using PCR and the listed oligonucleotide probes to clone either the entire fimH gene or a sequence specifying its first 100 amino acids into any of the Asd⁺ vectors diagramed in FIG. 41 using the multiple cloning site diagramed in FIG. 42, is diagramed in FIG. 45. It is known that the first 100 amino acids of the FimH protein specify the adhesive properties of type 1 fimbriae (Thankavel et al., 1997, J. Clin. Invest. 100:1123-1126) and that immune responses to this 100 amino acid sequence block adherence of type 1 expressing bacteria to host cells possessing the receptor for type 1 fimbriae. Construction of simple attenuated vaccine strains with either of the two fimH inserts into anyone of the four Asd+ vectors introduced into strains with the ΔilvG3::TT araC $P_{BAD}$ lad TT and with and without the ΔaraBAD23 and ΔaraE25 mutations will lead to comparative studies on the stability, colonizing ability and immunogenicity of each construct. A construction with the best attributes and inducing high mucosal and systemic antibody titers against FimH that block type 1 fimbriae-mediated adherence will be the basis for further modification and enhancement of a vaccine with other insertion-deletion and deletion mutations demonstrated to maximize induction of cross-protective immunity against enteric bacterial pathogens.

What is claimed is:

1. A live attenuated strain of *Salmonella* comprising
   (a) a regulatable araCP$_{BAD}$ promotor that is operably linked to a fur gene, wherein said fur gene is expressed when said attenuated strain is in the intestinal tract of an individual and said fur gene is not expressed when said attenuated strain is within internal tissues of an individual and wherein non-expression of said fur gene in vivo causes synthesis of iron regulated outer membrane proteins (IROMPs); and
   (b) a means for regulating synthesis of an LPS O-antigen, wherein said LPS O-antigen ceases to be synthesized in vivo, exposing an LPS core oligosaccharide antigen that is conserved among *Salmonella* species;
   wherein said attenuated strain is a *Salmonella typhimurium* strain and has enhanced ability to induce immune responses against *Salmonella typhimurium* and *Salmonella enteritidis* species.

2. The live attenuated strain of claim 1 wherein said means for regulating synthesis of an LPS O-antigen comprises a mutation in a gene that encodes a product necessary for synthesis of LPS O-antigen.

3. The live attenuated strain of claim 2, wherein said means for regulating synthesis of an LPS O-antigen comprises a mutation in the pmi gene.

4. The live attenuated strain of claim 1, comprising a Δpmi mutation.

5. The live attenuated strain of claim 1 comprising a ΔPfun:: TT araCP$_{BAD}$fur genetic construction.

6. A live attenuated strain, wherein said strain is a *Salmonella typhimurium* comprising
   (a) a ΔPfur::TT araCP$_{BAD}$fur deletion-insertion mutation; and
   (b) a Δpmi mutation.

* * * * *

SEQUENCE LISTING

```
<160> NUMBER OF SEQ ID NOS: 21

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
ggggtacccg aagacctgct gcgac                                            25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
ccgaattcaa ttacacacac ccggt                                            25

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
ccgaattcat cccgtcaggg aacgg                                            25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
gcgagctcat ttgccgctgc tggtc                                            25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
```

```
ggggtacctg gcaactttcc ggcgg                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
ccgaattcct tttatgacgc cggac                                              25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
ccgaattctt atgattaagg aggca                                              25

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
gcgagctcgc gatatagttc gcata                                              25

<210> SEQ ID NO 9
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 9
ggcggatcct gtcatctaat gagcggaat                                          29

<210> SEQ ID NO 10
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 10
gccgaattca agtaacgata cctacaggc                                          29

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 11
cgcgaattca tcctacacgg caggtgaat                                          29

<210> SEQ ID NO 12
<211> LENGTH: 29
<212> TYPE: DNA
<213> ORGANISM: Artificial Sequence
```

```
<220> FEATURE:
<223> OTHER INFORMATION: Synthetic oligonucleotide

<400> SEQUENCE: 12
ccgaagcttt cactgcaacc atgaatgac                                29

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 13
cgggatccgt tatcggcaat ctggaggcaa                               30

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
catgcatgca ggcaggttca ggtacggtga                               30

<210> SEQ ID NO 15
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 15
ggggtaccta atcaacacta acagtct                                  27

<210> SEQ ID NO 16
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 16
ccgaattcag cagactgaac cgccagt                                  27

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
ccgaattcgg ggcttttca t                                         21

<210> SEQ ID NO 18
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 18
gcgagctctt caagaattgc cagagac                                  27
```

```
<210> SEQ ID NO 19
<211> LENGTH: 230
<212> TYPE: PRT
<213> ORGANISM: Streptococcus pneumoniae

<400> SEQUENCE: 19

Leu Gln Ala Ser Asn Glu Ser Gln Arg Lys Glu Ala Asp Lys Lys Ile
1               5                   10                  15

Lys Glu Ala Thr Gln Arg Lys Asp Glu Ala Glu Ala Phe Ala Thr
                20                  25                  30

Ile Arg Thr Thr Ile Val Val Pro Glu Pro Ser Glu Leu Ala Glu Thr
                35                  40                  45

Lys Lys Lys Ala Glu Glu Ala Thr Lys Glu Ala Glu Val Ala Lys Lys
        50                  55                  60

Lys Ser Glu Glu Ala Ala Lys Glu Val Glu Val Glu Lys Asn Lys Ile
65                  70                  75                  80

Leu Glu Gln Asp Ala Glu Asn Glu Lys Lys Ile Asp Val Leu Gln Asn
                85                  90                  95

Lys Val Ala Asp Leu Glu Lys Gly Ile Ala Pro Tyr Gln Asn Glu Val
                100                 105                 110

Ala Glu Leu Asn Lys Glu Ile Ala Arg Leu Gln Ser Asp Leu Lys Asp
                115                 120                 125

Ala Glu Glu Asn Asn Val Glu Asp Tyr Ile Lys Glu Gly Leu Glu Gln
130                 135                 140

Ala Ile Thr Asn Lys Lys Ala Glu Leu Ala Thr Thr Gln Gln Asn Ile
145                 150                 155                 160

Asp Lys Thr Gln Lys Asp Leu Glu Asp Ala Glu Leu Glu Leu Glu Lys
                165                 170                 175

Val Leu Ala Thr Leu Asp Pro Glu Gly Lys Thr Gln Asp Glu Leu Asp
                180                 185                 190

Lys Glu Ala Ala Glu Ala Glu Leu Asn Glu Lys Val Glu Ala Leu Gln
                195                 200                 205

Asn Gln Val Ala Glu Leu Glu Glu Glu Leu Ser Lys Leu Glu Asp Asn
        210                 215                 220

Leu Lys Asp Ala Glu Thr
225                 230

<210> SEQ ID NO 20
<211> LENGTH: 257
<212> TYPE: PRT
<213> ORGANISM: Streptococcus pneumoniae

<400> SEQUENCE: 20

Leu Gln Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys Tyr Asp Glu
                35                  40                  45

Asp Gln Lys Lys Thr Glu Glu Lys Ala Ala Leu Glu Lys Ala Ala Ser
        50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Lys Asp Ala Ala Asp Lys Met
                85                  90                  95

Ile Asp Glu Ala Lys Lys Arg Glu Glu Glu Ala Lys Thr Lys Phe Asn
                100                 105                 110
```

```
Thr Val Arg Ala Met Val Val Pro Glu Pro Glu Gln Leu Ala Glu Thr
            115                 120                 125

Lys Lys Lys Ser Glu Glu Ala Lys Gln Lys Ala Pro Glu Leu Thr Lys
130                 135                 140

Lys Leu Glu Glu Ala Lys Ala Lys Leu Glu Ala Glu Lys Lys Ala
145                 150                 155                 160

Thr Glu Ala Lys Gln Lys Val Asp Ala Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Asp Tyr Ala Lys Glu Gly Phe
            195                 200                 205

Arg Ala Pro Leu Gln Ser Lys Leu Asp Ala Lys Ala Lys Leu Ser
210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu

<210> SEQ ID NO 21
<211> LENGTH: 487
<212> TYPE: PRT
<213> ORGANISM: Streptococcus pneumoniae

<400> SEQUENCE: 21

Leu Gln Ala Ser Asn Glu Ser Gln Arg Lys Glu Ala Asp Lys Lys Ile
1               5                   10                  15

Lys Glu Ala Thr Gln Arg Lys Asp Glu Ala Glu Ala Ala Phe Ala Thr
                20                  25                  30

Ile Arg Thr Thr Ile Val Val Pro Glu Pro Ser Glu Leu Ala Glu Thr
            35                  40                  45

Lys Lys Lys Ala Glu Glu Ala Thr Lys Glu Ala Glu Val Ala Lys Lys
50                  55                  60

Lys Ser Glu Glu Ala Ala Lys Glu Val Glu Val Glu Lys Asn Lys Ile
65                  70                  75                  80

Leu Glu Gln Asp Ala Glu Asn Glu Lys Lys Ile Asp Val Leu Gln Asn
                85                  90                  95

Lys Val Ala Asp Leu Glu Lys Gly Ile Ala Pro Tyr Gln Asn Glu Val
            100                 105                 110

Ala Glu Leu Asn Lys Glu Ile Ala Arg Leu Gln Ser Asp Leu Lys Asp
            115                 120                 125

Ala Glu Glu Asn Asn Val Glu Asp Tyr Ile Lys Glu Gly Leu Glu Gln
            130                 135                 140

Ala Ile Thr Asn Lys Lys Ala Glu Leu Ala Thr Thr Gln Gln Asn Ile
145                 150                 155                 160

Asp Lys Thr Gln Lys Asp Leu Glu Asp Ala Glu Leu Glu Leu Glu Lys
                165                 170                 175

Val Leu Ala Thr Leu Asp Pro Glu Gly Lys Thr Gln Asp Glu Leu Asp
            180                 185                 190

Lys Glu Ala Ala Glu Ala Glu Leu Asn Glu Lys Val Glu Ala Leu Gln
            195                 200                 205

Asn Gln Val Ala Glu Leu Glu Glu Glu Leu Ser Lys Leu Glu Asp Asn
            210                 215                 220
```

```
-continued

Leu Lys Asp Ala Glu Thr Leu Gln Ser Pro Val Ala Ser Gln Ser Lys
225                 230                 235                 240

Ala Glu Lys Asp Tyr Asp Ala Ala Lys Lys Asp Ala Lys Asn Ala Lys
                245                 250                 255

Lys Ala Val Glu Asp Ala Gln Lys Ala Leu Asp Ala Lys Ala Ala
            260                 265                 270

Gln Lys Lys Tyr Asp Glu Asp Gln Lys Lys Thr Glu Glu Lys Ala Ala
        275                 280                 285

Leu Glu Lys Ala Ala Ser Glu Glu Met Asp Lys Ala Val Ala Ala Val
    290                 295                 300

Gln Gln Ala Tyr Leu Ala Tyr Gln Gln Ala Thr Asp Lys Ala Ala Lys
305                 310                 315                 320

Asp Ala Ala Asp Lys Met Ile Asp Glu Ala Lys Lys Arg Glu Glu Glu
                325                 330                 335

Ala Lys Thr Lys Phe Asn Thr Val Arg Ala Met Val Val Pro Glu Pro
            340                 345                 350

Glu Gln Leu Ala Glu Thr Lys Lys Ser Glu Glu Ala Lys Gln Lys
        355                 360                 365

Ala Pro Glu Leu Thr Lys Lys Leu Glu Glu Ala Lys Ala Lys Leu Glu
    370                 375                 380

Glu Ala Glu Lys Lys Ala Thr Glu Ala Lys Gln Lys Val Asp Ala Glu
385                 390                 395                 400

Glu Val Ala Pro Gln Ala Lys Ile Ala Glu Leu Glu Asn Gln Val His
                405                 410                 415

Arg Leu Glu Gln Glu Leu Lys Glu Ile Asp Glu Ser Glu Ser Glu Asp
            420                 425                 430

Tyr Ala Lys Glu Gly Phe Arg Ala Pro Leu Gln Ser Lys Leu Asp Ala
        435                 440                 445

Lys Lys Ala Lys Leu Ser Lys Leu Glu Glu Leu Ser Asp Lys Ile Asp
    450                 455                 460

Glu Leu Asp Ala Glu Ile Ala Lys Leu Glu Asp Gln Leu Lys Ala Ala
465                 470                 475                 480

Glu Glu Asn Asn Asn Val Glu
                485
```